US009644192B2

(12) United States Patent
Goedegebuur et al.

(10) Patent No.: US 9,644,192 B2
(45) Date of Patent: *May 9, 2017

(54) VARIANT *HUMICOLA GRISEA* CBH1.1

(71) Applicant: Danisco US Inc., Palo Alto, CA (US)

(72) Inventors: Frits Goedegebuur, Vlaardingen (NL); Peter Gualfetti, San Francisco, CA (US); Colin Mitchinson, Half Moon Bay, CA (US); Edmund Larenas, Moss Beach, CA (US)

(73) Assignee: Danisco US Inc., Genencor DivisionCA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/464,150

(22) Filed: Aug. 20, 2014

(65) Prior Publication Data
US 2015/0079638 A1    Mar. 19, 2015

Related U.S. Application Data

(62) Division of application No. 13/744,316, filed on Jan. 17, 2013, now Pat. No. 8,828,702, which is a division of application No. 13/092,068, filed on Apr. 21, 2011, now Pat. No. 8,377,659, which is a division of application No. 11/825,498, filed on Jul. 6, 2007, now Pat. No. 7,998,711, which is a division of application No. 10/810,277, filed on Mar. 26, 2004, now Pat. No. 7,459,299.

(60) Provisional application No. 60/459,734, filed on Apr. 1, 2003.

(51) Int. Cl.
  C12N 9/42     (2006.01)
  C12N 1/20     (2006.01)
  C12N 15/00    (2006.01)
  C12P 19/00    (2006.01)
  C12P 19/02    (2006.01)
  C12P 21/06    (2006.01)
  C07H 21/04    (2006.01)
  C12P 19/14    (2006.01)

(52) U.S. Cl.
  CPC ............ *C12N 9/2437* (2013.01); *C12P 19/02* (2013.01); *C12P 19/14* (2013.01); *C12Y 302/01091* (2013.01)

(58) Field of Classification Search
  None
  See application file for complete search history.

(56) References Cited

U.S. PATENT DOCUMENTS

| 4,822,516 A | 4/1989 | Suzuki et al. |
| 5,246,853 A | 9/1993 | Clarkson et al. |
| 5,457,046 A | 10/1995 | Wöldike et al. |
| 5,475,101 A | 12/1995 | Ward et al. |
| 6,268,328 B1 | 7/2001 | Mitchinson et al. |
| 7,452,707 B2 | 11/2008 | Goedegebuur et al. |
| 2005/0277172 A1 | 12/2005 | Day et al. |

FOREIGN PATENT DOCUMENTS

| EP | 0137280 | 4/1985 |
| EP | 1142992 | 10/2001 |
| JP | S64-020089 | 1/1989 |
| JP | 2001-054392 | 2/2001 |
| WO | WO 91/00353 | 1/1991 |
| WO | WO 91/04673 | 4/1991 |
| WO | WO 92/06209 | 4/1992 |
| WO | WO 94/28117 | 12/1994 |
| WO | WO 96/00281 | 1/1996 |
| WO | WO 98/21339 | 5/1998 |
| WO | WO 98/31821 | 7/1998 |
| WO | WO 02/12466 | 2/2002 |
| WO | WO 03/000941 | 1/2003 |

OTHER PUBLICATIONS

Gielkens et al. (Two cellobiohydrolase-encoding genes from *Aspergillus niger* require D-xylose and the xylanolytic transcriptional activator XlnR for their expression, Appl. Environ. Microbiol. 65:4340-4345(1999).*
Aleksenko, Alexei et al., "The plasmid replicator AMA1 in *Aspergillus nidulans* is an inverted duplication of a low-copy-number dispersed genomic repeat," *Molecular Microbiology*, 19(3):565-574, 1996.
Alexopoulos, C. J., (1962), Introductory Mycology, New York:Wiley.
Altschul, Stephen F. et al., "Basic Local Alignment Search Tool," *J. Mol. Biol.*, 215:403-410, 1990.
Altschul, Stephen F. et al., "Gapped Blast and PSI-Blast: a new generation of protein database search programs," *Nucl. Acids Res.*, vol. 25, pp. 3389-3402, 1997.
Aro, Nina et al., "ACEII, a Novel Transcriptional Activator Involved in Regulation of Cellulase and Xylanase Genes of *Trichoderma reesei*," *J. Biol. Chem.*, 276(26):24309-24314, 2001.
Aubert, et al., Ed., p11 et seq., Academic Press, 1988.
Ausubel et al., Current Protocols in Molecular Biology, Greene Publishing, Associates and Wiley Interscience, N.Y. (1994).
Baker, John O. et al., "A New Thermostable Endoglucanase, *Acidothermus cellulolyticus* E1," *Applied Biochemistry and Biotechnology*, 45/46:245-256, 1994.
Baker, John O. et al., "Hydrolysis of Cellulose Using Ternary Mixtures of Purified Cellulases," *Applied Biochemistry and Biotechnology*, 70-72:395-403, 1998.
Ballance, D.J. et al., "Transformation of *Aspergillus nidulans* by the Orotidine-5'-Phosphate Decarboxylase Gene of *Neurospora crassa*," *Biochemical and Biophysical Research Communications*, 112(1): 284-289, Apr. 15, 1983.
Barclay, Stephen L. et al., "Efficient Transformation of *Dictyostelium discoideum* Amoebae," *Molecular and Cellular Biology*, 3:2117-2130, 1983.

(Continued)

Primary Examiner — Iqbal H Chowdhury

(57) ABSTRACT

Disclosed are variants of *Humicola grisea* Cel7A (CBH1.1), *H. jecorina* CBH1 variant or *S. thermophilium* CBH1, nucleic acids encoding the same and methods for producing the same. The variant cellulases have the amino acid sequence of a glycosyl hydrolase of family 7A wherein one or more amino acid residues are substituted.

9 Claims, 15 Drawing Sheets

(56) References Cited

OTHER PUBLICATIONS

Becker, Dieter et al., "Engineering of a glycosidase Family 7 cellobiohydrolase to more alkaline pH optimum: the pH behaviour of *Trichoderma reesei* Cel7A and its E223S/A224H/L225V/T226A/D262G mutant" *Biochem. J.*, 356:19-30 (2001).

Berges, Thierry et al., "Isolation of uridine auxotrophs from *Trichoderma reesei* and efficient transformation with the cloned ura3 and ura5 genes," *Curr. Genet.*, 19:359-365, 1991.

Bhikhabhai, Ramagauri et al., "Isolation of Cellulolytic Enzymes from *Trichoderma reesei* QM 9414," *J. Appl. Biochem.*, 6:336-345, 1984.

Boel, E. et aL, "Two different types of intervening sequences in the glucoamylase gene from *Aspergillus niger*," *The EMBO Journal*, 3(7):1581-1585, 1984.

Brumbauer, Aniko et al., "Fractionation of cellulase and β-glucosidase in a *Trichoderma reesei* culture liquid by use of two-phase partitioning," Bioseparation, 7:287-295, 1999.

Campbell, Edward I., et al., "Improved transformation efficiency of *Aspergillus niger* using the homologous niaD gene for nitrate reductase," *Current Genetics*, 16:53-56, 1989.

Cao, Qing-Na et al., "Penicillopepsin-JT2, a recombinant enzyme from *Penicillium janthinellum* and the contribution of a hydrogen bond in subsite $S_3$ to kcat," *Protein Science*, vol. 9, pp. 991-1001, 2000.

Coligan, J. E. et al., eds., Current Protocols in Immunology, 1991.

Deutscher, Murray P., "Rethinking Your Purification Procedure," Methods in Enzymology, vol. 182, No. 57, p. 779, 1990.

de Oliviera et al., "Sequence of cbh-1 gene of Humicola grisea var.thermoidea," *Nucleic Acids Research*, V. 18, p. 668, 1990.

Ellouz, S. et al., "Analytical Separation of *Trichoderma reesei* Cellulases by Ion-Exchange Fast Protein Liquid Chromatography," *Journal of Chromatography*, 396:307-317, 1987.

Filho, Edivaldo X. F., "Purification and characterization of a β-glucosidase from solid-state cultures of *Humicola grisea* var. thermoidea," *Can. J. Microbiol.*, 42:1-5, 1996.

Fliess, A. et al., "Characterization of Cellulases by HPLC Separation," *Eur. J. Appl. Microbiol. Biotechnol.*, 17:314-318, 1983.

Freshney, R. I., ed., *Animal Cell Culture*, 1987.

Gateway™ Cloning Technology, Intruction Manual, Version 1, pp. 34-38. (Date not given).

Gloss, Lisa M. et al., "Urea and Thermal Equilibrium Denaturation Studies on the Dimerization Domain of *Escherichia coli* Trp Repressor," *Biochem.*, vol. 36, No. 19, pp. 5612-5623, 1997.

Goedegebuur, Frits et aL, "Cloning and relational analysis of 15 novel fungal endoglucanases from family 12 glycosyl hydrolase," *Current Genetics*, vol. 41, pp. 89-98, 2002.

Goyal, Anil, et al., "Characteristics of Fungal Cellulases," *Bioresource Technology*, vol. 36, pp. 37-50, 1991.

Hale & Markham, The Harper Collins Dictionary of Biology, Harper Perennial, NY, 1991.

Halldorsdottir, S, et al., "Cloning, sequencing and overexpression of a *Rhodothermus marinus* gene encoding a thermostable cellulase of glycosyl hydrolase family 12," *Appl. Microbiol. Biotechnol.*, 49(31:277-284, 1998.

Hazell, B. W. et al., "Rapid transformation of high cellulase-producing mutant strains of *Trichoderma reesei* by Microprojectile bombardment," *Letters in Applied Microbiology*, 30:282-286, 2000.

Herr, D. et al., "Purification and Properties of an Extracellular β-Glucosidase from *Lenzites trabea*," *European Appl. Microbiol. Biotechnol.*, 5:29-36, 1978.

Hu, Qianjin, et al., "Antibodies Specific for the Human Retinoblastoma Protein Identify a Family of Related Polypeptides," *Molecular and Cellular Biology.* vol. 11, No. 11, pp. 5792-5799, 1991.

Hynes, Michael J., et al., "Isolation of Genomic Clones Containing the amdS Gene of *Aspergillus nidulans* and Their Use in the Analysis of Structural and Regulatory Mutations," *Molecular and Cellular Biology*, 3:1430-1439, 1983.

Ilmen, Marja et al., "Regulation of Cellulase Gene Expression in the Filamentous Fungus *Trichoderma reesei*," *Appl. and Envir. Micro.*, vol. 63, No. 4, pp. 1298-1306, Apr. 1997.

Innis, M. A. et al., "Expression, Glycosylation, and Secretion of an *Aspergillus* Glucoamylase by *Saccharomyces cerevisiae*," *Science*, 228:21-26, 1985.

Jeenes, David J. et al., "Heterologous Protein Production by Filamentous Fungi," *Biotechnology and Genetic Engineering Reviews*, vol. 9, pp. 327-367, 1991.

Kawaguchi, Takashi et al., "Cloning and sequencing of the cDNA encoding β-glucosidase 1 from *Aspergillus aculeatus*," *Gene*, 173:287-288, 1996.

Kelly, Joan M. et al., "Transformation of *Aspergillus niger* by the amdS gene of *Aspergillus nidulans*," *The EMBO Journal*, 4(2):475-479, 1985.

Knowles, Jonathan et al., "Cellulase families and their genes," *TIBTECH* 5, pp. 255-261, 1987.

Kriegler, Gene Transfer and Expression: A Laboratory Manual, 1990.

Krishna, S. Hari et al., "Simultaneous saccharification and fermentation of lignocellulosic wastes to ethanol using a thermotolerant yeast," *Bioresource Tech.*, 77:193-196, 2001.

Kuhls, K. et al., "Molecular evidence that the asexual industrialfungus *Trichoderma reesei* is a clonal derivative of the ascomycete *Hypocrea jecorina*," *Proc. Natl. Acad. Sci. USA*, vol. 93, pp. 7755-7760, Jul. 1996.

Kumar, Akhil et al., "Optimizing the Use of Cellulase Enzymes in Finishing Cellulosic Fabrics," *Textile Chemist and Colorist*, 29:37-42, Apr. 1997.

Linder, Marcus et al., "The roles and function of cellulose-binding domains," *Journal of Biotechnol.*, 57:15-28, 1997.

Lockington, Robin A. et al., Cloning and characterization of the ethanol utilization regulon in *Aspergillus nidulans, Gene*, 33:137-149, 1985.

Luo, J. et al., "Detection of a Stable Intermediate in the Thermal Unfolding of a Cysteine-Free Form of Dihydrofolate Reductase from *Escherichia coli*," *Biochem.*, vol. 34, No. 33, pp. 10669-10675, 1995.

McKnight, Gary L. et al., "Nucleotide Sequence of the Triosephosphate Isomerase Gene from Aspergillus nidulans: Implications for a Differential Loss of Introns," *Cell*, 46:143-147, 1986.

Medve, Jozsef et al., "Ion-exchange chromatographic purification and quantitative analysis of *Trichoderma reesei* cellulases cellobiohydrolase I, II and endoglucanase II by fast protein liquid chromatography," *J. Chromatography A*, 808:153-165, 1998.

Mitsuishi, Yasushi, et al., "Site-directed mutagenesis of the putative catalytic residues of *Trichoderma reesei*, cellobiohydrolase I and endoglucanase I," *FEBS*, 275(1.2):135-138, 1990.

Mohagheghi, A. et al., "Isolation and Characterization of *Acidothermus celluloyticus* gen. nov., sp. nov., a New Genus of Thermophilic, Acidophilic, Cellulolytic Bacteria," *International Journal of Systematic Bacteriology*, 36(3):435-443, 1986.

Mullaney, Edward J. et al., "Primary structure of the trpC gene from *Aspergillus nidulans*," *Mol. Gen. Genet.* 199:37-45, 1985.

Nidetzky, Bernd et al., "Specific Quantification of *Trichoderma reesei* Cellulases in Reconstituted Mixtures and its Application to Cellulase-Cellulose Binding Studies," *Biotechnology and Bioengineering*, vol. 44, pp. 961-966, 1994.

Nieves, Rafael A. et al., "Quantitation of Acidothermus cellulolyticus E1 Endoglucanase and Thermomonospora fusca $E_3$ Exoglucanase Using Enzyme-Linked Immunosorbent Assay (ELISA)," *Applied Biochemistry and Biotechnology*, 51/52:211-223, 1995.

Nunberg, Jack H. et al., "Molecular Cloning and Characterization of the Glucoamylase Gene of *Aspergillus awamori*," *Molecular and Cellular Biology*, 4:2306-2315, 1984.

Ohmiya, Kunio et al., "Structure of Cellulases and Their Applications," *Biotechnol. Gen. Engineer. Rev.*, vol. 14, pp. 365-414, 1997.

Okada, Hirofumi et al., "Molecular Characterization and Heterologous Expression of the Gene Encoding a Low-Molecular-Mass Endoglucanase from *Trichoderma reesei* QM9414," *Applied and Environmental Microbiology*, vol. 64, No. 2, pp. 555-563, 1990.

(56) References Cited

OTHER PUBLICATIONS

Ooi, Toshihiko et al., "Complete nucleotide sequence of a gene coding for *Aspergillus aculeatus* cellulase (FI-CMCase)," *Nucleic Acids Research*, vol. 18, No. 19, p. 5884, 1990.
Penttila, Merja et al. "Homology between cellulase genes of *Trichoderma reesei*: complete nucleotide sequence of the endoglucanase I gene," *Gene*, 45: 253-263, 1986.
Penttila, Merja E. et al., "A versatile transformation system for the cellulolytic filamentous fungus *Trichoderma reesei*," *Gene*, vol. 61, pp. 155-164, 1987.
Penttila, Merja E. et al., "Efficient secretion of two fungal cellobiohydrolases by *Saccharomyces cerevisiae*," *Gene*, 63:103-112, 1988.
Pere J. et al., "Use of Purified Enzymes in Mechanical Pulping," 1996 Tappi Pulping Conference, pp. 693-696, Nashville, TN.
Pourquie, J. et al., "Scale Up of Cellulase Production and Utilization," Biochemistry and Genetics of Cellulose Degradation, Academic Press Ltd., pp. 71-86, 1988.
Saarilahti, Hannu T. et al., "CelS: a novel endoglucanase identified from *Erwinia carotovora* subsp. *carotovora*," *Gene*, 90:9-14, 1990.
Sakamoto, S. et al., "Cloning and sequencing of cellulase cDNA from *Aspergillus kawachii* and its expression in *Saccharomyces cerevisiae*," *Curr. Genet.*, 27:435-439, 1995.
Saloheimo, M. et al., "EGIII, a new endoglucanase from *Trichoderma reesei*: the characterization of both gene and enzyme," *Gene*, 63:11-21, 1988.
Saloheimo, Anu et al., "A novel, small endoglucanase gene, egl5 from *Trichoderma reesei* isolated by expression in yeast," *Molecular Microbiology*, vol. 13, No. 2, pp. 219-228, 1994.
Saloheimo, Markku et al., "cDNA cloning of a *Trichoderma reesei* cellulase and demonstration of endoglucanase activity by expression in yeast," *Eur. J. Biochem.* vol. 249, pp. 584-591, 1997.
Sambrook, et al., Molecular Cloning: A Laboratory Manual (Second Edition), Cold Spring Harbor Press, Plainview, N.Y., 1989.
Schell, D. et al., "Dilute-Sulfuric Acid pretreatment of Corn Stover in Pilot-Scale Reactor," *Applied Biochemistry and Biotechnology*, vol. 105-108, pp. 69-85, 2003.
Schülein, Martin, "Cellulases of *Trichoderma reesei*," *Methods Enzymol.*, 160, 25, pp. 234-243, 1988.
Scopes, Robert K. et al., "Purification of All Glycolytic Enzymes from One Muscle Extract," *Methods Enzymol.*, 90:479-491, 1982.
Sheir-Neiss, G. et al., "Characterization of the secreted cellulases of *Trichoderma reesei* wild type and mutants during controlled fermentations," *Appl. Microbiol. Biotechnol.*, vol. 20, pp. 46-53, 1984.
Shoemaker, S. P. et al., "Enzymic Activities of Endo-1,4-β-D-Glucanases Purified From *Trichoderma viride*," *Biochemica et Biophysica Acta*, 523:133-146, 1978.
Shoemaker, S. et al., "Molecular Cloning of Exo-Cellobiohydrolase I Derived from *Trichoderma reesei* Strain L27," *Bio/Technology*, pp. 691-696, 1983.
Shoemaker, S. P. et al., "The cellulase system of *Trichoderma reesei*: Trichoderma strain improvement and expression of *Trichoderma* cellulase in yeast—ethanol production", World Biotech. Rep. vol. 2, pp. 593-600 (1984).
Singleton, et al., Dictionary of Microbiology and Molecular Biology, 2D ED., John Wiley and Sons, New York (1994).
Spilliaert, Rémi et al., "Cloning and sequencing of a *Rhodothermus marinus* gene, bglA, coding for a thermostable β-glucanase and its expression in *Escherichia coli*," *Eur. J. Biochem.*, 224(3):923-930. 1994.
Srisodsuk, Malee et al., "Role of the Interdomain Linker Peptide of *Trichoderma reesei* Cellobiohydrolase I in Its Interaction with Crystalline Cellulose," *The Journal of Biological Chemistry*, 268(28):20756-20761, 1993.
Srisodsuk, Malee et al., "*Trichoderma reesei* cellobiohydrolase I with an endoglucanase cellulose-binding domain: action on bacterial microcrystalline cellulose," *Journal of Biotechnology*, 57:49-57, 1997.
Stahlberg, Jerry et al., "A New Model for Enzymatic Hydrolysis of Cellulose Based on the Two-Domain Structure of Cellobiohydrolase I," *Bio/Technol.*, 9:286-290, 1991.
Strathern et al., eds., The Molecular Biology of the Yeast *Saccharomyces*, 1981.
Suurnäkki, A. et al., "*Trichoderma reesei* cellulases and their core domains in the hydrolysis and modification of chemical pulp," *Cellulose* 7:189-209, 2000.
Takashima, S., et al. "Cloning, sequencing, and expression of the cellulase genes of *Humicola grisea* var. *thermoidea*." *J. Biotech.* 50: 137-147, 1996.
Teeri, Tuula T. et al., "Homologous domains in *Trichoderma reesei* cellulolytic enzymes: gene sequence and expression of cellobiohydrolase II," *Gene*, 51:43-52, 1987.
Tomaz, Cândida T. et al., "Studies on the chromatographic fractionation of *Trichoderma reesei* cellulases by hydrophobic interaction," *J. Chromatography A*, 865:123-128, 1999.
Tomme, Peter et al., "Studies of the cellulolytic system of *Trichoderma reesei* QM 9414. Analysis of domain function in two cellobiohydrolases by limited proteolysis," *FEBS*, 170:575-581, 1988.
Tormo, José et al., "Crystal structure of a bacterial family-III cellulose-binding domain: a general mechanism for attachment to cellulose," *EMBO J.*, vol. 15, No. 21, pp. 5739-5751, 1996.
Te'o, Valentino S. J. et al., "Codon optimization of xylanase gene xynB from the thermophilic bacterium *Dictyoglomus thermophilum* for expression in the filamentous fungus *Trichoderma reesei*," *FEMS Microbiology Letters*, 190:13-19, 2000.
Van den Hondel et al., "Heterologous Gene Expression in Filamentous Fungi," More Gene Manipulations in Fungi, Chapter 18, pp. 396-428, 1991, Academic Press, Inc.
van Hartingsveldt, Wim et al., "Development of a homologous transformation system for *Aspergillus niger* based on the pyrG gene," *Mol. Gen. Genet.*, 206:71-75, 1987.
van Tilbeurgh, Herman et al., Separation of endo- and exo-type cellulases using a new affinity chromatography method, *FEBS*, vol. 169, No. 2, pp. 215-218, 1984.
van Tilbeurgh, Herman, et al., "Limited proteolysis of the cellobiohydrolase I from *Trichoderma reesei*," *FEBS*, 204(2):223-227, 1986.
Walseth, Curtis S., "Occurrence of Cellulases in Enzyme Preparations from Microorganisms," 35(5):228-233, 1952.
Ward, Michael et al., "Use of *Aspergillus* overproducing mutants, cured for integrated plasmid, to overproduce heterologous proteins," *Appl. Microbiol. Biotechnol.*, vol. 39, pp. 738-743, 1993.
Wood, T. M., "The Cellulase of *Fusarium solani* Purification and Specificity of the β-(1→4)-Glucanase and the β-D-Glucosidase Components," *Biochem. J.*, 121:353-362, 1971.
Wood, Thomas M. et al., "Methods for Measuring Cellulase Activities," *Methods in Enzymology*, vol. 160, No. 9, pp. 87-116, 1988.
Wood, Thomas M. et al., "Properties of cellulolytic enzyme systems," *Biochemical Society Transactions*, 611th Meeting, Galway, vol. 13, pp. 407-410, 1985.
Yelton, M. Melanie, et al, "Transformation of *Aspergillus nidulans* by using a trpC plasmid," *Proc. Natl. Acad. Sci.*, vol. 81, pp. 1470-1474, 1984.
EP search report.
PCT search report.
Gielkens et al. Two cellobiohydrolase-encoding genes from Aspergillus niger require D-xylose and the xylanolytic transcriptional activator XlnR for their expression.; Appl. Environ. Microbiol. 65:4340-4345(1999).

\* cited by examiner

*H. grisea* CBH1.1

Total Genomic Sequence (1638 Nucleotides)

```
   1  ATGCGTACCG CCAAGTTCGC CACCCTCGCC GCCCTTGTGG CCTCGGCCGC    50
  51  CGCCCAGCAG GCGTGCAGTC TCACCACCGA GAGGCACCCT TCCCTCTCTT   100
 101  GGAAGAAGTG CACCGCCGGC GGCCAGTGCC AGACCGTCCA GGCTTCCATC   150
 151  ACTCTCGACT CCAACTGGCG CTGGACTCAC CAGGTGTCTG GCTCCACCAA   200
 201  CTGCTACACG GGCAACAAGT GGGATACTAG CATCTGCACT GATGCCAAGT   250
 251  CGTGCGCTCA GAACTGCTGC GTCGATGGTG CCGACTACAC CAGCACCTAT   300
 301  GGCATCACCA CCAACGGTGA TTCCCTGAGC CTCAAGTTCG TCACCAAGGG   350
 351  CCAGCACTCG ACCAACGTCG GCTCGCGTAC CTACCTGATG GACGGCGAGG   400
 401  ACAAGTATCA GAGTACGTTC TATCTTCAGC CTTCTCGCGC CTTGAATCCT   450
 451  GGCTAACGTT TACACTTCAC AGCCTTCGAG CTCCTCGGCA ACGAGTTCAC   500
 501  CTTCGATGTC GATGTCTCCA ACATCGGCTG CGGTCTCAAC GGCGCCCTGT   550
 551  ACTTCGTCTC CATGGACGCC GATGGTGGTC TCAGCCGCTA TCCTGGCAAC   600
 601  AAGGCTGGTG CCAAGTACGG TACCGGCTAC TGCGATGCTC AGTGCCCCCG   650
 651  TGACATCAAG TTCATCAACG GCGAGGCCAA CATTGAGGGC TGGACCGGCT   700
 701  CCACCAACGA CCCCAACGCC GGCGCGGGCC GCTATGGTAC CTGCTGCTCT   750
 751  GAGATGGATA TCTGGGAAGC CAACAACATG GCTACTGCCT TCACTCCTCA   800
 801  CCCTTGCACC ATCATTGGCC AGAGCCGCTG CGAGGGCGAC TCGTGCGGTG   850
 851  GCACCTACAG CAACGAGCGC TACGCCGGCG TCTGCGACCC CGATGGCTGC   900
 901  GACTTCAACT CGTACCGCCA GGGCAACAAG ACCTTCTACG GCAAGGGCAT   950
 951  GACCGTCGAC ACCACCAAGA AGATCACTGT CGTCACCCAG TTCCTCAAGG  1000
1001  ATGCCAACGG CGATCTCGGC GAGATCAAGC GCTTCTACGT CCAGGATGGC  1050
1051  AAGATCATCC CCAACTCCGA GTCCACCATC CCCGGCGTCG AGGGCAATTC  1100
1101  CATCACCCAG GACTGGTGCG ACCGCCAGAA GGTTGCCTTT GGCGACATTG  1150
1151  ACGACTTCAA CCGCAAGGGC GGCATGAAGC AGATGGGCAA GGCCCTCGCC  1200
1201  GGCCCCATGG TCCTGGTCAT GTCCATCTGG GATGACCACG CCTCCAACAT  1250
1251  GCTCTGGCTC GACTCGACCT TCCCTGTCGA TGCCGCTGGC AAGCCCGGCG  1300
1301  CCGAGCGCGG TGCCTGCCCG ACCACCTCGG GTGTCCCTGC TGAGGTTGAG  1350
1351  GCCGAGGCCC CCAACAGCAA CGTCGTCTTC TCCAACATCC GCTTCGGCCC  1400
1401  CATCGGCTCG ACCGTTGCTG GTCTCCCCGG CGCGGGCAAC GGCGGCAACA  1450
1451  ACGGCGGCAA CCCCCCGCCC CCACCACCA CCACCTCCTC GGCTCCGGCC  1500
1501  ACCACCACCA CCGCCAGCGC TGGCCCCAAG CTGGCCGCT GGCAGCAGTG  1550
1551  CGGCGGCATC GGCTTCACTG GCCCGACCCA GTGCGAGGAG CCCTACACTT  1600
1601  GCACCAAGCT CAACGACTGG TACTCTCAGT GCCTGTAA              1638
```

*FIG._1*

**Putative Intron Sequence Deleted (GTACGTT...CAG = 413-472)
Gives the cDNA Sequence (1578 Nucleotides)**

```
   1  ATGCGTACCG CCAAGTTCGC CACCCTCGCC GCCCTTGTGG CCTCGGCCGC    50
  51  CGCCCAGCAG GCGTGCAGTC TCACCACCGA GAGGCACCCT TCCCTCTCTT   100
 101  GGAAGAAGTG CACCGCCGGC GGCCAGTGCC AGACCGTCCA GGCTTCCATC   150
 151  ACTCTCGACT CCAACTGGCG CTGGACTCAC CAGGTGTCTG GCTCCACCAA   200
 201  CTGCTACACG GGCAACAAGT GGGATACTAG CATCTGCACT GATGCCAAGT   250
 251  CGTGCGCTCA GAACTGCTGC GTCGATGGTG CCGACTACAC CAGCACCTAT   300
 301  GGCATCACCA CCAACGGTGA TTCCCTGAGC CTCAAGTTCG TCACCAAGGG   350
 351  CCAGCACTCG ACCAACGTCG GCTCGCGTAC CTACCTGATG GACGGCGAGG   400
 401  ACAAGTATCA GACCTTCGAG CTCCTCGGCA ACGAGTTCAC CTTCGATGTC   450
 451  GATGTCTCCA ACATCGGCTG CGGTCTCAAC GGCGCCCTGT ACTTCGTCTC   500
 501  CATGGACGCC GATGGTGGTC TCAGCCGCTA TCCTGGCAAC AAGGCTGGTG   550
 551  CCAAGTACGG TACCGGCTAC TGCGATGCTC AGTGCCCCCG TGACATCAAG   600
 601  TTCATCAACG GCGAGGCCAA CATTGAGGGC TGGACCGGCT CCACCAACGA   650
 651  CCCCAACGCC GGCGCGGGCC GCTATGGTAC CTGCTGCTCT GAGATGGATA   700
 701  TCTGGGAAGC CAACAACATG GCTACTGCCT TCACTCCTCA CCCTTGCACC   750
 751  ATCATTGGCC AGAGCCGCTG CGACGGCGAC TCGTGCGGTG GCACCTACAG   800
 801  CAACGAGCGC TACGCCGGCG TCTGCGACCC CGATGGCTGC GACTTCAACT   850
 851  CGTACCGCCA GGGCAACAAG ACCTTCTACG GCAAGGGCAT GACCGTCGAC   900
 901  ACCACCAAGA AGATCACTGT CGTCACCCAG TTCCTCAAGG ATGCCAACGG   950
 951  CGATCTCGGC GAGATCAAGC GCTTCTACGT CCAGGATGGC AAGATCATCC  1000
1001  CCAACTCCGA GTCCACCATC CCCGGCGTCG AGGGCAATTC CATCACCCAG  1050
1051  GACTGGTGCG ACCGCCAGAA GGTTGCCTTT GGCGACATTG ACGACTTCAA  1100
1101  CCGCAAGGGC GGCATGAAGC AGATGGGCAA GGCCCTCGCC GGCCCCATGG  1150
1151  TCCTGGTCAT GTCCATCTGG GATGACCACG CCTCCAACAT GCTCTGGCTC  1200
1201  GACTCGACCT TCCCTGTCGA TGCCGCTGGC AAGCCCGGCG CCGAGCGCGG  1250
1251  TGCCTGCCCG ACCACCTCGG GTGTCCCTGC TGAGGTTGAG GCCGAGGCCC  1300
1301  CCAACAGCAA CGTCGTCTTC TCCAACATCC GCTTCGGCCC CATCGGCTCG  1350
1351  ACCGTTGCTG GTCTCCCCGG CGCGGGCAAC GGCGGCAACA ACGGCGGCAA  1400
1401  CCCCCCGCCC CCCACCACCA CCACCTCCTC GGCTCCGGCC ACCACCACCA  1450
1451  CCGCCAGCGC TGGCCCCAAG GCTGGCCGCT GGCAGCAGTG CGGCGGCATC  1500
1501  GGCTTCACTG GCCCGACCCA GTGCGAGGAG CCCTACACTT GCACCAAGCT  1550
1551  CAACGACTGG TACTCTCAGT GCCTGTAA                           1578
```

*FIG._2*

**Translation of the cDNA Sequence Gives the *H. grisea var thermoidea*
CBH1 Precursor (i.e.: with Signal Sequence)
Protein Sequence (525 Amino Acids)**

```
  1  MRTAKFATLA ALVASAAAQQ ACSLTTERHP SLSWKKCTAG GQCQTVQASI   50
 51  TLDSNWRWTH QVSGSTNCYT GNKWDTSICT DAKSCAQNCC VDGADYTSTY  100
101  GITTNGDSLS LKFVTKGQHS TNVGSRTYLM DGEDKYQTFE LLGNEFTFDV  150
151  DVSNIGCGLN GALYFVSMDA DGGLSRYPGN KAGAKYGTGY CDAQCPRDIK  200
201  FINGEANIEG WTGSTNDPNA GAGRYGTCCS EMDIWEANNM ATAFTPHPCT  250
251  IIGQSRCEGD SCGGTYSNER YAGVCDPDGC DFNSYRQGNK TFYGKGMTVD  300
301  TTKKITVVTQ FLKDANGDLG EIKRFYVQDG KIIPNSESTI PGVEGNSITQ  350
351  DWCDRQKVAF GDIDDFNRKG GMKQMGKALA GPMVLVMSIW DDHASNMLWL  400
401  DSTFPVDAAG KPGAERGACP TTSGVPAEVE AEAPNSNVVF SNIRFGPIGS  450
451  TVAGLPGAGN GGNNGGNPPP PTTTTSSAPA TTTTASAGPK AGRWQQCGGI  500
501  GFTGPTQCEE PYTCTKLNDW YSQCL                             525
```

*FIG._3*

**Mature (i.e.: Expressed Protein with the Putative Signal Sequence Removed)
Protein Sequence (507 Amino Acids)**

```
  1  QQACSLTTER HPSLSWKKCT AGGQCQTVQA SITLDSNWRW THQVSGSTNC   50
 51  YTGNKWDTSI CTDAKSCAQN CCVDGADYTS TYGITTNGDS LSLKFVTKGQ  100
101  HSTNVGSRTY LMDGEDKYQT FELLGNEFTF DVDVSNIGCG LNGALYFVSM  150
151  DADGGLSRYP GNKAGAKYGT GYCDAQCPRD IKFINGEANI EGWTGSTNDP  200
201  NAGAGRYGTC CSEMDIWEAN NMATAFTPHP CTIIGQSRCE GDSCGGTYSN  250
251  ERYAGVCDPD GCDFNSYRQG NKTFYGKGMT VDTTKKITVV TQFLKDANGD  300
301  LGEIKRFYVQ DGKIIPNSES TIPGVEGNSI TQDWCDRQKV AFGDIDDFNR  350
351  KGGMKQMGKA LAGPMVLVMS IWDDHASNML WLDSTFPVDA AGKPGAERGA  400
401  CPTTSGVPAE VEAEAPNSNV VFSNIRFGPI GSTVAGLPGA GNGGNNGGNP  450
451  PPPTTTTSSA PATTTTASAG PKAGRWQQCG GIGFTGPTQC EEPYTCTKLN  500
501  DWYSQCL                                                 507
```

*FIG._4*

**Sequence Alignment of Two Public Sequences and variant *H. grisea* CBH1.1**

```
                          1                                                                         75
     CBS 225.63    (1)   QQACSLTTERHPSLSWKKCTAGGQCQTVQASITLDSNWRWTHQVSGSTNCYTGNKWDTSICTDAKSCAQNCCVDG
 D63515 Mature     (1)   QQACSLTTERHPSLSWKKCTAGGQCQTVQASITLDSNWRWTHQVSGSTNCYTGNKWDTSICTDAKSCAQNCCVDG
 X17258 Mature     (1)   QQACSLTTERHPSLSWNKCTAGGQCQTVQASITLDSNWRWTHQVSGSTNCYTGNKWDTSICTDAKSCAQNCCVDG
      Consensus    (1)   QQACSLTTERHPSLSWKKCTAGGQCQTVQASITLDSNWRWTHQVSGSTNCYTGNKWDTSICTDAKSCAQNCCVDG 76                                                                       150
     CBS 225.63   (76)   ADYTSTYGITTNGDSLSLKFVTKGQHSTNVGSRTYLMDGEDKYQTFELLGNEFTFDVDVSNIGCGLNGALYFVSM
 D63515 Mature    (76)   ADYTSTYGITTNGDSLSLKFVTKGQYSTNVGSRTYLMDGEDKYQTFELLGNEFTFDVDVSNIGCGLNGALYFVSM
 X17258 Mature    (76)   ADYTSTYGITTNGDSLSLKFVTKGQHSTNVGSRTYLMDGEDKYQTFELLGNEFTFDVDVSNIGCGLNGALYFVSM
      Consensus   (76)   ADYTSTYGITTNGDSLSLKFVTKGQHSTNVGSRTYLMDGEDKYQTFELLGNEFTFDVDVSNIGCGLNGALYFVSM 151                                                                      225
     CBS 225.63  (151)   DADGGLSRYPGNKAGAKYGTGYCDAQCPRDIKFINGEANIEGWTGSTNDPNAGAGRYGTCCSEMDIWEANNMATA
 D63515 Mature   (151)   DADGGLSRYPGNKAGAKYGTGYCDAQCPRDIKFINGEANIEGWTGSTNDPNAGAGRYGTCCSEMDIWEANNMATA
 X17258 Mature   (151)   DADGGLSRYPGNKAGAKYGTGYCDAQCPRDIKFINGEANIEGWTGSTNDPNAGAGRYGTCCSEMDIWEANNMATA
      Consensus  (151)   DADGGLSRYPGNKAGAKYGTGYCDAQCPRDIKFINGEANIEGWTGSTNDPNAGAGRYGTCCSEMDIWEANNMATA 226                                                                      300
     CBS 225.63  (226)   FTPHPCTIIGQSRCEGDSCGGTYSNERYAGVCDPDGCDFNSYRQGNKTFYGKGMTVDTTKKITVVTQFLKDANGD
 D63515 Mature   (226)   FTPHPCTIIGQSRCEGDSCGGTYSNERYAGVCDPDGCDFNSYRQGNKTFYGKGMTVDTTKKITVVTQFLKDANGD
 X17258 Mature   (226)   FTPHPCTIIGQSRCEGDSCGGTYSNERYAGVCDPDGCDFNSYRQGNKTFYGKGMTVDTTKKITVVTQFLKDANGD
      Consensus  (226)   FTPHPCTIIGQSRCEGDSCGGTYSNERYAGVCDPDGCDFNSYRQGNKTFYGKGMTVDTTKKITVVTQFLKDANGD 301                                                                      375
     CBS 225.63  (301)   LGEIKRFYVQDGKIIPNSESTIPGVEGNSITQDWCDRQKVAFGDIDDFNRKGGMKQMGKALAGPMVLVMSIWDDH
 D63515 Mature  (301)   LGEIKRFYVQDGKIIPNSESTIPGVEGNSITQDWCDRQKVAFGDIDDFNRKGGMKQMGKALAGPMVLVMSIWDDH
 X17258 Mature   (301)   LGEIKRFYVQDGKIIPNSESTIPGVEGNSITQDWCDRQKVAFGDIDDFNRKGGMKQMGKALAGPMVLVMSIWDDH
      Consensus  (301)   LGEIKRFYVQDGKIIPNSESTIPGVEGNSITQDWCDRQKVAFGDIDDFNRKGGMKQMGKALAGPMVLVMSIWDDH 376                                                                      450
     CBS 225.63  (376)   ASNMLWLDSTFPVDAAGKPGAERGACPTTSGVPAEVEAEAPNSNVVFSNIRFGPIGSTVAGLPGAGNGGNNGGNP
 D63515 Mature   (376)   ASNMLWLDSTFPVDAAGKPGAERGACPTTSGVPAEVEAEAPNSNVVFSNIRFGPIGSTVAGLPGAGNGGNNGGNP
 X17258 Mature   (376)   ASNMLWLDSTFPVDAAGKPGAERGACPTTSGVPAEVEAEAPNSNVVFSNIRFGPIGSTVAGLPGAGNGGNNGGNP
      Consensus  (376)   ASNMLWLDSTFPVDAAGKPGAERGACPTTSGVPAEVEAEAPNSNVVFSNIRFGPIGSTVAGLPGAGNGGNNGGNP 451                                                       507
     CBS 225.63  (451)   PPPTTTTSSAPATTTTASAGPKAGRWQQCGGIGFTGPTQCEEPYTCTKLNDWYSQCL
 D63515 Mature   (451)   PPPTTTTSSAPATTTTASAGPKAGRWQQCGGIGFTGPTQCEEPYTCTKLNDWYSQCL
 X17258 Mature   (451)   PPPTTTTSSAPATTTTASAGPKAGRWQQCGGIGFTGPTQCEEPYICTKLNDWYSQCL
      Consensus  (451)   PPPTTTTSSAPATTTTASAGPKAGRWQQCGGIGFTGPTQCEEPYTCTKLNDWYSQCL
```

FIG._5

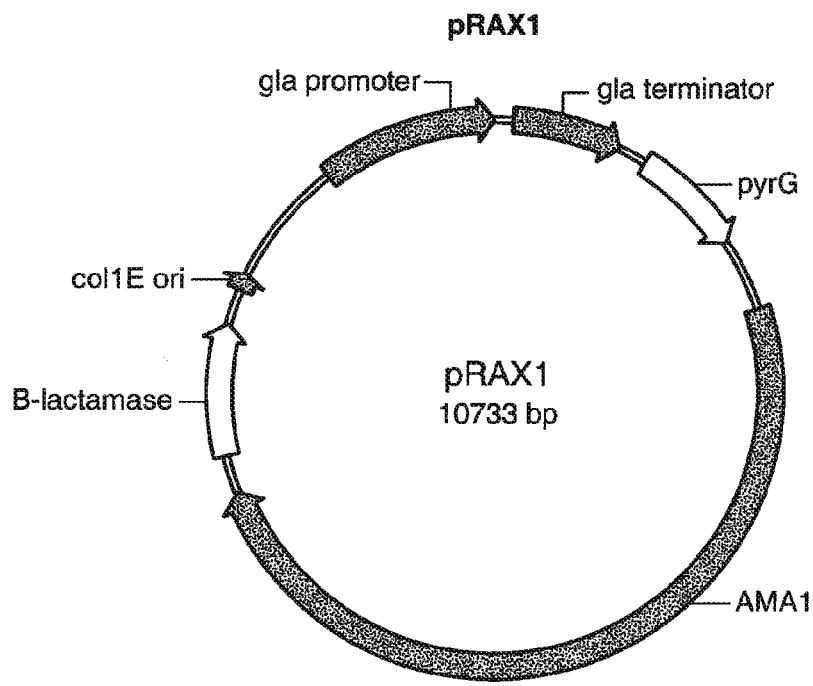
FIG._6
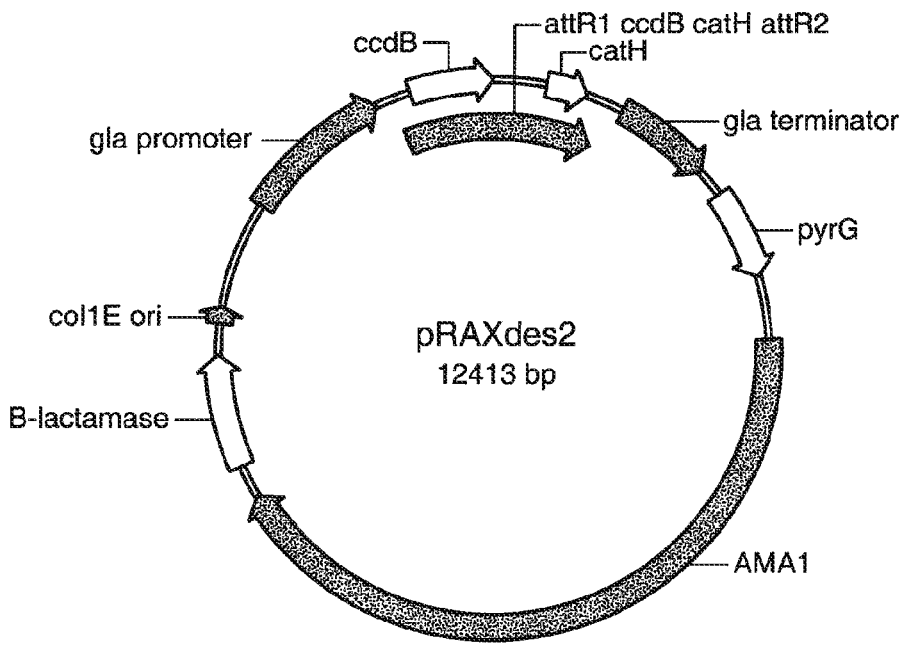
FIG._7

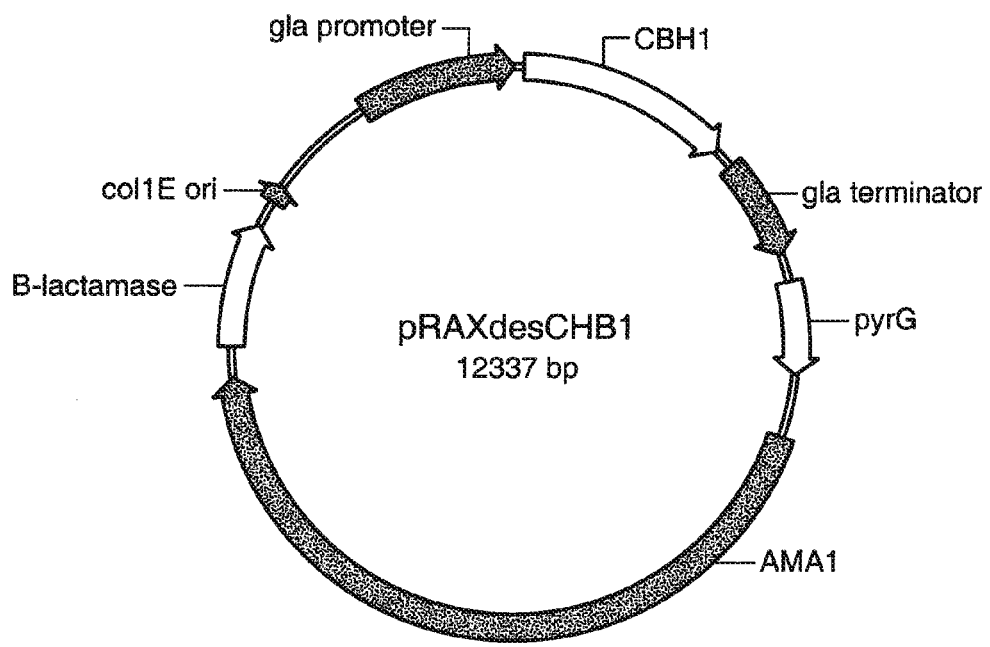
FIG._8

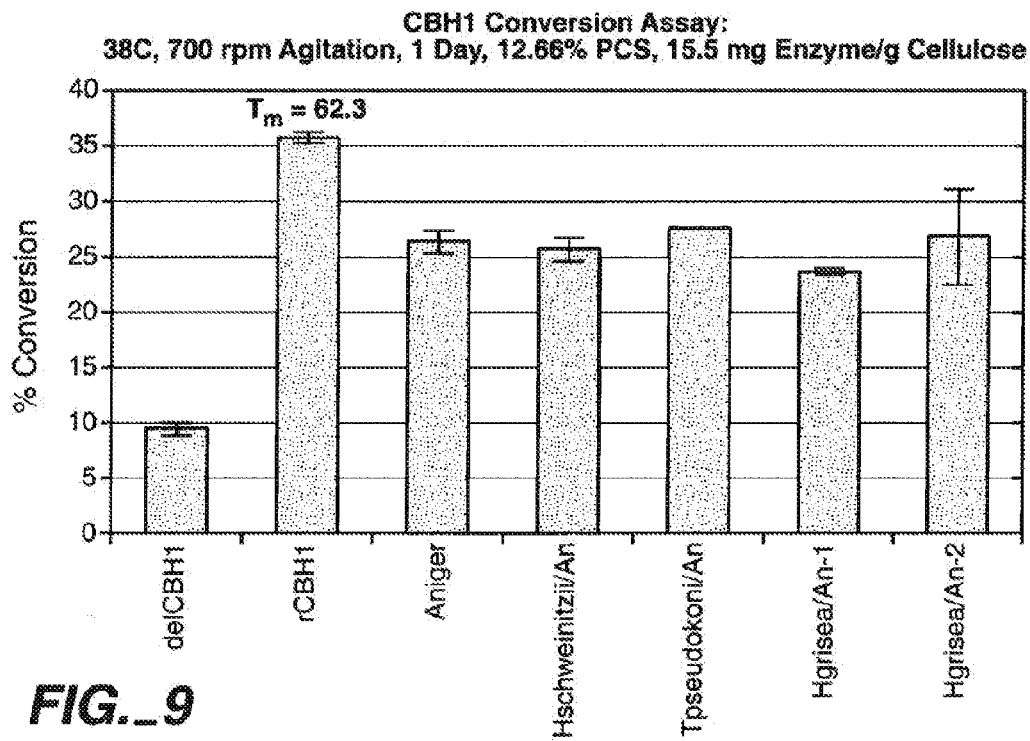
FIG._9
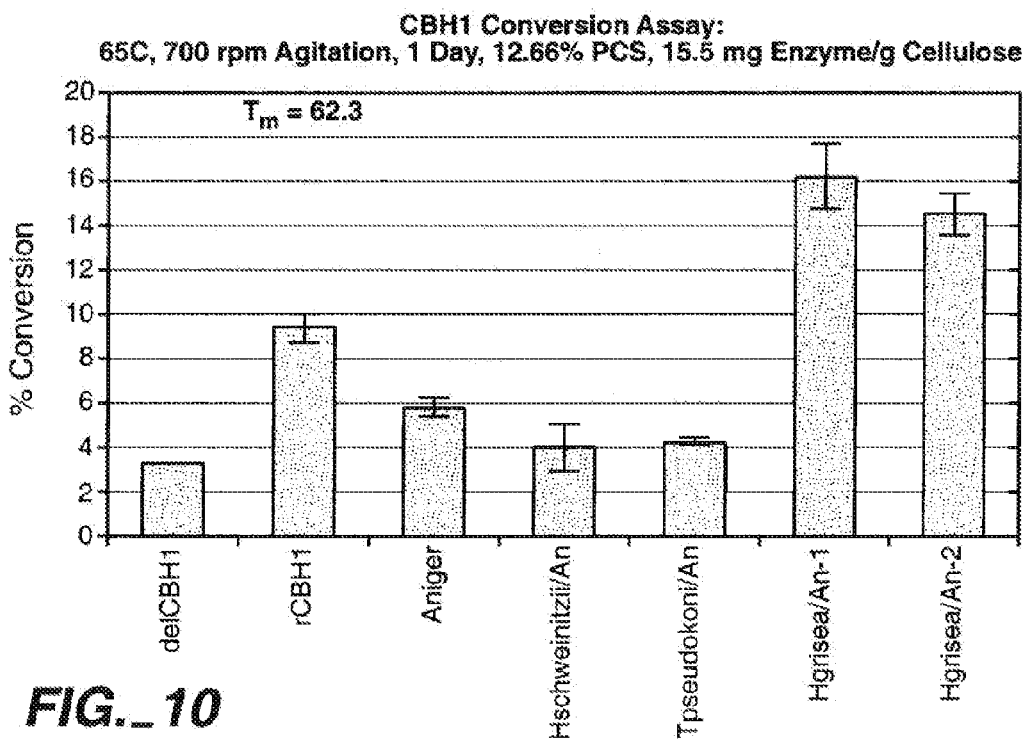
FIG._10

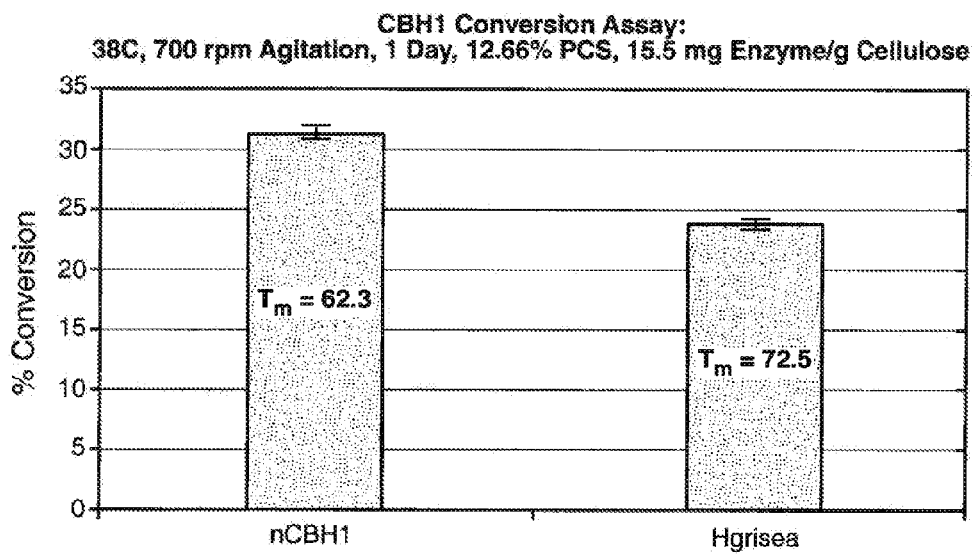
FIG._11
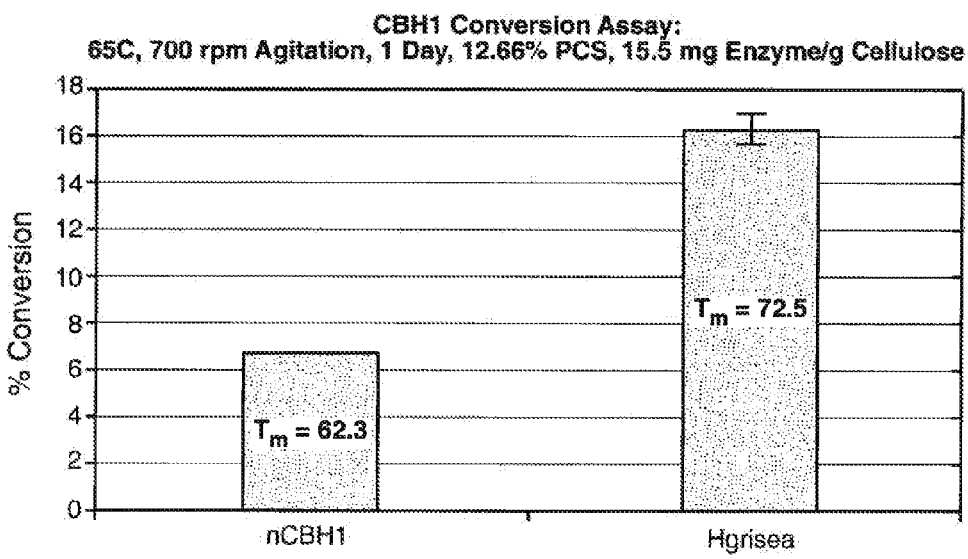
FIG._12

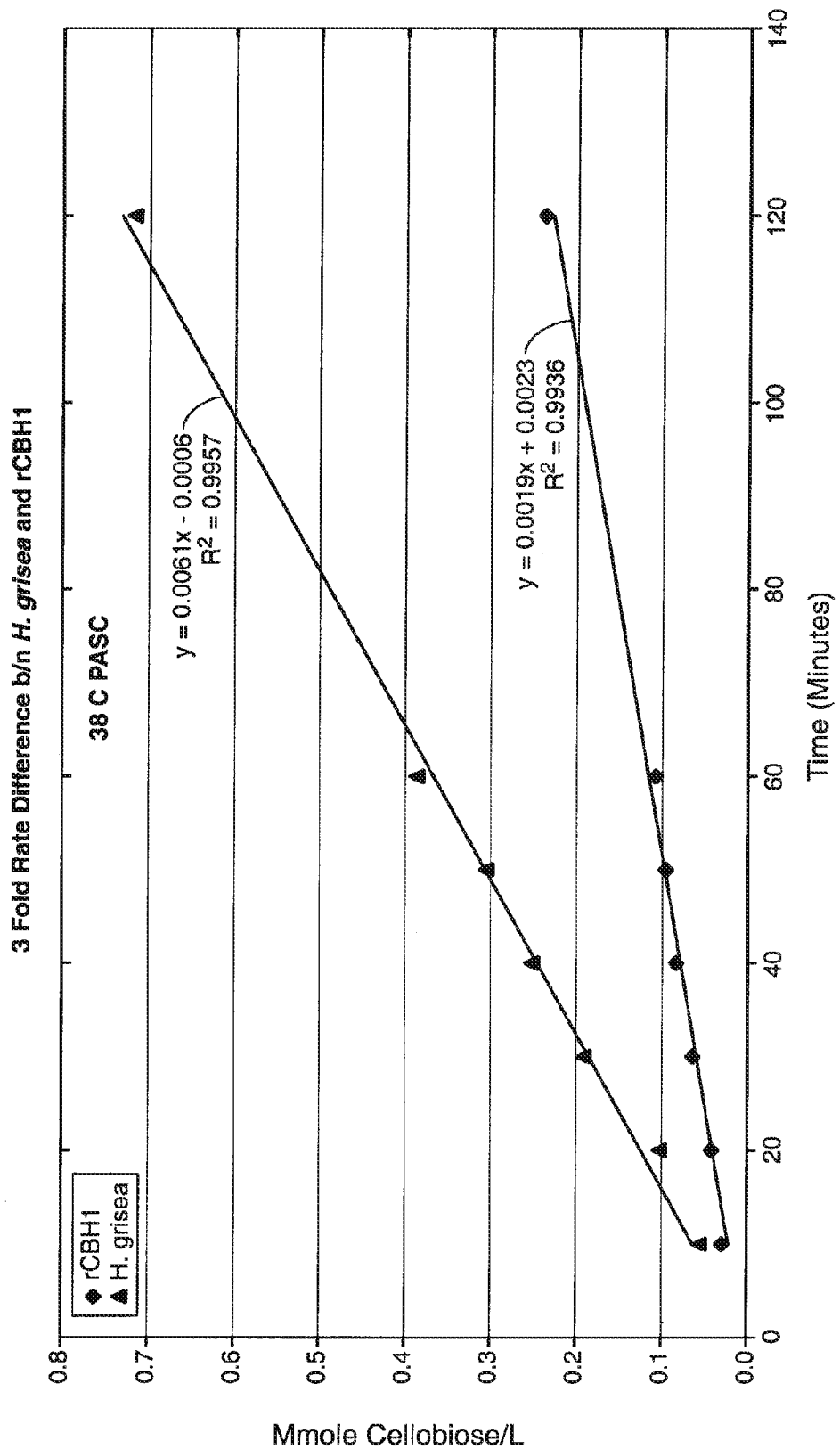
FIG._13A

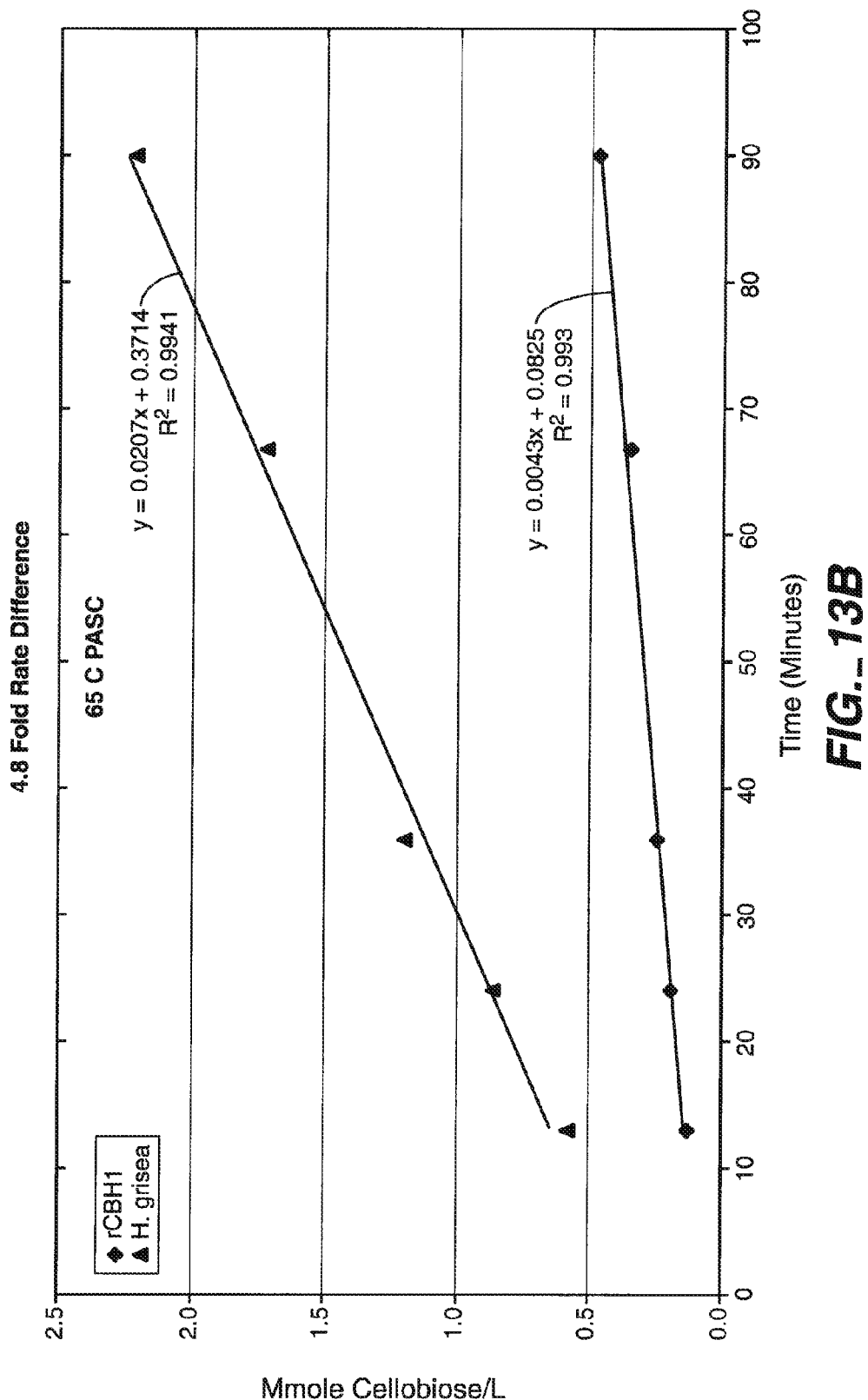
FIG._13B

Scytalidium thermophilium CBH1 Genomic DNA

```
   1  ATGCGTACCG CCAAGTTCGC CACCCTCGCC GCCCTTGTGG CCTCGGCCGC
  51  CGCCCAGCAG GCGTGCAGCC TCACCACCGA GAGGCACCCT TCCCTCTCCT
 101  GGAAGAAGTG CACCGCCGGC GGCCAGTGCC AGACCGTCCA GGCTTCCATC
 151  ACTCTCGACT CCAACTGGCG CTGGACTCAC CAGGTGTCTG CTCCACCAA
 201  CTGCTACACG GGCAACGAGT GGGATTCTAG CATCTGCACT GATGCCAAGT
 251  CGTGCGCTCA GAACTGCTGC GTCGATGGTG CTGACTACAC CAGCACCTAT
 301  GGCATCACCA CCAACGGTGA TTCCCTGAGC CTCAAGTTCG TCACCAAGGG
 351  CCAGTACTCG ACCAACGTCG GCTCGCGTAC CTACCTGATG GACGGCGAGG
 401  ACAAGTATCA GAGTAGGTTC TATCTTCAGC CTTCTCGCGC CTTGAATCCT
 451  GGCTAACTTT TACACTTCAC AGCCTTCGAG CTCCTCGGCA ACGAGTTCAC
 501  CTTCGATGTC GATGTCTCCA ACATCGGCTG CGGTCTCAAC GGCGCCCTGT
 551  ACTTCGTCTC CATGGACGCC GATGGTGGTC TCAGCCGCTA TCCTGGCAAC
 601  AAGGCTGGTG CCAAGTACGG TACCGGCTAC TGCGATGCTC AGTGCCCCCG
 651  TGACATCAAG TTCATCAACG GCGAGGCCAA CATTGAGGGC TGGACCGGCT
 701  CCACCAACGA CCCCAACGCC GGCGCGGGCC GCTATGGTAC CTGCTGCTCT
 751  GAGATGGATA TCTGGGAGGC CAACAACATG GCTACTGCCT TCACTCCTCA
 801  CCCTTGCACT ATCATTGGCC AGAGCCGCTG CGAGGGCGAC TCGTGCGGTG
 851  GCACCTACAG CAACGACCGC TACGCCGGCG TCTGCGACCC CGATGGCTGC
 901  GACTTCAACG CGTATCGCCA GGGCAACAAG ACCTTCTACG GCAAGGGCAT
 951  GACCGTCGAC ACCACCAAGA AGCTCACCGT CGTCACCCAG TTCCTCAAGG
1001  ACGCCAACGG CGATCTCGGC GAGATCAAGC GCTTCTACGT CCAGGATGGG
1051  AAGATCATCC CCAACTCCGA GTCCACCATC CCCGGCGTCG AGGGCAACTC
1101  CATCACCCAG GATTGGTGCG ACCGCCAGAA GGTTGCCTTT GGCGACATTG
1151  ACGACTTCAA CCGCAAGGGC GGCATGAAGC AGATGGGCAA GGCCCTCGCC
1201  GGCCCCATGG TCCTGGTCAT GTCCATCTGG GATGACCACG CCTCCAACAT
1251  GCTCTGGCTC GACTCGACCT TCCCTGTCGA TGCCGCTGGC AAGCCCGGCG
1301  CCGAGCGCGG TGCCTGCCCG ACCACCTCGG GTGTCCCTGC TGAGGTTGAG
1351  GCCGAGGCCC CCAACAGCAA CGTCGTCTTC TCCAACATCC GCTTCGGCCC
1401  CATCGGCTCG ACCGTTGCCG GCCTTCCCAG CGATGGCGGC AACAACGGCG
1451  GCAACACCAC CGTCCAGCCC CCGCCCAGCA CCACCACCAC CTCTGCCAGC
1501  AGCAGCACCA CCTCGGCTCC TGCCACCACC ACCACCGCCA GCGCTGGCCC
1551  CAAGGCTGGC CGCTGGCAGC AGTGCGGCGG CATCGGCTTC ACTGGCCCGA
1601  CCCAGTGCGA GGAGCCCTAC ACTTGCACCA AGCTCAACGA CTGGTACTCT
1651  CAGTGCCTGT AA
```

*FIG._14A*

Scytalidium thermophilium CBH1 cDNA

```
   1  ATGCGTACCG CCAAGTTCGC CACCCTCGCC GCCCTTGTGG CCTCGGCCGC
      CGCCCAGCAG GCGTGCAGCC TCACCACCGA GAGGCACCCT TCCCTCTCCT
 101  GGAAGAAGTG CACCGCCGGC GGCCAGTGCC AGACCGTCCA GGCTTCCATC
      ACTCTCGACT CCAACTGGCG CTGGACTCAC CAGGTGTCTG GCTCCACCAA
 201  CTGCTACACG GGCAACGAGT GGGATTCTAG CATCTGCACT GATGCCAAGT
      CGTGCGCTCA GAACTGCTGC GTCGATGGTG CTGACTACAC CAGCACCTAT
 301  GGCATCACCA CCAACGGTGA TTCCCTGAGC CTCAAGTTCG TCACCAAGGG
      CCAGTACTCG ACCAACGTCG GCTCGCGTAC CTACCTGATG GACGGCGAGG
 401  ACAAGTATCA GACCTTCGAG CTCCTCGGCA ACGAGTTCAC CTTCGATGTC
      GATGTCTCCA ACATCGGCTG CGGTCTCAAC GGCGCCCTGT ACTTCGTCTC
 501  CATGGACGCC GATGGTGGTC TCAGCCGCTA TCCTGGCAAC AAGGCTGGTG
      CCAAGTACGG TACCGGCTAC TGCGATGCTC AGTGCCCCCG TGACATCAAG
 601  TTCATCAACG GCGAGGCCAA CATTGAGGGC TGGACCGGCT CCACCAACGA
      CCCCAACGCC GGCGCGGGCC GCTATGGTAC CTGCTGCTCT GAGATGGATA
 701  TCTGGGAGGC CAACAACATG GCTACTGCCT TCACTCCTCA CCCTTGCACT
      ATCATTGGCC AGAGCCGCTG CGAGGGCGAC TCGTGCGGTG GCACCTACAG
 801  CAACGACCGC TACGCCGGCG TCTGCGACCC CGATGGCTGC GACTTCAACG
      CGTATCGCCA GGGCAACAAG ACCTTCTACG GCAAGGGCAT GACCGTCGAC
 901  ACCACCAAGA AGCTCACCGT CGTCACCCAG TTCCTCAAGG ACGCCAACGG
      CGATCTCGGC GAGATCAAGC GCTTCTACGT CCAGGATGGG AAGATCATCC
1001  CCAACTCCGA GTCCACCATC CCCGGCGTCG AGGGCAACTC CATCACCCAG
      GATTGGTGCG ACCGCCAGAA GGTTGCCTTT GGCGACATTG ACGACTTCAA
1101  CCGCAAGGGC GGCATGAAGC AGATGGGCAA GGCCCTCGCC GGCCCCATGG
      TCCTGGTCAT GTCCATCTGG GATGACCACG CCTCCAACAT GCTCTGGCTC
1201  GACTCGACCT TCCCTGTCGA TGCCGCTGGC AAGCCCGGCG CCGAGCGCGG
      TGCCTGCCCG ACCACCTCGG GTGTCCCTGC TGAGGTTGAG GCCGAGGCCC
1301  CCAACAGCAA CGTCGTCTTC TCCAACATCC GCTTCGGCCC CATCGGCTCG
      ACCGTTGCCG GCCTTCCCAG CGATGGCGGC AACAACGGCG GCAACACCAC
1401  CGTCCAGCCC CCGCCCAGCA CCACCACCAC CTCTGCCAGC AGCAGCACCA
      CCTCGGCTCC TGCCACCACC ACCACCGCCA GCGCTGGCCC CAAGGCTGGC
1501  CGCTGGCAGC AGTGCGGCGG CATCGGCTTC ACTGGCCCGA CCCAGTGCGA
      GGAGCCCTAC ACTTGCACCA AGCTCAACGA CTGGTACTCT CAGTGCCTGT
1601  AA
```

*FIG.—14B*

Scytalidium thermophilium CBH1, including Signal Sequence

```
  1  MRTAKFATLAALVASAAAQQACSLTTERHPSLSWKKCTAGGQCQTVQASI      50
 51  TLDSNWRWTHQVSGSTNCYTGNEWDSSICTDAKSCAQNCCVDGADYTSTY     100
101  GITTNGDSLSLKFVTKGQYSTNVGSRTYLMDGEDKYQTFELLGNEFTFDV     150
151  DVSNIGCGLNGALYFVSMDADGGLSRYPGNKAGAKYGTGYCDAQCPRDIK     200
201  FINGEANIEGWTGSTNDPNAGAGRYGTCCSEMDIWEANNMATAFTPHPCT     250
251  IIGQSRCEGDSCGGTYSNDRYAGVCDPDGCDFNAYRQGNKTFYGKGMTVD     300
301  TTKKLTVVTQFLKDANGDLGEIKRFYVQDGKIIPNSESTIPGVEGNSITQ     350
351  DWCDRQKVAFGDIDDFNRKGGMKQMGKALAGPMVLVMSIWDDHASNMLWL     400
401  DSTFPVDAAGKPGAERGACPTTSGVPAEVEAEAPNSNVVFSNIRFGPIGS     450
451  TVAGLPSDGGNNGGNTTVQPPPSTTTTSASSSTTSAPATTTTASAGPKAG     500
501  RWQQCGGIGFTGPTQCEEPYTCTKLNDWYSQCL-                     534
```

*FIG.—14C*

```
Genencor Hypocrea jecorina Cel7A    (1)    1                                                                           75
Humicola grisea CBH1.1              (1)    QSACTLQSETHPPLTWQKCSSGGTCTQQTGSVVIDANWRWTHATNSSTNCYDGNTWSSTLCPDNETCAKNCCLDG
Scytalidium thermophilum 69         (1)    QQACSLTTERHPSLSWNKCTAGGQCQTVQASITLDSNWRWTHQVSGSTNCYTGNKMDTSICTDAKSCAQNCCVDG
              Consensus             (1)    QQACSLTTERHPSLSWKKCTAGGQCQTVQASITLDSNWRWTHQVSGSTNCYTGNEWDSSICTDAKSCAQNCCVDG
                                           QQACSLTTERHPSLSWKKCTAGGQCQTVQASITLDSNWRWTHQVSGSTNCYTGNKWDSSICTDAKSCAQNCCVDG 76                                                                         150
Genencor Hypocrea jecorina Cel7A   (176)   AAYASTYGVTTSGNSLSIGFVTQSAQKN-VGARLYLMASDTTYQEFTLLGNEFSFDVDVSQLPCGLNGALYFVSM
Humicola grisea CBH1.1              (76)   ADYTSTYGITTNGDSLSLKFVTKGQHSTNVGSRTYLMDGEDKYQTFELLGNEFTFDVDVSNIGCGLNGALYFVSM
Scytalidium thermophilum 69         (76)   ADYTSTYGITTNGDSLSLKFVTKGQYSTNVGSRTYLMDGEDKYQTFELLGNEFTFDVDVSNIGCGLNGALYFVSM
              Consensus             (76)   ADYTSTYGITTNGDSLSLKFVTKGQHSTNVGSRTYLMDGEDKYQTFELLGNEFTFDVDVSNIGCGLNGALYFVSM 151                                                                        225
Genencor Hypocrea jecorina Cel7A   (150)   DADGGVSKYPTNTAGAKYGTGYCDSQCPRDLKFINGQANVEGWEPSSNNANTGIGGHGSCCSEMDIWEANSISEA
Humicola grisea CBH1.1             (151)   DADGGLSRYPGNKAGAKYGTGYCDAQCPRDIKFINGEANIEGWTGSTNDPNAGAGRYGTCCSEMDIWEANNMATA
Scytalidium thermophilum 69        (151)   DADGGLSRYPGNKAGAKYGTGYCDAQCPRDIKFINGEANIEGWTGSTNDPNAGAGRYGTCCSEMDIWEANNMATA
              Consensus            (151)   DADGGLSRYPGNKAGAKYGTGYCDAQCPRDIKFINGEANIEGWTGSTNDPNAGAGRYGTCCSEMDIWEANNMATA 226                                                                        300
Genencor Hypocrea jecorina Cel7A   (225)   LTPHPCTTVGQEICEGDGCGGTYSDNRYGGTCDPDGCDWNPYRLGNTSFYGPGSSFTLDTTKKLTVVTQFETSG-
Humicola grisea CBH1.1             (226)   FTPHPCTTIGQSRCEGDSCGGTYSNERYAGVCDPDGCDFNSYRQGNKTFYGKG--MTVDTTKKITVVTQFLKDAN
Scytalidium thermophilum 69        (226)   FTPHPCTTIGQSRCEGDSCGGTYSNERYAGVCDPDGCDFNAYRQGNKTFYGKG--MTVDTTKKLTVVTQFLKDAN
              Consensus            (226)   FTPHPCTTIGQSRCEGDSCGGTYSNERYAGVCDPDGCDFNSYRQGNKTFYGKG  MTVDTTKKITVVTQFLKDAN 301                                                                        375
Genencor Hypocrea jecorina Cel7A   (299)   ---AINRYYVQNGVTFQQPNAELGSYSGNELNDDYCTAEEAEFGGSS-FSDKGGLTQFKKATSGGMVLVMSLWD
Humicola grisea CBH1.1             (299)   GDLGEIKRFYVQDGKIIPNSESTIPGVEGNSITQDWCIDRQKVAFGDIDDFNRKGGMKQMGKALAGPMVLVMSIWD
Scytalidium thermophilum 69        (299)   GDLGEIKRFYVQDGKIIPNSESTIPGVEGNSITQDWCIDRQKVAFGDIDDFNRKGGMKQMGKALAGPMVLVMSIWD
              Consensus            (301)   GDLGEIKRFYVQDGKIIPNSESTIPGVEGNSITQDWCIDRQKVAFGDIDDFNRKGGMKQMGKALAGPMVLVMSIWD 376                                                                        450
Genencor Hypocrea jecorina Cel7A   (369)   DYYANMLWLDSTYPTNETSSTPGAVRGSCSTSSGVPAQVESQSPNAKVTFSNIKFGPIGSTGNPSGGNP------
Humicola grisea CBH1.1             (374)   DHASNMLWLDSTFPVDAAG-KPGAERGACPTTSGVPAEVEAEAPNSNVVFSNIRFGPIGSTVAGLPGAG---NGGN
Scytalidium thermophilum 69        (374)   DHASNMLWLDSTFPVDAAG-KPGAERGACPTTSGVPAEVEAEAPNSNVVFSNIRFGPIGSTVAGLPSDGGNNGGN
              Consensus            (376)   DHASNMLWLDSTFPVDAAG  KPGAERGACPTTSGVPAEVEAEAPNSNVVFSNIRFGPIGSTVAGLPGAG  NGGN 451                                              518
Genencor Hypocrea jecorina Cel7A   (438)   PGGNPPG-------TTTTRRPATTTGSSPGPTQSHYGQCGGIGYSGPTVCASGTTCQVLNPYYSQCL
Humicola grisea CBH1.1             (446)   NGGNPPP-------PTTTTSSAPATTTASAGPKAGRWQQCGGIGFTGPTQCEEPYICTKLNDWYSQCL
Scytalidium thermophilum 69        (448)   TTVQPPSTTTTSASSSTTSAFATTTASAGPKAGRWQQCGGIGFTGPTQCEEPYTCTKLNDWYSQCL
              Consensus            (451)   NGGNPPP   PTTTTSSAPATTTASAGPKAGRWQQCGGIGFTGPTQCEEPYTCTKLNDWYSQCL
```

Alignment of the Mature Protein Sequences for *Hypocrea jecorina* CBHI, *Humicola grisea* var. *thermoidea* CBH1.1, and *Scytalidium thermophilum* CBH

FIG. _ 15

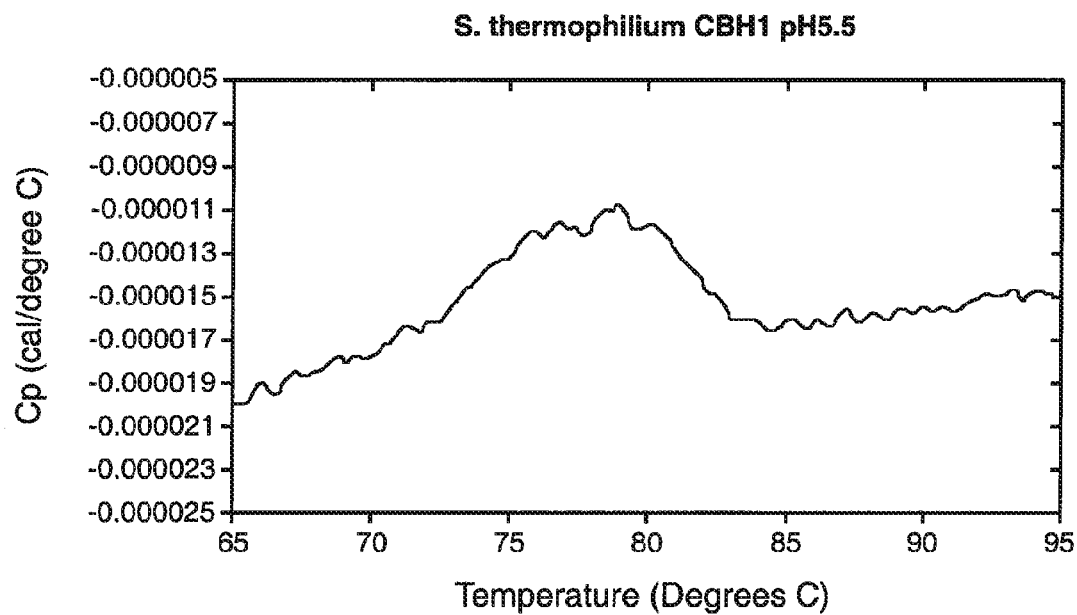
FIG. _16A
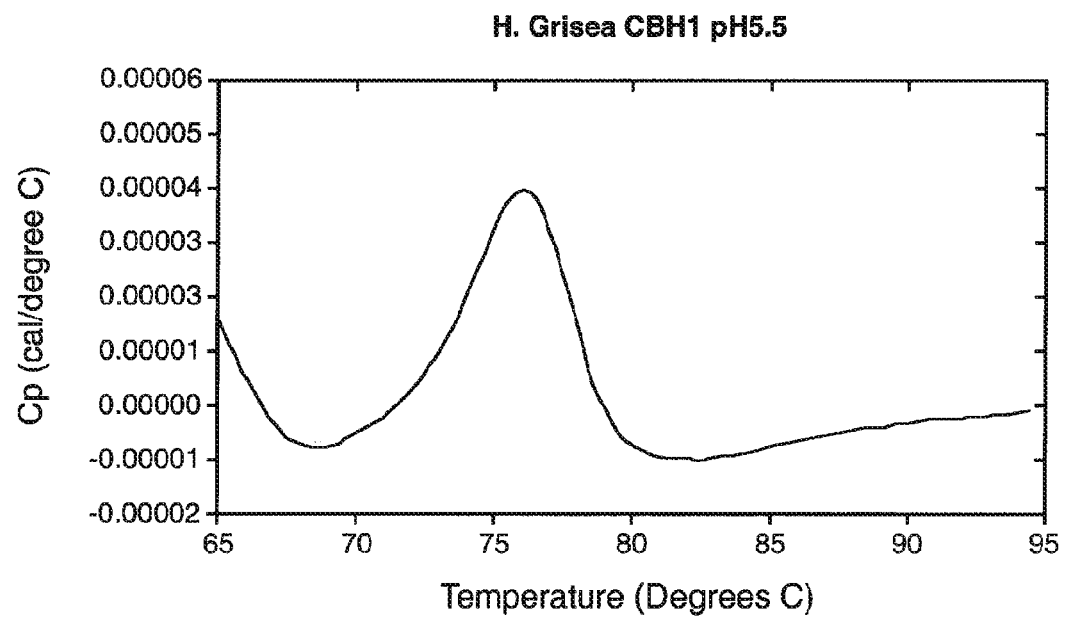
FIG. _16B

VARIANT *HUMICOLA GRISEA* CBH1.1

CROSS-REFERENCE TO RELATED APPLICATIONS

This application is a divisional of U.S. application Ser. No. 13/744,316, filed Jan. 17, 2013, now U.S. Pat. No. 8,828,702, which is a divisional of U.S. application Ser. No. 13/092,086, filed Apr. 21, 2011, now U.S. Pat. No. 8,377,659, which is a divisional of U.S. application Ser. No. 11/825,498, filed Jul. 6, 2007, now U.S. Pat. No. 7,998,711, which is a continuation of U.S. application Ser. No. 10/810,277, filed Mar. 26, 2004, now U.S. Pat. No. 7,459,299, which claims priority to the benefit of U.S. Provisional Application No. 60/459,734, filed Apr. 1, 2003, each of which is herein incorporated by reference.

STATEMENT AS TO RIGHTS TO INVENTIONS MADE UNDER FEDERALLY SPONSORED RESEARCH AND DEVELOPMENT

Portions of this work were funded by Subcontract No. ZCO-0-30017-01 with the National Renewable Energy Laboratory under Prime Contract No. DE-AC36-99GO10337 with the U.S. Department of Energy. Accordingly, the United States Government may have certain rights in this invention.

FIELD OF THE INVENTION

The present invention relates to polypeptides having cellobiohydrolase I (also referred to as CBH I or CBH1) activity and polynucleotides having a nucleotide sequence which encodes for the polypeptides. The invention also relates to nucleic acid constructs, vectors, and host cells comprising the nucleic acid constructs as well as methods for producing and using the polypeptides.

BACKGROUND OF THE INVENTION

Cellulose is an important industrial raw material and a source of renewable energy. The physical structure and morphology of native cellulose are complex and the fine details of its structure have been difficult to determine experimentally. However, the chemical composition of cellulose is simple, consisting of D-glucose residues linked by beta-1 4-glycosidic bonds to form linear chains.

In order to be efficient, the digestion of cellulose requires several types of enzymes acting cooperatively. At least three categories of enzymes are necessary to convert cellulose into glucose: endo (1,4)-beta-D-glucanases (EC 3 1.4) that cut the cellulose chains at random; cellobiohydrolases (EC 3 1.91) which cleave cellobiosyl units from the cellulose chain ends and beta-glucosidases (EC 3 1.21) that convert cellobiose and soluble cellodextrins into glucose. Among these three categories of enzymes involved in the biodegradation of cellulose, cellobiohydrolases are the key enzymes for the degradation of native crystalline cellulose.

Exo-cellobiohydrolases (Cellobiohydrolase 1, or CBH 1) refer to the cellobiohydrolases which degrade cellulose by hydrolyzing the cellobiose from the non-reducing end of the cellulose polymer chains.

It is an object of the present invention to provide improved polypeptides having cellobiohydrolase I activity and polynucleotides encoding the polypeptides. The improved polypeptides may have improved specific activity and/or improved stability—in particular improved thermostability.

Although cellulase compositions have been previously described, there remains a need for new and improved cellulase compositions for use in household detergents, stonewashing compositions or laundry detergents, etc. Cellulases that exhibit improved performance are of particular interest.

REFERENCES

Altschul, S. F., et al., J. Mol. Biol. 215:403-410, 1990.
Altschul, S. F., et al., Nucleic Acids Res. 25:3389-3402, 1997.
Aro, N., et al., J. Biol. Chem., 10.1074/M003624200, Apr. 13, 2001.
Aubert, et al., Ed., p 11 et seq., Academic Press, 1988.
Ausubel G. M., et al. CURRENT PROTOCOLS IN MOLECULAR BIOLOGY, John Wiley & Sons, New York, N.Y., 1993.
Baker et al., Appl. Biochem. and Biotechnol. 45/46:245-256, 1994.
Bhikhabhai, R. et al., J. Appl. Biochem. 6:336, 1984.
Boel et al. EMBO J. 3:1581-1585 1984.
Brumbauer, A. et al., Bioseparation 7:287-295, 1999.
Deutscher, M. P., Methods Enzymol. 182:779-80, 1990.
Ellouz, S. et al., J. Chromatography 396:307, 1987.
Filho, et al. Can. J. Microbiol. 42:1-5, 1996.
Fliess, A., et al., Eur. J. Appl. Microbiol. Biotechnol. 17:314, 1983.
Goedegebuur et al., Curr. Genet. 41:89-98, 2002.
Goyal, A. et al. Bioresource Technol. 36:37, 1991.
Hazell, B. W. et al., Lett. Appl. Microbiol. 30:282-286, 2000.
Herr et al., Appl. Microbiol. Biotechnol. 5:29-36, 1978.
Hu et al., Mol. Cell. Biol. 11:5792-9, 1991.
Jeeves et al., Biotechnol. Genet. Eng. Rev. 9:327-369, 1991.
Kawaguchi, T et al., Gene 173(2):287-8, 1996.
Kelley et al. EMBO J. 4:475-479, 1985.
Knowles, J. et al., TIBTECH 5, 255-261, 1987.
Krishna, S. et al., Bioresource Tech. 77:193-196, 2001.
Kuhls K. et al., Proc. Natl. Acad. Sci. USA 93(15): 7755-7760, 1996.
Kumar, A., et al., Textile Chemist and Colorist 29:37-42, 1997.
Medve, J. et al., J. Chromatography A 808:153, 1998.
Mohagheghi, A. et al., Int. J. Syst. Bacteriol. 36:435-443, 1986.
Nieves et al., Appl. Biochem. and Biotechnol. 51/52 211-223, 1995.
Nunberg et al. Mol. Cell. Biol. 4:2306-2315 1984.
Ohmiya et al., Biotechnol. Gen. Engineer. Rev. 14:365-414, 1997.
Okada, M. et al., Appl. Environ. Microbiol., 64:555-563, 1988.
Ooi et al., Nucleic Acid Res. 18:5884, 1990
Penttila et al., Gene 45:253-263, 1986.
Penttila et al., Gene 61: 155-164, 1987.
Penttila et al., Gene 63: 103-112, 1988.
Pere, J., et al., In Proc. Tappi Pulping Conf., Nashville, Tenn., 27-31, pp. 693-696, 1996.
Saarilahti et al., Gene 90:9-14, 1990.
Sakamoto et al., Curr. Genet. 27:435-439, 1995.
Saloheimo M, et al., Gene 63:11-22, 1988.
Saloheimo, A. et al., Molecular Microbiology, 13:219-228, 1994.
Saloheimo, M. et al., Eur. J. Biochem., 249:584-591, 1997.

Sambrook et al., MOLECULAR CLONING: A LABORATORY MANUAL (Second Edition), Cold Spring Harbor Press, Plainview, N.Y., 1989.
Schulein, Methods Enzymol., 160, 25, pages 234 et seq, 1988.
Scopes, Methods Enzymol. 90 Pt E:479-90, 1982.
Shoemaker et al., Biochem. Biophys. Acat. 523:133-146 1978.
Shoemaker, S. et al., Bio/Technology, 1:691-696, 1983
Srisodsuk, M. et al. J. Biol. Chem. 268(28): 20756-20761, 1993.
Strathern et al., eds. (1981) The Molecular Biology of the Yeast *Saccharomyces*.
Suurnakki, A. et al., Cellulose 7:189-209, 2000.
Teeri, T. et al., Gene, 51:43-52, 1987
Tilbeurgh, H. et al., FEBS Lett. 16:215, 1984.
Tomaz, C. and Queiroz, J., J. Chromatography A 865:123-128, 1999.
Tomme, P. et al., Eur. J. Biochem. 170:575-581, 1988.
Van Tilbeurgh, H. et al., FEBS Lett. 204:223-227, 1986.
Ward, M. et al., Appl. Microbiol. Biotechnol. 39:738-743, 1993.
Wood, Biochem. Soc. Trans., 13, pp. 407-410, 1985.
Wood et al., METHODS IN ENZYMOLOGY, 160, 25, p. 87 et seq., Academic Press, New York, 1988.

BRIEF SUMMARY OF THE INVENTION

In a first aspect, the present invention relates to a polypeptide having cellobiohydrolase I activity, selected from the group consisting of
a) *H. grisea* CBH1.1 variant derived from CBS 225.63
b) *H. grisea* CBH1.1 variant having the sequence given in FIG. 3
c) *H. grisea* CBH1.1 variant having the sequence given in FIG. 4
d) *Hypocrea jecorina* CBH1 variant as described herein; and
e) *Scytalidium thermophilium* CBH1 derived from CBS 671.88.

In second aspect the present invention relates to a polynucleotide encoding an *H. grisea* CBH1.1 variant, a *H. jecorina* CBH1 variant or a *S. thermophilium* CBH1. In one embodiment, the polynucleotide encodes an *H. grisea* CBH1.1 variant is derived from CBS 225.63. In another embodiment, the polynucleotide encodes an *H. grisea* CBH1.1 variant shown in FIG. 3. In another embodiment, the polynucleotide encodes an *H. grisea* CBH1.1 variant shown in FIG. 4.

In one general embodiment, polynucleotide encoding an *H. grisea* CBH1.1 variant, a *H. jecorina* CBH1 variant or a *S. thermophilium* CBH1 has at least 90%, preferably 95%, 98%, or more sequence identity to the *H. grisea* CBH1.1 variant, a *H. jecorina* CBH1 variant or a *S. thermophilium* CBH1 coding sequences presented herein using a sequence alignment program.

In a third aspect the present invention relates to a nucleic acid construct comprising the nucleotide sequence, which encodes for the inventive CBH1.1 variant, a *H. jecorina* CBH1 variant or a *S. thermophilium* CBH1, operably linked to one or more control sequences that direct the production of the CBH1.1 variant, *H. jecorina* CBH1 variant or *S. thermophilium* CBH1 in a suitable host.

In a fourth aspect the present invention relates to a recombinant expression vector comprising the nucleic acid construct of the invention.

In a fifth aspect the present invention relates to a recombinant host cell comprising the nucleic acid construct of the invention.

In a sixth aspect the present invention relates to a method for producing a CBH1, the method comprising
a) transforming a host cell with a nucleic acid encoding a *H. grisea* CBH1.1 variant, a *H. jecorina* CBH1 variant or a *S. thermophilium* CBH1 described herein;
b) culturing the host cell under conditions to produce the polypeptide; and
c) recovering the polypeptide.

BRIEF DESCRIPTION OF THE DRAWINGS

FIG. 1 is the genomic DNA sequence for *H. grisea* CBH1.1 (SEQ ID NO:1). The putative intron is in bold and underlined.

FIG. 2 is the cDNA sequence for *H. grisea* CBH1.1 (SEQ ID NO:2). The putative intron sequence (nucleotides 413-472 in FIG. 1) has been deleted.

FIG. 3 is the signal sequence and mature amino acid sequence for *H. grisea* CBH1.1 (SEQ ID NO:3). The signal sequence is in bold and underlined.

FIG. 4 is the mature amino acid sequence for *H. grisea* CBH1.1 (SEQ ID NO:4).

FIG. 5 shows an alignment of two public and a variant *Humicola grisea* CBH1.1 mature sequences. The two public sequences are X17258 (SEQ ID NO:5) and D63515 (SEQ ID NO:6).

FIG. 6 is the pRAX1 plasmid. This vector is based on the plasmid pGAPT2 except a 5259 bp HindIII fragment of *Aspergillus nidulans* genomic DNA fragment AMA1 sequence (Molecular Microbiology 1996 19:565-574) was inserted. Base 1 to 1134 contains *Aspergillus niger* glucoamylase gene promoter. Base 3098 to 3356 and 4950 to 4971 contains *Aspergillus niger* glucoamylase terminator. *Aspergillus nidulans* pyrG gene was inserted from 3357 to 4949 as a marker for fungal transformation. There is a multiple cloning site (MCS) into which genes may be inserted.

FIG. 7 is the pRAXdes2 vector backbone. This vector is based on the plasmid vector pRAX1. A Gateway cassette has been inserted into pRAX1 vector (indicated by the arrow on the interior of the circular plasmid). This cassette contains recombination sequence attR1 and attR2 and the selection marker catH and ccdB. The vector has been made according to the manual given in Gateway™ Cloning Technology: version 1 page 34-38 and can only replicate in *E. coli* DB3.1 from Invitrogen; in other *E. coli* hosts the ccdB gene is lethal. First a PCR fragment is made with primers containing attB½ recombination sequences. This fragment is recombined with pDONR201 (commercially available from Invitrogen); this vector contains attP½ recombination sequences with catH and ccdB in between the recombination sites. The BP clonase enzymes from Invitrogen are used to recombine the PCR fragment in this so-called ENTRY vector, clones with the PCR fragment inserted can be selected at 50 µg/ml kanamycin because clones expressing ccdB do not survive. Now the att sequences are altered and called attL1 and attL2. The second step is to recombine this clone with the pRAXdes2 vector (containing attR1 and attR2 catH and ccdB in between the recombination sites). The LR clonase enzymes from Invitrogen are used to recombine the insert from the ENTRY vector in the destination vector. Only pRAXCBH1 vectors are selected using 100 µg/ml ampicillin because ccdB is lethal and the ENTRY vector is sensitive to ampicillin. By this method the expression vector is now prepared and can be used to transform *A. niger*. The *H. grisea* CBH1.1 expression is under the *Aspergillus* glucoamylase promoter and terminator control. The transformation marker pyrG gene and the AMA 1 sequence are from *Aspergillus nidulans*.

FIG. 8 provides an illustration of the pRAXdes2cbh1 vector which was used for expression of the nucleic acids encoding the CBH1.1 variants in *Aspergillus*. A nucleic acid encoding a CBH1.1 enzyme variant was cloned into the vector by homologous recombination of the att sequences.

FIG. 9 illustrates the activity of various CBH1 cellulases in a cellulose conversion assay at one day, 38° C., and 15 mg of total enzyme/g cellulose using pretreated corn stover (PCS) as a substrate. This assay combines at about a 50:50 mass ratio the CBH1.1 sample to be tested with supernatant from growths of a *T. reesei* strain which has been deleted for CBH1. At 38° C. the *H grisea* CBH1.1 is unremarkable in this assay.

Figure 13C:
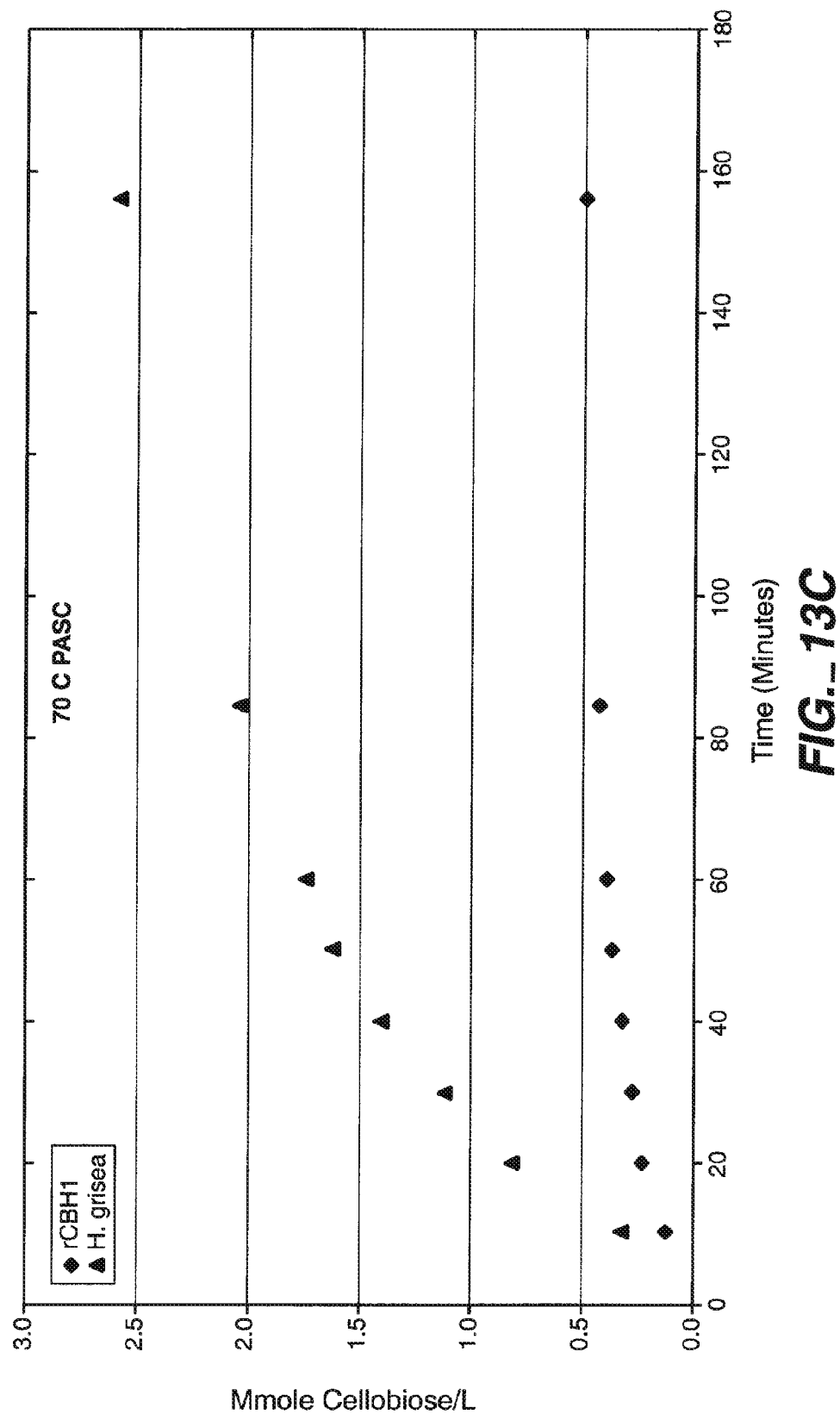

Legend: delCBHI is a strain that has had its endogenous CBH1 deleted; it is CBH1 deficient. rCBH1 is a purified enzyme from an *A. niger* strain that has had a *T. reesei* CBH1 gene inserted. *A. niger* is a purified CBHB from an *A. niger* strain overexpressing its endogenous cellulase CBHB. Hschweinitzii/An is a purified CBH1 from an *A. niger* strain expressing an inserted heterologous CBH1 gene from *Hypocrea schweinitzii*. Tpseudokoni/An is a purified CBH1 from an *A. niger* strain expressing an inserted heterologous CBH1 gene from *Trichoderma pseudokoningii*. Hgrisea/An-1 is a purified CBH1.1 from a first *A. niger* clone expressing an inserted heterologous CBH1.1 gene from *H. grisea*. Hgrisea/An-2 is a purified CBH1.1 from a second *A. niger* clone expressing an inserted heterologous CBH1.1 gene from *H. grisea*. Hgrisea/An-1 and Hgrisea/An-2 are two clones from the same transformation of *A. niger* with the *H. grisea* variant CBH1.1 gene.

FIG. 10 shows the activity CBHI cellulases in a cellulose conversion assay at one day, 65° C., and 15 mg of total enzyme/g cellulose using pretreated corn stover as a substrate. This assay combines at about a 50:50 mass ratio the CBHI sample to be tested with supernatant from growths of a *T. reesei* strain which has been deleted for CBHI. Unlike the 38° C. result both *H grisea* CBH1.1 samples are clearly better than other samples. Legend: same as for FIG. 9.

FIG. 11 illustrates the activity of *H. grisea* CBH1.1 and *T. reesei* CBH1 cellulases in a cellulose conversion assay at one day, 38° C., and 15 mg of total enzyme/g cellulose using pretreated corn stover (PCS) as a substrate. This assay combines at about a 50:50 mass ratio the CBH1.1 sample to be tested with supernatant from the growth of a *T. reesei* strain which has been deleted for CBH1. At 38° C. the *H grisea* CBH1.1 is unremarkable in this assay. Native CBH1 (nCBH1) was purified from a *T. reesei* whole cellulase using methods known in the art (see Methods for Purifying CBH, below).

FIG. 12 shows the activity results for the *H. grisea* and *T. reesei* rCBH1 enzymes only in a cellulose conversion assay at one day, 65° C., and 15 mg of total enzyme/g cellulose using pretreated corn stover as a substrate. This assay combines at about a 50:50 mass ratio the CBHI sample to be tested with supernatant from the growth of a *T. reesei* strain which has been deleted for CBHI. Unlike the 38° C. result the *H grisea* CBH1.1 sample are is better than *T. reesei*.

FIG. 13A-C shows the activity CBHI cellulases in a cellulose conversion assay on Phosphoric acid swollen cellulose (PASC) at various time points. In panel A, the temperature is 38° C. with measurements being taken over a period of 120 minutes. In panel B, measurements were taken at the temperature 65° C. In panel C, measurements were taken at the temperature 70° C. It can be seen that the variant *H. grisea* CBH1.1 releases more cellobiose than the *T. reesei* CBH1 at any time point measured.

FIG. 14A-14C shows the genomic DNA (SEQ ID NO:7), the cDNA (SEQ ID NO:8) and amino acid (SEQ ID NO:9) sequences of the *Scytalidium thermophilium* CBH1. The amino acid sequence includes the signal sequence.

FIG. 15 shows the alignment of the mature forms (i.e., without a signal sequence) of *H. grisea* CBH 1.1, *H. jecorina* CBH1 (SEQ ID NO: 10) and *Scytalidium thermophilium* CBH1 (SEQ ID NO:11). Also shown is the consensus sequence (SEQ ID NO:12). Six residues in the *H. jecorina* CBH1 catalytic domain are bold and underlined indicating the sites may be important for enhanced stability.

FIGS. 16A and B show the thermostability profiles for *H. grisea* CBH1.1 and *S. thermophilium* CBH1.

DETAILED DESCRIPTION

The invention will now be described in detail by way of reference only using the following definitions and examples. All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acids are written left to right in 5' to 3' orientation; amino acid sequences are written left to right in amino to carboxy orientation, respectively. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

The headings provided herein are not limitations of the various aspects or embodiments of the invention which can be had by reference to the specification as a whole. Accordingly, the terms defined immediately below are more fully defined by reference to the specification as a whole.

All publications cited herein are expressly incorporated herein by reference for the purpose of describing and disclosing compositions and methodologies which might be used in connection with the invention.

I. DEFINITIONS

"Cellulase," "cellulolytic enzymes" or "cellulase enzymes" means bacterial, or fungal exoglucanases or exo-cellobiohydrolases, and/or endoglucanases, and/or β-glucosidases.

The term "cellulase" refers to a category of enzymes capable of hydrolyzing cellulose polymers to shorter cello-oligosaccharide oligomers, cellobiose and/or glucose. Numerous examples of cellulases, such as exoglucanases, exocellobiohydrolases, endoglucanases, and glucosidases have been obtained from cellulolytic organisms, particularly including fungi, and bacteria. The enzymes made by these microbes are mixtures of proteins with three types of actions useful in the conversion of cellulose to glucose: endoglucanases (EG), cellobiohydrolases (CBH), and beta-glucosidase. These three different types of cellulase enzymes act synergistically to convert cellulose and its derivatives to glucose.

Many microbes make enzymes that hydrolyze cellulose, including the fungus *Trichoderma*, the compost bacteria *Thermomonospora, Bacillus*, and *Cellulomonas; Streptomyces*; and the fungi *Humicola, Aspergillus* and *Fusarium*.

"Cellobiohydrolase 1 activity" means a cellulose 1,4-beta-cellobiosidase (also called Exo-glucanase, Exo-cellobiohydrolase, CBH1 or 1,4-beta-cellobiohydrolase) activity, as defined in the enzyme class EC3.2.1.91 which catalyzes the hydrolysis of 1,4-beta-D-glucosidic linkages in cellulose and cellotetraose, releasing cellobiose from the non-reducing ends of the cellulose chains. For the present invention, the CBH1 activity may be determined according to the procedure described in Example 4.

By the term "host cell" is meant a cell that contains a vector and supports the replication, and/or transcription or transcription and translation (expression) of the expression construct. Host cells for use in the present invention can be prokaryotic cells, such as *E. coli*, or eukaryotic cells such as yeast, plant, insect, amphibian, or mammalian cells. In general, host cells are filamentous fungi.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "secretory signal sequence" denotes a DNA sequence that encodes a polypeptide (a "secretory peptide" or "secretory signal peptide") that, as a component of a larger polypeptide, directs the larger polypeptide through a secretory pathway of a cell in which it is synthesized. The larger peptide is commonly cleaved to remove the secretory peptide during transit through the secretory pathway to yield the secretory signal peptide and a smaller peptide commonly referred to as the mature polypeptide.

As used herein, the phrases "whole cellulase preparation" and "whole cellulase composition" are used interchangeably and refer to both naturally occurring and non-naturally occurring compositions. A "naturally occurring" composition is one produced by a naturally occurring source and which comprises one or more cellobiohydrolase-type, one or more endoglucanase-type, and one or more β-glucosidase components wherein each of these components is found at the ratio produced by the source. A naturally occurring composition is one that is produced by an organism unmodified with respect to the cellulolytic enzymes such that the ratio of the component enzymes is unaltered from that produced by the native organism.

A "non-naturally occurring" composition encompasses those compositions produced by: (1) combining component cellulolytic enzymes either in a naturally occurring ratio or non-naturally occurring, i.e., altered, ratio; or (2) modifying an organism to overexpress or underexpress one or more cellulolytic enzyme; or (3) modifying an organism such that at least one cellulolytic enzyme is deleted or (4) modifying an organism to express a heterologous component cellulolytic enzyme.

As used herein, the term "promoter" refers to a nucleic acid sequence that functions to direct transcription of a downstream gene. The promoter will generally be appropriate to the host cell in which the target gene is being expressed. The promoter together with other transcriptional and translational regulatory nucleic acid sequences (also termed "control sequences") are necessary to express a given gene. In general, the transcriptional and translational regulatory sequences include, but are not limited to, promoter sequences, ribosomal binding sites, transcriptional start and stop sequences, translational start and stop sequences, and enhancer or activator sequences. The promoter may be the promoter normally associated with the downstream gene or it may be heterologous, i.e., from another gene or another microorganism as long as it function to direct the gene. In one aspect the promoter is an inducible promoter. In one aspect the promoter is the *T. reesei* cbh1 promoter which is deposited in GenBank under Accession Number D86235. In another aspect the promoter is a cbh II or xylanase promoter from *T. reesei*.

Examples include the promoter from the *A. awamori* or *A. niger* glucoamylase genes (Nunberg, J. H. et al. (1984) Mol. Cell. Biol. 4, 2306-2315; Boel, E. et al. (1984) EMBO J. 3, 1581-1585), the *Mucor miehei* carboxyl protease gene herein, the *Trichoderma reesei* cellobiohydrolase I gene (Shoemaker, S. P. et al. (1984) European Patent Application No. EPO0137280A1), the *A. nidulans* trpC gene (Yelton, M. et al. (1984) Proc. Natl. Acad. Sci. USA 81, 1470-1474; Mullaney, E. J. et al. (1985) Mol. Gen. Genet. 199, 37-45) the *A. nidulans* alcA gene (Lockington, R. A. et al. (1986) Gene 33, 137-149), the *A. nidulans* tpiA gene (McKnight, G. L. et al. (1986) Cell 46, 143-147), the *A. nidulans* amdS gene (Hynes, M. J. et al. (1983) Mol. Cell. Biol. 3, 1430-1439), the *T. reesei* xln1 gene, the *T. reesei* cbh2 gene, the *T. reesei* egl1 gene, the *T. reesei* egl2 gene, the *T. reesei* egl3 gene, and higher eukaryotic promoters such as the SV40 early promoter (Barclay, S. L. and E. Meller (1983) Molecular and Cellular Biology 3, 2117-2130).

A nucleic acid is "operably linked" when it is placed into a functional relationship with another nucleic acid sequence. For example, DNA encoding a secretory leader, i.e., a signal peptide, is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the term "gene" means the segment of DNA involved in producing a polypeptide chain, that may or may not include regions preceding and following the coding region, e.g. 5' untranslated (5' UTR) or "leader" sequences and 3' UTR or "trailer" sequences, as well as intervening sequences (introns) between individual coding segments (exons).

The gene may encode therapeutically significant proteins or peptides, such as growth factors, cytokines, ligands, receptors and inhibitors, as well as vaccines and antibodies.

The gene may encode commercially important industrial proteins or peptides, such as enzymes, e.g., cellulases such as an *H. grisea* CBH1.1 variant, a *H. jecorina* CBH1 variant or a *S. thermophilium* CBH1. The gene of interest may be a naturally occurring gene, a mutated gene or a synthetic gene.

The "filamentous fungi" of the present invention are eukaryotic microorganisms and include all filamentous forms of the subdivision Eumycotina (see Alexopoulos, C. J. (1962), Introductory Mycology, New York: Wiley). These fungi are characterized by a vegetative mycelium with a cell wall composed of chitin, cellulose, and other complex polysaccharides. The filamentous fungi of the present invention are morphologically, physiologically, and genetically distinct from yeasts. Vegetative growth by filamentous fungi is by hyphal elongation and carbon catabolism is obligately aerobic. In contrast, vegetative growth by yeasts such as *S. cerevisiae* is by budding of a unicellular thallus, and carbon catabolism may be fermentative. *S. cerevisiae* has a prominent, very stable diploid phase, whereas diploids exist only briefly prior to meiosis in filamentous fungi, e.g., *Aspergilli* and *Neurospora*. *S. cervisiae* has 17 chromosomes as opposed to 8 and 7 for *A. nidulans* and *N. crassa* respectively. Recent illustrations of differences between *S. cerevisiae* and filamentous fungi include the inability of *S. cerevisiae* to process *Aspergillus* and *Trichoderma* introns and the inability to recognize many transcriptional regulators of filamentous fungi (Innis, M. A. et al. (1985) Science, 228, 21-26).

The term "heterologous" when used with reference to portions of a nucleic acid indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid, e.g., a promoter from one source and a coding region from another source. Similarly, a heterologous protein will often refer to two or more subsequences that are not found in the same relationship to each other in nature (e.g., a fusion protein).

The terms "isolated" or "purified" as used herein refer to a nucleic acid or amino acid that is removed from at least one component with which it is naturally associated.

In the present context, the term "substantially pure polypeptide" means a polypeptide preparation which contains at the most 10% by weight of other polypeptide material with which it is natively associated (lower percentages of other polypeptide material are preferred, e.g. at the most 8% by weight, at the most 6% by weight, at the most 5% by weight, at the most 4% at the most 3% by weight, at the most 2% by weight, at the most 1% by weight, and at the most ½% by weight). Thus, it is preferred that the substantially pure polypeptide is at least 92% pure, i.e. that the polypeptide constitutes at least 92% by weight of the total polypeptide material present in the preparation, and higher percentages are preferred such as at least 94% pure, at least 95% pure, at least 96% pure, at least 96% pure, at least 97% pure, at least 98% pure, at least 99%, and at the most 99.5% pure. The polypeptides disclosed herein are preferably in a substantially pure form. In particular, it is preferred that the polypeptides disclosed herein are in "essentially pure form", i.e. that the polypeptide preparation is essentially free of other polypeptide material with which it is natively associated. This can be accomplished, for example, by preparing the polypeptide by means of well-known recombinant methods. Herein, the term "substantially pure polypeptide" is synonymous with the terms "isolated polypeptide" and "polypeptide in isolated form".

In general, nucleic acid molecules which encode the variant *H. grisea* CBH1.1 will hybridize, under moderate to high stringency conditions to the sequence provided herein as SEQ ID NO:1 (the variant *H. grisea* CBH1.1). However, in some cases a CBH1-encoding nucleotide sequence is employed that possesses a substantially different codon usage, while the protein encoded by the CBH1-encoding nucleotide sequence has the same or substantially the same amino acid sequence as the native protein. For example, the coding sequence may be modified to facilitate faster expression of CBH1 in a particular prokaryotic or eukaryotic expression system, in accordance with the frequency with which a particular codon is utilized by the host. Te'o, et al. (2000), for example, describes the optimization of genes for expression in filamentous fungi.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm-5° C. (5° C. below the Tm of the probe); "high stringency" at about 5-10° C. below the Tm; "moderate" or "intermediate stringency" at about 10-20° C. below the Tm of the probe; and "low stringency" at about 20-25° C. below the Tm. Functionally, maximum stringency conditions may be used to identify sequences having strict identity or near-strict identity with the hybridization probe; while high stringency conditions are used to identify sequences having about 80% or more sequence identity with the probe.

Moderate and high stringency hybridization conditions are well known in the art (see, for example, Sambrook, et al, 1989, Chapters 9 and 11, and in Ausubel, F. M., et al., 1993, expressly incorporated by reference herein). An example of high stringency conditions includes hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C.

The term "% homology" is used interchangeably herein with the term "% identity" herein and refers to the level of nucleic acid or amino acid sequence identity between the nucleic acid sequence that encodes an *H. grisea* CBH1.1 variant, a *H. jecorina* CBH1 variant or a *S. thermophilium* CBH1 amino acid sequence, when aligned using a sequence alignment program.

For example, as used herein, 80% homology means the same thing as 80% sequence identity determined by a defined algorithm, and accordingly a homologue of a given sequence has greater than 80% sequence identity over a length of the given sequence. Exemplary levels of sequence identity include, but are not limited to, 80, 85, 90, 95, 98% or more sequence identity to a given sequence, e.g., the coding sequence for an *H. grisea* CBH1.1 variant, a *H. jecorina* CBH1 variant or a *S. thermophilium* CBH1, as described herein.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at www.ncbi.nlm.nih.gov/BLAST/. See also, Altschul, et al., 1990 and Altschul, et al., 1997.

Sequence searches are typically carried out using the BLASTN program when evaluating a given nucleic acid sequence relative to nucleic acid sequences in the GenBank DNA Sequences and other public databases. The BLASTX program is preferred for searching nucleic acid sequences that have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62 matrix. (See, e.g., Altschul, et al., 1997.)

A preferred alignment of selected sequences in order to determine "% identity" between two or more sequences, is performed using for example, the CLUSTAL-W program in MacVector version 6.5, operated with default parameters, including an open gap penalty of 10.0, an extended gap penalty of 0.1, and a BLOSUM 30 similarity matrix.

As used herein, the terms "transformed", "stably transformed" or "transgenic" with reference to a cell means the cell has a non-native (heterologous) nucleic acid sequence integrated into its genome or as an episomal plasmid that is maintained through multiple generations.

As used herein, the term "expression" refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

It follows that the term "CBH1.1 expression" refers to transcription and translation of the variant CBH1.1 cellulase gene, the products of which include precursor RNA, mRNA, polypeptide, post-translationally processed polypeptides. By way of example, assays for CBH1.1 expression include Western blot for CBH1.1 protein, Northern blot analysis and reverse transcriptase polymerase chain reaction (RT-PCR) assays for CBH1 mRNA, and endoglucanase activity assays as described in Shoemaker S. P. and Brown R. D. Jr. (Biochim. Biophys. Acta, 1978, 523:133-146) and Schulein (1988). Similarly, as used herein, "CBH1 expression" refers to transcription and translation of a *H. jecorina* CBH1 variant or a *S. thermophilium* CBH1 cellulase gene, the products of which include precursor RNA, mRNA, polypeptide, post-translationally processed polypeptides.

As used herein, the term "surfactant" refers to any compound generally recognized in the art as having surface active qualities. Thus, for example, surfactants comprise anionic, cationic and nonionic surfactants such as those commonly found in detergents. Anionic surfactants include linear or branched alkylbenzenesulfonates; alkyl or alkenyl ether sulfates having linear or branched alkyl groups or alkenyl groups; alkyl or alkenyl sulfates; olefinsulfonates; and alkanesulfonates. Ampholytic surfactants include quaternary ammonium salt sulfonates, and betaine-type ampholytic surfactants. Such ampholytic surfactants have both the positive and negative charged groups in the same molecule. Nonionic surfactants may comprise polyoxyalkylene ethers, as well as higher fatty acid alkanolamides or alkylene oxide adduct thereof, fatty acid glycerine monoesters, and the like.

As used herein, the term "cellulose containing fabric" refers to any sewn or unsewn fabrics, yarns or fibers made of cotton or non-cotton containing cellulose or cotton or non-cotton containing cellulose blends including natural cellulosics and manmade cellulosics (such as jute, flax, ramie, rayon, and lyocell).

As used herein, the term "cotton-containing fabric" refers to sewn or unsewn fabrics, yarns or fibers made of pure cotton or cotton blends including cotton woven fabrics, cotton knits, cotton denims, cotton yarns, raw cotton and the like.

As used herein, the term "stonewashing composition" refers to a formulation for use in stonewashing cellulose containing fabrics. Stonewashing compositions are used to modify cellulose containing fabrics prior to sale, i.e., during the manufacturing process. In contrast, detergent compositions are intended for the cleaning of soiled garments and are not used during the manufacturing process.

As used herein, the term "detergent composition" refers to a mixture which is intended for use in a wash medium for the laundering of soiled cellulose containing fabrics. In the context of the present invention, such compositions may include, in addition to cellulases and surfactants, additional hydrolytic enzymes, builders, bleaching agents, bleach activators, bluing agents and fluorescent dyes, caking inhibitors, masking agents, cellulase activators, antioxidants, and solubilizers.

As used herein, the term "decrease or elimination in expression of the cbh1.1 gene" means that either that the cbh1.1 gene has been deleted from the genome and therefore cannot be expressed by the recombinant host microorganism; or that the cbh1.1 gene has been modified such that a functional CBH1.1 enzyme is not produced by the host microorganism.

The term "variant cbh1.1 gene" or "variant CBH1.1" means, respectively, that the nucleic acid sequence of the cbh1.1 gene from *H. grisea* has been altered by removing, adding, and/or manipulating the coding sequence or the amino acid sequence of the expressed protein has been modified consistent with the invention described herein.

The term "variant cbh1 gene" or "variant CBH1" means, respectively, that the nucleic acid sequence of the cbh1 gene from *H. jecorina* has been altered by removing, adding, and/or manipulating the coding sequence or the amino acid sequence of the expressed protein has been modified consistent with the invention described herein.

As used herein, the terms "active" and "biologically active" refer to a biological activity associated with a particular protein and are used interchangeably herein. For example, the enzymatic activity associated with a protease is proteolysis and, thus, an active protease has proteolytic activity. It follows that the biological activity of a given protein refers to any biological activity typically attributed to that protein by those of skill in the art.

When employed in enzymatic solutions, the homolog or variant CBH1.1, *H. jecorina* CBH1 variant or *S. thermophilium* CBH1 component is generally added in an amount sufficient to allow the highest rate of release of soluble sugars from the biomass. The amount of homolog or variant CBH1.1, *H. jecorina* CBH1 variant or *S. thermophilium* CBH1 component added depends upon the type of biomass to be saccharified which can be readily determined by the skilled artisan. However, when employed, the weight percent of the variant CBH1.1, *H. jecorina* CBH1 variant or *S. thermophilium* CBH1 component relative to any EG type components present in the cellulase composition is from preferably about 1, preferably about 5, preferably about 10, preferably about 15, or preferably about 20 weight percent to preferably about 25, preferably about 30, preferably about 35, preferably about 40, preferably about 45 or preferably about 50 weight percent. Furthermore, preferred ranges may be about 0.5 to about 15 weight percent, about 0.5 to about 20 weight percent, from about 1 to about 10 weight percent, from about 1 to about 15 weight percent, from about 1 to about 20 weight percent, from about 1 to about 25 weight percent, from about 5 to about 20 weight percent, from about 5 to about 25 weight percent, from about 5 to about 30 weight percent, from about 5 to about 35 weight percent, from about 5 to about 40 weight percent, from about 5 to about 45 weight percent, from about 5 to about 50 weight percent, from about 10 to about 20 weight percent, from about 10 to about 25 weight percent, from about 10 to about 30 weight percent, from about 10 to about 35 weight percent, from about 10 to about 40 weight percent, from about 10 to about 45 weight percent, from about 10 to about 50 weight percent, from about 15 to about 20 weight percent, from about 15 to about 25 weight percent, from about 15 to about 30 weight percent, from about 15 to about 35 weight percent, from about 15 to about 30 weight percent, from about 15 to about 45 weight percent, from about 15 to about 50 weight percent.

II. HOST ORGANISMS

Filamentous fungi include all filamentous forms of the subdivision Eumycota and Oomycota. The filamentous fungi are characterized by vegetative mycelium having a cell wall composed of chitin, glucan, chitosan, mannan, and other complex polysaccharides, with vegetative growth by hyphal elongation and carbon catabolism that is obligately aerobic.

In the present invention, the filamentous fungal parent cell may be a cell of a species of, but not limited to, *Trichoderma*, e.g., *Trichoderma longibrachiatum*, *Trichoderma viride*, *Trichoderma koningii*, *Trichoderma harzianum*; *Penicillium* sp.; *Humicola* sp., including *Humicola insolens* and *Humicola grisea*; *Chrysosporium* sp., including *C. lucknowense*; *Gliocladium* sp.; *Aspergillus* sp.; *Fusarium* sp., *Neurospora* sp., *Hypocrea* sp., and *Emericella* sp. As used herein, the term "*Trichoderma*" or "*Trichoderma* sp." refers to any fungal strains which have previously been classified as *Trichoderma* or are currently classified as *Trichoderma*.

In one preferred embodiment, the filamentous fungal parent cell is an *Aspergillus niger, Aspergillus awamori, Aspergillus aculeatus*, or *Aspergillus nidulans* cell.

In another preferred embodiment, the filamentous fungal parent cell is a *Trichoderma reesei* cell.

III. CELLULASES

Cellulases are known in the art as enzymes that hydrolyze cellulose (beta-1,4-glucan or beta D-glucosidic linkages) resulting in the formation of glucose, cellobiose, cellooligosaccharides, and the like. As set forth above, cellulases have been traditionally divided into three major classes: endoglucanases (EC 3.2.1.4) ("EG"), exoglucanases or cellobiohydrolases (EC 3.2.1.91) ("CBH") and beta-glucosidases (EC 3.2.1.21) ("BG"). (Knowles, et al., 1987; Schulein, 1988).

Certain fungi produce complete cellulase systems which include exo-cellobiohydrolases or CBH-type cellulases, endoglucanases or EG-type cellulases and beta-glucosidases or BG-type cellulases (Schulein, 1988). However, sometimes these systems lack CBH-type cellulases and bacterial cellulases also typically include little or no CBH-type cellulases. In addition, it has been shown that the EG components and CBH components synergistically interact to more efficiently degrade cellulose. See, e.g., Wood, 1985. The different components, i.e., the various endoglucanases and exocellobiohydrolases in a multi-component or complete cellulase system, generally have different properties, such as isoelectric point, molecular weight, degree of glycosylation, substrate specificity and enzymatic action patterns.

Cellulase compositions have also been shown to degrade cotton-containing fabrics, resulting in reduced strength loss in the fabric (U.S. Pat. No. 4,822,516), contributing to reluctance to use cellulase compositions in commercial detergent applications. Cellulase compositions comprising endoglucanase components have been suggested to exhibit reduced strength loss for cotton-containing fabrics as compared to compositions comprising a complete cellulase system.

Cellulases have also been shown to be useful in degradation of cellulase biomass to ethanol (wherein the cellulase degrades cellulose to glucose and yeast or other microbes further ferment the glucose into ethanol), in the treatment of mechanical pulp (Pere et al., 1996), for use as a feed additive (WO 91/04673) and in grain wet milling.

Most CBHs and EGs have a multidomain structure consisting of a core domain separated from a cellulose binding domain (CBD) by a linker peptide (Suurnakki et al., 2000). The core domain contains the active site whereas the CBD interacts with cellulose by binding the enzyme to it (van Tilbeurgh et al., 1986; Tomme et al., 1988). The CBDs are particularly important in the hydrolysis of crystalline cellulose. It has been shown that the ability of cellobiohydrolases to degrade crystalline cellulose clearly decreases when the CBD is absent (Linder and Teeri, 1997). However, the exact role and action mechanism of CBDs is still a matter of speculation. It has been suggested that the CBD enhances the enzymatic activity merely by increasing the effective enzyme concentration at the surface of cellulose (Stahlberg et al., 1991), and/or by loosening single cellulose chains from the cellulose surface (Tormo et al., 1996). Most studies concerning the effects of cellulase domains on different substrates have been carried out with core proteins of cellobiohydrolases, as their core proteins can easily be produced by limited proteolysis with papain (Tomme et al., 1988). Numerous cellulases have been described in the scientific literature, examples of which include: from *Trichoderma reesei*: Shoemaker, S. et al., Bio/Technology, 1:691-696, 1983, which discloses CBHI; Teeri, T. et al., Gene, 51:43-52, 1987, which discloses CBHII. Cellulases from species other than *Trichoderma* have also been described e.g., Ooi et al., 1990, which discloses the cDNA sequence coding for endoglucanase F1-CMC produced by *Aspergillus aculeatus*; Kawaguchi T et al., 1996, which discloses the cloning and sequencing of the cDNA encoding beta-glucosidase 1 from *Aspergillus aculeatus*; Sakamoto et al., 1995, which discloses the cDNA sequence encoding the endoglucanase CMCase-1 from *Aspergillus kawachii* IFO 4308; Saarilahti et al., 1990 which discloses an endoglucanase from *Erwinia carotovara*; Spilliaert R, et al., 1994, which discloses the cloning and sequencing of bglA, coding for a thermostable beta-glucanase from *Rhodothermus marinus*; and Halldorsdottir S et al., 1998, which discloses the cloning, sequencing and overexpression of a *Rhodothermus marinus* gene encoding a thermostable cellulase of glycosyl hydrolase family 12. However, there remains a need for identification and characterization of novel cellulases, with improved properties, such as improved performance under conditions of thermal stress or in the presence of surfactants, increased specific activity, altered substrate cleavage pattern, and/or high level expression in vitro.

The development of new and improved cellulase compositions that comprise varying amounts CBH-type cellulase is of interest for use: (1) in detergent compositions that exhibit enhanced cleaning ability, function as a softening agent and/or improve the feel of cotton fabrics (e.g., "stone washing" or "biopolishing"); (2) in compositions for degrading wood pulp or other biomass into sugars (e.g., for bio-ethanol production); and/or (3) in feed compositions.

IV. MOLECULAR BIOLOGY

In one embodiment this invention provides for the expression of variant *H. grisea* CBH1.1 cellulase genes under the control of a promoter functional in a filamentous fungus. Therefore, this invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and Ausubel et al., eds., *Current Protocols in Molecular Biology* (1994)).

A. Methods for Identifying Variant CBH1.1 Genes

Two publically available *H. grisea* CBH1.1 nucleic acid sequences are shown in FIG. 5. The invention, in one aspect, encompasses a nucleic acid molecule encoding a variant *H. grisea* CBH1.1 described herein. The nucleic acid may be a DNA molecule.

Techniques that can be used to isolate variant CBH1.1-encoding DNA sequences are well known in the art and include, but are not limited to, cDNA and/or genomic library screening with a homologous DNA probes and expression screening with activity assays or antibodies against CBH1. Any of these methods can be found in Sambrook, et al. or in CURRENT PROTOCOLS IN MOLECULAR BIOLOGY, F. Ausubel, et al., ed. Greene Publishing and Wiley-Interscience, New York (1987) ("Ausubel").

B. Nucleic Acid Constructs/Expression Vectors.

Natural or synthetic polynucleotide fragments encoding a variant *H. grisea* CBH1.1 cellulase ("variant *H. grisea* CBH1.1 cellulase-encoding nucleic acid sequences") may be incorporated into heterologous nucleic acid constructs or vectors, capable of introduction into, and replication in, a filamentous fungal or yeast cell. The vectors and methods disclosed herein are suitable for use in host cells for the expression of a variant CBH1.1 cellulase. Any vector may be used as long as it is replicable and viable in the cells into which it is introduced. Large numbers of suitable vectors and promoters are known to those of skill in the art, and are commercially available. Cloning and expression vectors are also described in Sambrook et al., 1989, Ausubel F M et al., 1989, and Strathern et al., 1981, each of which is expressly incorporated by reference herein. Appropriate expression vectors for fungi are described in van den Hondel, C. A. M. J. J. et al. (1991) In: Bennett, J. W. and Lasure, L. L. (eds.) More Gene Manipulations in Fungi. Academic Press, pp. 396-428. The appropriate DNA sequence may be inserted into a plasmid or vector (collectively referred to herein as "vectors") by a variety of procedures. In general, the DNA sequence is inserted into an appropriate restriction endonuclease site(s) by standard procedures. Such procedures and related sub-cloning procedures are deemed to be within the scope of knowledge of those skilled in the art.

Recombinant filamentous fungi comprising the coding sequence for a variant CBH1.1, a *H. jecorina* CBH1 variant or a *S. thermophilium* CBH1 cellulase may be produced by introducing a heterologous nucleic acid construct comprising the variant CBH1.1, a *H. jecorina* CBH1 variant or a *S. thermophilium* CBH1 cellulase coding sequence into the cells of a selected strain of the filamentous fungi.

Once the desired form of a variant CBH1.1, a *H. jecorina* CBH1 variant or a *S. thermophilium* CBH1 cellulase nucleic acid sequence is obtained, it may be modified in a variety of ways. Where the sequence involves non-coding flanking regions, the flanking regions may be subjected to resection, mutagenesis, etc. Thus, transitions, transversions, deletions, and insertions may be performed on the naturally occurring sequence.

A selected variant CBH1.1, a *H. jecorina* CBH1 variant or a *S. thermophilium* CBH1 cellulase coding sequence may be inserted into a suitable vector according to well-known recombinant techniques and used to transform filamentous fungi capable of cellulase expression. Due to the inherent degeneracy of the genetic code, other nucleic acid sequences which encode substantially the same or a functionally equivalent amino acid sequence may be used to clone and express a variant CBH1.1, a *H. jecorina* CBH1 variant or a *S. thermophilium* CBH1 cellulase. Therefore it is appreciated that such substitutions in the coding region fall within the sequence variants covered by the present invention.

The present invention also includes recombinant nucleic acid constructs comprising one or more of the variant CBH1.1, a *H. jecorina* CBH1 variant or a *S. thermophilium* CBH1 cellulase-encoding nucleic acid sequences as described above. The constructs comprise a vector, such as a plasmid or viral vector, into which a sequence of the invention has been inserted, in a forward or reverse orientation.

Heterologous nucleic acid constructs may include the coding sequence for a variant CBH1.1, a *H. jecorina* CBH1 variant or a *S. thermophilium* CBH1 cellulase: (i) in isolation; (ii) in combination with additional coding sequences; such as fusion protein or signal peptide coding sequences, where the desired cellulase coding sequence is the dominant coding sequence; (iii) in combination with non-coding sequences, such as introns and control elements, such as promoter and terminator elements or 5' and/or 3' untranslated regions, effective for expression of the coding sequence in a suitable host; and/or (iv) in a vector or host environment in which the variant CBH1.1, a *H. jecorina* CBH1 variant or a *S. thermophilium* CBH1 cellulase coding sequence is a heterologous gene.

In one aspect of the present invention, a heterologous nucleic acid construct is employed to transfer a variant CBH1.1, a *H. jecorina* CBH1 variant or a *S. thermophilium* CBH1 cellulase-encoding nucleic acid sequence into a cell in vitro, with established filamentous fungal and yeast lines preferred. For long-term, production of a variant CBH1.1, a *H. jecorina* CBH1 variant or a *S. thermophilium* CBH1 cellulase, stable expression is preferred. It follows that any method effective to generate stable transformants may be used in practicing the invention.

Appropriate vectors are typically equipped with a selectable marker-encoding nucleic acid sequence, insertion sites, and suitable control elements, such as promoter and termination sequences. The vector may comprise regulatory sequences, including, for example, non-coding sequences, such as introns and control elements, i.e., promoter and terminator elements or 5' and/or 3' untranslated regions, effective for expression of the coding sequence in host cells (and/or in a vector or host cell environment in which a modified soluble protein antigen coding sequence is not normally expressed), operably linked to the coding sequence. Large numbers of suitable vectors and promoters are known to those of skill in the art, many of which are commercially available and/or are described in Sambrook, et al., (supra).

Exemplary promoters include both constitutive promoters and inducible promoters, examples of which include a CMV promoter, an SV40 early promoter, an RSV promoter, an EF-1α promoter, a promoter containing the tet responsive element (TRE) in the tet-on or tet-off system as described (ClonTech and BASF), the beta actin promoter and the metallothionine promoter that can upregulated by addition of certain metal salts. A promoter sequence is a DNA sequence which is recognized by the particular filamentous fungus for expression purposes. It is operably linked to DNA sequence encoding a variant CBH1.1, a *H. jecorina* CBH1 variant or a *S. thermophilium* CBH1 polypeptide. Such linkage comprises positioning of the promoter with respect to the initiation codon of the DNA sequence encoding the variant CBH1.1, a *H. jecorina* CBH1 variant or a *S. thermophilium* CBH1 polypeptide in the disclosed expression vectors. The promoter sequence contains transcription and translation control sequence which mediate the expression of the variant CBH1.1, a *H. jecorina* CBH1 variant or a *S. thermophilium* CBH1 polypeptide. Examples include the promoters from the *Aspergillus niger*, *A awamori* or *A. oryzae* glucoamylase, alpha-amylase, or alpha-glucosidase encoding genes; the *A. nidulans* gpdA or trpC Genes; the *Neurospora crassa* cbh1 or trp1 genes; the *A. niger* or *Rhizomucor miehei* aspartic proteinase encoding genes; the *H. jecorina* cbh1, cbh2, egl1, egl2, or other cellulase encoding genes.

The choice of the proper selectable marker will depend on the host cell, and appropriate markers for different hosts are well known in the art. Typical selectable marker genes include argB from *A. nidulans* or *H. jecorina*, amdS from *A. nidulans*, pyr4 from *Neurospora crassa* or *H. jecorina*, pyrG from *Aspergillus niger* or *A. nidulans*. Additional exemplary selectable markers include, but are not limited to trpc, trp1, oliC31, niaD or leu2, which are included in heterologous nucleic acid constructs used to transform a mutant strain such as trp-, pyr-, leu- and the like.

Such selectable markers confer to transformants the ability to utilize a metabolite that is usually not metabolized by the filamentous fungi. For example, the amdS gene from *H. jecorina* which encodes the enzyme acetamidase that allows transformant cells to grow on acetamide as a nitrogen source. The selectable marker (e.g. pyrG) may restore the ability of an auxotrophic mutant strain to grow on a selective minimal medium or the selectable marker (e.g. olic31) may confer to transformants the ability to grow in the presence of an inhibitory drug or antibiotic.

The selectable marker coding sequence is cloned into any suitable plasmid using methods generally employed in the art. Exemplary plasmids include pUC18, pBR322, pRAX and pUC100. The pRAX plasmid contains AMA1 sequences from *A. nidulans*, which make it possible to replicate in *A. niger*.

The practice of the present invention will employ, unless otherwise indicated, conventional techniques of molecular biology, microbiology, recombinant DNA, and immunology, which are within the skill of the art. Such techniques are explained fully in the literature. See, for example, Sambrook et al., 1989; Freshney, 1987; Ausubel, et al., 1993; and Coligan et al., 1991. All patents, patent applications, articles and publications mentioned herein, are hereby expressly incorporated herein by reference.

C. Methods for Transforming a Host Cell

In the present invention, the filamentous fungal parent cell may be a cell of a species of, but not limited to, *Trichoderma*, e.g., *Trichoderma longibrachiatum* (*reesei*), *Trichoderma viride*, *Trichoderma koningii*, *Trichoderma harzianum*; *Penicillium* sp.; *Humicola* sp., including *Humicola insolens*; *Chrysosporium* sp., including *C. lucknowense*; *Gliocladium* sp.; *Aspergillus* sp.; *Fusarium* sp., *Neurospora* sp., *Hypocrea* sp., and *Emericella* sp. As used herein, the term "*Trichoderma*" or "*Trichoderma* sp." refers to any fungal strains which have previously been classified as *Trichoderma* or are currently classified as *Trichoderma*.

Examples of parental cell lines which may be treated and/or modified for variant *H. grisea* CBH1.1, *H. jecorina* CBH1 variant or *S. thermophilium* CBH1 expression include, but are not limited to, filamentous fungal cells. Examples of appropriate primary cell types for use in practicing the invention include, but are not limited to, *Aspergillus* and *Trichoderma*.

In one embodiment, the filamentous fungal parent cell is an *Aspergillus niger*, *Aspergillus awamori*, *Aspergillus aculeatus*, or *Aspergillus nidulans* cell.

In a second embodiment, the filamentous fungal parent cell is a *Hypocrea jecorina* cell. This cell was previously referred to as *T. reesei*.

After DNA sequences that encode the CBH1.1 variants, *H. jecorina* CBH1 variant or *S. thermophilium* CBH1 have been cloned into DNA constructs, the DNA is used to transform microorganisms. The microorganism to be transformed for the purpose of expressing a variant CBH1.1, a *H. jecorina* CBH1 variant or a *S. thermophilium* CBH1 according to the present invention may advantageously comprise a strain derived from *Trichoderma* sp. Thus, a preferred mode for preparing variant CBH1.1, a *H. jecorina* CBH1 variant or a *S. thermophilium* CBH1 cellulases according to the present invention comprises transforming a *Trichoderma* sp. host cell with a DNA construct comprising at least a fragment of DNA encoding a portion or all of the variant CBH1.1, a *H. jecorina* CBH1 variant or a *S. thermophilium* CBH1. The DNA construct will generally be functionally attached, i.e., operably linked, to a promoter. The transformed host cell is then grown under conditions so as to express the variant *H. grisea* CBH1.1, a *H. jecorina* CBH1 variant or a *S. thermophilium* CBH1. Subsequently, the variant *H. grisea* CBH1.1, a *H. jecorina* CBH1 variant or a *S. thermophilium* CBH1 may be isolated. It may be desirable to have the variant *H. grisea* CBH1.1, a *H. jecorina* CBH1 variant or a *S. thermophilium* CBH1 in a substantially pure form. Similarly, it may be desirable to have the variant *H. grisea* CBH1.1, a *H. jecorina* CBH1 variant or a *S. thermophilium* CBH1 in an essentially pure form.

However, it may in fact be that the best expression vehicle for a given DNA encoding a variant CBH1.1 may differ from *H. jecorina* (i.e., *T. reesei*). Thus, it may be that it will be most advantageous to express a protein in a transformation host that bears phylogenetic similarity to the source organism for the variant CBH1.1. In an alternative embodiment, *Aspergillus niger* can be used as an expression vehicle. For a description of transformation techniques with *A. niger*, see WO 98/31821, the disclosure of which is incorporated by reference in its entirety.

Accordingly, the present description of a *Trichoderma* spp. expression system is provided for illustrative purposes only and as one option for expressing the variant CBH1.1 of the invention. One of skill in the art, however, may be inclined to express the DNA encoding variant CBH1.1 in a different host cell if appropriate and it should be understood that the source of the variant CBH1.1 should be considered in determining the optimal expression host. Additionally, the skilled worker in the field will be capable of selecting the best expression system for a particular gene through routine techniques utilizing the tools available in the art.

D. Methods for Expressing a Variant CBH1.1, a *H. Jecorina* CBH1 Variant or a *S. Thermophilium* CBH1

The methods of the invention rely on the use cells to express a variant CBH1.1 cellulase, with no particular method of expression required.

The invention provides host cells that have been transduced, transformed or transfected with an expression vector comprising a variant CBH1.1, a *H. jecorina* CBH1 variant or a *S. thermophilium* CBH1 cellulase-encoding nucleic acid sequence. The culture conditions, such as temperature, pH and the like, are those previously used for the parental host cell prior to transduction, transformation or transfection and will be apparent to those skilled in the art.

In one approach, a filamentous fungal cell or yeast cell is transfected with an expression vector having a promoter or biologically active promoter fragment or one or more (e.g., a series) of enhancers which functions in the host cell line, operably linked to a DNA segment encoding a variant CBH1.1, a *H. jecorina* CBH1 variant or a *S. thermophilium* CBH1 cellulase, such that the variant CBH1.1, a *H. jecorina* CBH1 variant or a *S. thermophilium* CBH1 cellulase is expressed in the cell line.

Thus, the present invention provides filamentous fungi comprising cells which have been modified, selected and cultured in a manner effective to result in variant CBH1.1, a *H. jecorina* CBH1 variant or a *S. thermophilium* CBH1 cellulase production or expression relative to the corresponding non-transformed parental fungi.

Examples of species of parental filamentous fungi that may be treated and/or modified for desired cellulase expression include, but are not limited to *Trichoderma, Penicillium* sp., *Humicola* sp., including *Humicola insolens; Aspergillus* sp., including *Aspergillus niger, Chrysosporium* sp., *Fusarium* sp., *Hypocrea* sp., and *Emericella* sp.

Cells expressing a variant CBH1.1, a *H. jecorina* CBH1 variant or a *S. thermophilium* CBH1 cellulase are cultured under conditions typically employed to culture the parental fungal line. Generally, cells are cultured in a standard medium containing physiological salts and nutrients, such as described in Pourquie, J. et al., Biochemistry and Genetics of Cellulose Degradation, eds. Aubert, J. P. et al., Academic Press, pp. 71-86, 1988 and Ilmen, M. et al., Appl. Environ. Microbiol. 63:1298-1306, 1997. Culture conditions are also standard, e.g., cultures are incubated at 28° C. in shaker cultures or fermenters until desired levels of variant CBH1.1 cellulase expression are achieved.

Preferred culture conditions for a given filamentous fungus may be found in the scientific literature and/or from the source of the fungi such as the American Type Culture Collection (ATCC; <www.atcc.org>). After fungal growth has been established, the cells are exposed to conditions effective to cause or permit the expression of a variant CBH1.1 cellulase.

In cases where a variant CBH1.1, a *H. jecorina* CBH1 variant or a *S. thermophilium* CBH1 cellulase coding sequence is under the control of an inducible promoter, the inducing agent, e.g., a sugar, metal salt or antibiotics, is added to the medium at a concentration effective to induce variant CBH1.1, a *H. jecorina* CBH1 variant or a *S. thermophilium* CBH1 cellulase expression.

In one embodiment, the strain comprises *Aspergillus niger*, which is a useful strain for obtaining overexpressed protein. For example *A. niger* var *awamori* dgr246 is known to secrete elevated amounts of secreted cellulases (Goedegebuur et al, Curr. Genet (2002) 41: 89-98). Other strains of *Aspergillus niger* var *awamori* such as GCDAP3, GCDAP4 and GAP3-4 are known Ward et al (Ward, M, Wilson, L. J. and Kodama, K. H., 1993, Appl. Microbiol. Biotechnol. 39:738-743).

In another embodiment, the strain comprises *Trichoderma reesei*, which is a useful strain for obtaining overexpressed protein. For example, RL-P37, described by Sheir-Neiss, et al., *Appl. Microbiol. Biotechnol.* 20:46-53 (1984) is known to secrete elevated amounts of cellulase enzymes. Functional equivalents of RL-P37 include *Trichoderma reesei* strain RUT-C30 (ATCC No. 56765) and strain QM9414 (ATCC No. 26921). It is contemplated that these strains would also be useful in overexpressing variant CBH1.1, a *H. jecorina* CBH1 variant or a *S. thermophilium* CBH1.

Where it is desired to obtain the desired cellulase in the absence of potentially detrimental native cellulolytic activity, it is useful to obtain a host cell strain which has had one or more cellulase genes deleted prior to introduction of a DNA construct or plasmid containing the DNA fragment encoding the variant CBH1.1, a *H. jecorina* CBH1 variant or a *S. thermophilium* CBH1 cellulase. Such strains may be prepared by the method disclosed in U.S. Pat. No. 5,246,853 and WO 92/06209, which disclosures are hereby incorporated by reference. By expressing a variant CBH1.1, a *H. jecorina* CBH1 variant or a *S. thermophilium* CBH1 cellulase in a host microorganism that is missing one or more cellulase genes, the identification and subsequent purification procedures are simplified. Any gene from *Trichoderma* sp. which has been cloned can be deleted, for example, the cbh1, cbh2, egl1, and egl2 genes as well as those encoding a variant CBH1.1, a *H. jecorina* CBH1 variant or a *S. thermophilium* CBH1 protein (see e.g., U.S. Pat. No. 5,475, 101 and WO 94/28117, respectively).

Gene deletion may be accomplished by inserting a form of the desired gene to be deleted or disrupted into a plasmid by methods known in the art. The deletion plasmid is then cut at an appropriate restriction enzyme site(s), internal to the desired gene coding region, and the gene coding sequence or part thereof replaced with a selectable marker. Flanking DNA sequences from the locus of the gene to be deleted or disrupted, preferably between about 0.5 to 2.0 kb, remain on either side of the selectable marker gene. An appropriate deletion plasmid will generally have unique restriction enzyme sites present therein to enable the fragment containing the deleted gene, including flanking DNA sequences, and the selectable marker gene to be removed as a single linear piece.

A selectable marker must be chosen so as to enable detection of the transformed microorganism. Any selectable marker gene that is expressed in the selected microorganism will be suitable. For example, with *Aspergillus* sp., the selectable marker is chosen so that the presence of the selectable marker in the transformants will not significantly affect the properties thereof. Such a selectable marker may be a gene that encodes an assayable product. For example, a functional copy of a *Aspergillus* sp. gene may be used which if lacking in the host strain results in the host strain displaying an auxotrophic phenotype.

In one embodiment, a pyrG$^-$ derivative strain of *Aspergillus* sp. is transformed with a functional pyrG gene, which thus provides a selectable marker for transformation. A pyrG$^-$ derivative strain may be obtained by selection of *Aspergillus* sp. strains that are resistant to fluoroorotic acid (FOA). The pyrG gene encodes orotidine-5'-monophosphate decarboxylase, an enzyme required for the biosynthesis of uridine. Strains with an intact pyrG gene grow in a medium lacking uridine but are sensitive to fluoroorotic acid. It is possible to select pyrG⁻ derivative strains that lack a functional orotidine monophosphate decarboxylase enzyme and require uridine for growth by selecting for FOA resistance. Using the FOA selection technique it is also possible to obtain uridine-requiring strains which lack a functional orotate pyrophoribosyl transferase. It is possible to transform these cells with a functional copy of the gene encoding this enzyme (Berges & Barreau, *Curr. Genet.* 19:359-365 (1991), and van Hartingsveldte et al., (1986) Development of a homologous transformation system for *Aspergillus niger* based on the pyrG gene. Mol. Gen. Genet. 206:71-75). Selection of derivative strains is easily performed using the FOA resistance technique referred to above, and thus, the pyrG gene is preferably employed as a selectable marker. In another embodiment, a pyr4⁻ derivative strain of *Trichoderma* sp. is transformed with a functional pyr4 gene, which thus provides a selectable marker for transformation. Although the following discusses the *Aspergillus* system, similar procedures for *Trichoderma* and other fungal systems may be used as will be appreciated by one skilled in the art.

To transform pyrG⁻*Aspergillus* sp. so as to be lacking in the ability to express one or more cellulase genes, a single DNA fragment comprising a disrupted or deleted cellulase gene is then isolated from the deletion plasmid and used to transform an appropriate pyr⁻*Aspergillus* host. Transformants are then identified and selected based on their ability to express the pyrG gene product and thus compliment the uridine auxotrophy of the host strain. Southern blot analysis is then carried out on the resultant transformants to identify and confirm a double crossover integration event that replaces part or all of the coding region of the genomic copy of the gene to be deleted with the pyr4 selectable markers.

Although the specific plasmid vectors described above relate to preparation of pyr⁻ transformants, the present invention is not limited to these vectors. Various genes can be deleted and replaced in the *Aspergillus* sp. strain using the above techniques. In addition, any available selectable markers can be used, as discussed above. In fact, any *Aspergillus* sp. gene that has been cloned, and thus identified, can be deleted from the genome using the above-described strategy.

As stated above, the host strains used are derivatives of *Aspergillus* sp. that lack or have a nonfunctional gene or genes corresponding to the selectable marker chosen. For example, if the selectable marker of pyrG is chosen, then a specific pyrG⁻ derivative strain is used as a recipient in the transformation procedure. Similarly, selectable markers comprising *Aspergillus* sp. genes equivalent to the *Aspergillus nidulans* genes amdS, argB, trpC, niaD may be used. The corresponding recipient strain must therefore be a derivative strain such as argB⁻, trpC⁻, niaD⁻, respectively.

DNA encoding the variant CBH1.1 cellulase is then prepared for insertion into an appropriate microorganism. According to the present invention, DNA encoding a variant CBH1.1 cellulase comprises the DNA necessary to encode for a protein that has functional cellulolytic activity. The DNA fragment encoding the variant CBH1.1, a *H. jecorina* CBH1 variant or a *S. thermophilium* CBH1 cellulase may be functionally attached to a fungal promoter sequence, for example, the promoter of the glaA gene.

It is also contemplated that more than one copy of DNA encoding a variant CBH1.1, a *H. jecorina* CBH1 variant or a *S. thermophilium* CBH1 cellulase may be recombined into the strain to facilitate overexpression. The DNA encoding the variant CBH1.1, a *H. jecorina* CBH1 variant or a *S. thermophilium* CBH1 cellulase may be prepared by the construction of an expression vector carrying the DNA encoding the cellulase. The expression vector carrying the inserted DNA fragment encoding the variant CBH1.1 cellulase may be any vector which is capable of replicating autonomously in a given host organism or of integrating into the DNA of the host, typically a plasmid. In preferred embodiments two types of expression vectors for obtaining expression of genes are contemplated. The first contains DNA sequences in which the promoter, gene-coding region, and terminator sequence all originate from the gene to be expressed. Gene truncation may be obtained where desired by deleting undesired DNA sequences (e.g., coding for unwanted domains) to leave the domain to be expressed under control of its own transcriptional and translational regulatory sequences. A selectable marker is also contained on the vector allowing the selection for integration into the host of multiple copies of the novel gene sequences.

The second type of expression vector is preassembled and contains sequences required for high-level transcription and a selectable marker. It is contemplated that the coding region for a gene or part thereof can be inserted into this general-purpose expression vector such that it is under the transcriptional control of the expression cassettes promoter and terminator sequences. For example, pRAX is such a general-purpose expression vector. Genes or part thereof can be inserted downstream of the strong glaA promoter. An example of an integrative expression vector is the pTrex vector. Genes or part thereof can be inserted downstream of the strong cbh1 promoter.

In the vector, the DNA sequence encoding the variant CBH1.1, a *H. jecorina* CBH1 variant or a *S. thermophilium* CBH1 cellulase of the present invention should be operably linked to transcriptional and translational sequences, i.e., a suitable promoter sequence and signal sequence in reading frame to the structural gene. The promoter may be any DNA sequence that shows transcriptional activity in the host cell and may be derived from genes encoding proteins either homologous or heterologous to the host cell. An optional signal peptide provides for extracellular production of the variant CBH1.1, a *H. jecorina* CBH1 variant or a *S. thermophilium* CBH1 cellulase. The DNA encoding the signal sequence is preferably that which is naturally associated with the gene to be expressed, however the signal sequence from any suitable source is contemplated in the present invention.

The procedures used to fuse the DNA sequences coding for the variant CBH1.1, a *H. jecorina* CBH1 variant or a *S. thermophilium* CBH1 cellulase of the present invention with the promoter into suitable vectors are well known in the art.

Various methods may be employed for delivering an expression vector, DNA vector or construct described above into cells in vitro. Methods of introducing nucleic acids into cells for expression of heterologous nucleic acid sequences are also known to the ordinarily skilled artisan, including, but not limited to electroporation; nuclear microinjection or direct microinjection into single cells; bacterial protoplast fusion with intact cells; use of polycations, e.g., polybrene or polyornithine; membrane fusion with liposomes, lipofectamine or lipofection-mediated transfection; high velocity bombardment with DNA-coated microprojectiles; incubation with calcium phosphate-DNA precipitate; DEAE-Dextran mediated transfection; infection with modified viral nucleic acids; *Agrobacterium*-mediated transfer of DNA; and the like. In addition, heterologous nucleic acid constructs comprising a variant CBH1.1-encoding nucleic acid sequence can be transcribed in vitro, and the resulting RNA introduced into the host cell by well-known methods, e.g., by injection.

The preferred method in the present invention to prepare *Aspergillus* sp. for transformation involves the preparation of protoplasts from fungal mycelium. See Campbell et al. Improved transformation efficiency of *A. niger* using homologous niaD gene for nitrate reductase. Curr. Genet. 16:53-56; 1989. The mycelium can be obtained from germinated vegetative spores. The mycelium is treated with an enzyme that digests the cell wall resulting in protoplasts. The protoplasts are then protected by the presence of an osmotic stabilizer in the suspending medium. These stabilizers include sorbitol, mannitol, potassium chloride, magnesium sulfate and the like. Usually the concentration of these stabilizers varies between 0.8 M and 1.2 M. It is preferable to use about a 1.2 M solution of sorbitol in the suspension medium.

Uptake of the DNA into the host *Aspergillus* sp. strain is dependent upon the calcium ion concentration. Generally between about 10 mM $CaCl_2$ and 50 mM $CaCl_2$ is used in an uptake solution. Besides the need for the calcium ion in the uptake solution, other items generally included are a buffering system such as TE buffer (10 Mm Tris, pH 7.4; 1 mM EDTA) or 10 mM MOPS, pH 6.0 buffer (morpholinepropanesulfonic acid) and polyethylene glycol (PEG). It is believed that the polyethylene glycol acts to fuse the cell membranes thus permitting the contents of the medium to be delivered into the cytoplasm of the *Aspergillus* sp. strain and the plasmid DNA is transferred to the nucleus. This fusion frequently leaves multiple copies of the plasmid DNA tenderly integrated into the host chromosome.

Usually a suspension containing the *Aspergillus* sp. protoplasts or cells that have been subjected to a permeability treatment at a density of $10^5$ to $10^6$/mL, preferably $2\times10^5$/mL are used in transformation. A volume of 100 µL of these protoplasts or cells in an appropriate solution (e.g., 1.2 M sorbitol; 50 mM $CaCl_2$) are mixed with the desired DNA. Generally a high concentration of PEG is added to the uptake solution. From 0.1 to 1 volume of 25% PEG 4000 can be added to the protoplast suspension. However, it is preferable to add about 0.25 volumes to the protoplast suspension. Additives such as dimethyl sulfoxide, heparin, spermidine, potassium chloride and the like may also be added to the uptake solution and aid in transformation. Similar procedures are available for other fungal host cells. See, for example, U.S. Pat. No. 6,268,328, the contents of which are hereby incorporated by reference.

Generally, the mixture is then incubated at approximately 0° C. for a period of between 10 to 30 minutes. Additional PEG is then added to the mixture to further enhance the uptake of the desired gene or DNA sequence. The 25% PEG 4000 is generally added in volumes of 5 to 15 times the volume of the transformation mixture; however, greater and lesser volumes may be suitable. The 25% PEG 4000 is preferably about 10 times the volume of the transformation mixture. After the PEG is added, the transformation mixture is then incubated either at room temperature or on ice before the addition of a sorbitol and $CaCl_2$ solution. The protoplast suspension is then further added to molten aliquots of a growth medium. This growth medium permits the growth of transformants only. Any growth medium can be used in the present invention that is suitable to grow the desired transformants. However, if $Pyr^+$ transformants are being selected it is preferable to use a growth medium that contains no uridine. The subsequent colonies are transferred and purified on a growth medium depleted of uridine.

At this stage, stable transformants may be distinguished from unstable transformants by their faster growth rate and the formation of circular colonies with a smooth, rather than ragged outline on solid culture medium lacking uridine. Additionally, in some cases a further test of stability may made by growing the transformants on solid non-selective medium (i.e. containing uridine), harvesting spores from this culture medium and determining the percentage of these spores which will subsequently germinate and grow on selective medium lacking uridine. Alternatively, other methods known in the art may be used to select transformants.

In a particular embodiment of the above method, the variant CBH1.1, a *H. jecorina* CBH1 variant or a *S. thermophilium* CBH1 cellulase(s) are recovered in active form from the host cell after growth in liquid media either as a result of the appropriate post translational processing of the variant CBH1.1, a *H. jecorina* CBH1 variant or a *S. thermophilium* CBH1 cellulase.

E. Methods of Analysis for CBH1 Nucleic Acid Coding Sequences and/or Protein Expression.

In order to evaluate the expression of a variant CBH1.1, a *H. jecorina* CBH1 variant or a *S. thermophilium* CBH1 cellulase by a cell line that has been transformed with a variant CBH1.1, a *H. jecorina* CBH1 variant or a *S. thermophilium* CBH1 cellulase-encoding nucleic acid construct, assays can be carried out at the protein level, the RNA level or by use of functional bioassays particular to cellobiohydrolase activity and/or production.

In one exemplary application of the variant CBH1.1, a *H. jecorina* CBH1 variant or a *S. thermophilium* CBH1 cellulase nucleic acid and protein sequences described herein, a genetically modified strain of filamentous fungi, e.g., *Trichoderma reesei*, is engineered to produce an increased amount of a variant CBH1.1, a *H. jecorina* CBH1 variant or a *S. thermophilium* CBH1 cellulase. Such genetically modified filamentous fungi would be useful to produce a cellulase product with greater increased cellulolytic capacity. In one approach, this is accomplished by introducing the coding sequence for a variant CBH1.1, a *H. jecorina* CBH1 variant or a *S. thermophilium* CBH1 cellulase into a suitable host, e.g., a filamentous fungi such as *Aspergillus niger*.

Accordingly, the invention includes methods for expressing a variant CBH1.1, a *H. jecorina* CBH1 variant or a *S. thermophilium* CBH1 cellulase in a filamentous fungus or other suitable host by introducing an expression vector containing the DNA sequence encoding a variant CBH1.1, a *H. jecorina* CBH1 variant or a *S. thermophilium* CBH1 cellulase into cells of the filamentous fungus or other suitable host.

In another aspect, the invention includes methods for modifying the expression of a variant CBH1.1, a *H. jecorina* CBH1 variant or a *S. thermophilium* CBH1 cellulase in a filamentous fungus or other suitable host. Such modification includes a decrease or elimination in expression of the endogenous CBH.

In general, assays employed to analyze the expression of a variant CBH1.1, a *H. jecorina* CBH1 variant or a *S. thermophilium* CBH1 cellulase include, Northern blotting, dot blotting (DNA or RNA analysis), RT-PCR (reverse transcriptase polymerase chain reaction), or in situ hybridization, using an appropriately labeled probe (based on the nucleic acid coding sequence) and conventional Southern blotting and autoradiography.

In addition, the production and/or expression of a variant CBH1.1, a *H. jecorina* CBH1 variant or a *S. thermophilium*

CBH1 cellulase may be measured in a sample directly, for example, by assays for cellobiohydrolase activity, expression and/or production. Such assays are described, for example, in Becker et al., Biochem J. (2001) 356:19-30 and Mitsuishi et al., FEBS (1990) 275:135-138, each of which is expressly incorporated by reference herein. The ability of CBH1 to hydrolyze isolated soluble and insoluble substrates can be measured using assays described in Srisodsuk et al., J. Biotech. (1997) 57:49-57 and Nidetzky and Claeyssens Biotech. Bioeng. (1994) 44:961-966. Substrates useful for assaying cellobiohydrolase, endoglucanase or β-glucosidase activities include crystalline cellulose, filter paper, phosphoric acid swollen cellulose, cellooligosaccharides, methylumbelliferyl lactoside, methylumbelliferyl cellobioside, orthonitrophenyl lactoside, paranitrophenyl lactoside, orthonitrophenyl cellobioside, paranitrophenyl cellobioside.

In addition, protein expression, may be evaluated by immunological methods, such as immunohistochemical staining of cells, tissue sections or immunoassay of tissue culture medium, e.g., by Western blot or ELISA. Such immunoassays can be used to qualitatively and quantitatively evaluate expression of a variant CBH1.1, a *H. jecorina* CBH1 variant or a *S. thermophilium* CBH1 cellulase. The details of such methods are known to those of skill in the art and many reagents for practicing such methods are commercially available.

A purified form of a variant CBH1.1, a *H. jecorina* CBH1 variant or a *S. thermophilium* CBH1 cellulase may be used to produce either monoclonal or polyclonal antibodies specific to the expressed protein for use in various immunoassays. (See, e.g., Hu et al., 1991). Exemplary assays include ELISA, competitive immunoassays, radioimmunoassays, Western blot, indirect immunofluorescent assays and the like. In general, commercially available antibodies and/or kits may be used for the quantitative immunoassay of the expression level of cellobiohydrolase proteins.

F. Methods for Purifying a CBH1

In general, a variant CBH1.1, a *H. jecorina* CBH1 variant or a *S. thermophilium* CBH1 cellulase protein produced in cell culture is secreted into the medium and may be purified or isolated, e.g., by removing unwanted components from the cell culture medium. However, in some cases, a variant CBH1.1, a *H. jecorina* CBH1 variant or a *S. thermophilium* CBH1 cellulase protein may be produced in a cellular form necessitating recovery from a cell lysate. In such cases the variant CBH1.1, a *H. jecorina* CBH1 variant or a *S. thermophilium* CBH1 cellulase protein is purified from the cells in which it was produced using techniques routinely employed by those of skill in the art. Examples include, but are not limited to, affinity chromatography (Tilbeurgh et al., 1984), ion-exchange chromatographic methods (Goya) et al., 1991; Fliess et al., 1983; Bhikhabhai et al., 1984; Ellouz et al., 1987), including ion-exchange using materials with high resolution power (Medve et al., 1998), hydrophobic interaction chromatography (Tomaz and Queiroz, 1999), and two-phase partitioning (Brumbauer, et al., 1999).

Typically, the variant CBH1.1, a *H. jecorina* CBH1 variant or a *S. thermophilium* CBH1 cellulase protein is fractionated to segregate proteins having selected properties, such as binding affinity to particular binding agents, e.g., antibodies or receptors; or which have a selected molecular weight range, or range of isoelectric points.

Once expression of a given variant CBH1.1, a *H. jecorina* CBH1 variant or a *S. thermophilium* CBH1 cellulase protein is achieved, the variant CBH1.1, a *H. jecorina* CBH1 variant or a *S. thermophilium* CBH1 cellulase protein thereby produced is purified from the cells or cell culture. Exemplary procedures suitable for such purification include the following: antibody-affinity column chromatography, ion exchange chromatography; ethanol precipitation; reverse phase HPLC; chromatography on silica or on a cation-exchange resin such as DEAE; chromatofocusing; SDS-PAGE; ammonium sulfate precipitation; and gel filtration using, e.g., Sephadex G-75. Various methods of protein purification may be employed and such methods are known in the art and described e.g. in Deutscher, 1990; Scopes, 1982. The purification step(s) selected will depend, e.g., on the nature of the production process used and the particular protein produced.

V. UTILITY OF CBH1 AND CBH1

It can be appreciated that the variant CBH1.1, a *H. jecorina* CBH1 variant or a *S. thermophilium* CBH1 cellulase nucleic acids, the variant CBH1.1, a *H. jecorina* CBH1 variant or a *S. thermophilium* CBH1 cellulase protein and compositions comprising variant CBH1.1, a *H. jecorina* CBH1 variant or a *S. thermophilium* CBH1 cellulase protein activity find utility in a wide variety applications, some of which are described below.

New and improved cellulase compositions that comprise varying amounts of a variant CBH1.1, a *H. jecorina* CBH1 variant or a *S. thermophilium* CBH1 cellulase find utility in detergent compositions that exhibit enhanced cleaning ability, function as a softening agent and/or improve the feel of cotton fabrics (e.g., "stone washing" or "biopolishing"), in compositions for degrading wood pulp into sugars (e.g., for bio-ethanol production), and/or in feed compositions. The isolation and characterization of cellulase of each type provides the ability to control the aspects of such compositions.

Variant CBH1.1, *H. jecorina* CBH1 variant or *S. thermophilium* CBH1 cellulases with decreased thermostability find uses, for example, in areas where the enzyme activity is required to be neutralized at lower temperatures so that other enzymes that may be present are left unaffected. In addition, the enzymes may find utility in the limited conversion of cellulosics, for example, in controlling the degree of crystallinity or of cellulosic chain-length. After reaching the desired extent of conversion the saccharifying temperature can be raised above the survival temperature of the de-stabilized CBH1.1, a *H. jecorina* CBH1 variant or a *S. thermophilium* CBH1. As the CBH1 activity is essential for hydrolysis of crystalline cellulose, conversion of crystalline cellulose will cease at the elevated temperature.

In one approach, the variant CBH1.1, a *H. jecorina* CBH1 variant or a *S. thermophilium* CBH1 cellulase of the invention finds utility in detergent compositions or in the treatment of fabrics to improve the feel and appearance.

Since the rate of hydrolysis of cellulosic products may be increased by using a transformant having at least one additional copy of the variant CBH1.1, a *H. jecorina* CBH1 variant or a *S. thermophilium* CBH1 cellulase gene, either as a replicative plasmid or inserted into the genome, products that contain cellulose or heteroglycans can be degraded at a faster rate and to a greater extent. Products made from cellulose such as paper, cotton, cellulosic diapers and the like can be degraded more efficiently in a landfill. Thus, the fermentation product obtainable from the transformants or the transformants alone may be used in compositions to help degrade by liquefaction a variety of cellulose products that add to the overcrowded landfills.

Separate saccharification and fermentation is a process whereby cellulose present in biomass, e.g., corn stover, is converted to glucose and subsequently yeast strains convert glucose into ethanol. Simultaneous saccharification and fermentation is a process whereby cellulose present in biomass, e.g., corn stover, is converted to glucose and, at the same time and in the same reactor, yeast strains convert glucose into ethanol. Thus, in another approach, the desired cellulase of the invention finds utility in the degradation of biomass to ethanol. Ethanol production from readily available sources of cellulose provides a stable, renewable fuel source.

Cellulose-based feedstocks are comprised of agricultural wastes, grasses and woods and other low-value biomass such as municipal waste (e.g., recycled paper, yard clippings, etc.). Ethanol may be produced from the fermentation of any of these cellulosic feedstocks. However, the cellulose must first be converted to sugars before there can be conversion to ethanol. Thus, the CBH1 cellulase described herein find use in the conversion of biomass to sugars.

A large variety of feedstocks may be used with the inventive variant CBH1.1, a *H. jecorina* CBH1 variant or a *S. thermophilium* CBH1 cellulase(s) and the one selected for use may depend on the region where the conversion is being done. For example, in the Midwestern United States agricultural wastes such as wheat straw, corn stover and bagasse may predominate while in California rice straw may predominate. However, it should be understood that any available cellulosic biomass may be used in any region.

A cellulase composition containing an enhanced amount of cellobiohydrolase finds utility in ethanol production. Ethanol from this process can be further used as an octane enhancer or directly as a fuel in lieu of gasoline which is advantageous because ethanol as a fuel source is more environmentally friendly than petroleum derived products. It is known that the use of ethanol will improve air quality and possibly reduce local ozone levels and smog. Moreover, utilization of ethanol in lieu of gasoline can be of strategic importance in buffering the impact of sudden shifts in non-renewable energy and petro-chemical supplies.

Ethanol can be produced via saccharification and fermentation processes from cellulosic biomass such as trees, herbaceous plants, municipal solid waste and agricultural and forestry residues. However, the ratio of individual cellulase enzymes within a naturally occurring cellulase mixture produced by a microbe may not be the most efficient for rapid conversion of cellulose in biomass to glucose. It is known that endoglucanases act to produce new cellulose chain ends which themselves are substrates for the action of cellobiohydrolases and thereby improve the efficiency of hydrolysis of the entire cellulase system. Therefore, the use of increased or optimized cellobiohydrolase activity may greatly enhance the production of ethanol.

Thus, the inventive cellobiohydrolase(s) finds use in the hydrolysis of cellulose to its sugar components. In one embodiment, a variant CBH1.1, a *H. jecorina* CBH1 variant or a *S. thermophilium* CBH1 cellulase is added to the biomass prior to the addition of a fermentative organism. In a second embodiment, a variant CBH1.1, a *H. jecorina* CBH1 variant or a *S. thermophilium* CBH1 cellulase is added to the biomass at the same time as a fermentative organism. Optionally, there may be other cellulase components present in either embodiment. Enhanced cellulose conversion may be achieved at higher temperatures using the CBH1 polypeptides described herein.

In another embodiment the cellulosic feedstock may be pretreated. Pretreatment may be by elevated temperature and the addition of either of dilute acid, concentrated acid or dilute alkali solution. The pretreatment solution is added for a time sufficient to at least partially hydrolyze the hemicellulose components and then neutralized.

The detergent compositions of this invention may employ besides the cellulase composition (irrespective of the cellobiohydrolase content, i.e., cellobiohydrolase-free, substantially cellobiohydrolase-free, or cellobiohydrolase enhanced), a surfactant, including anionic, non-ionic and ampholytic surfactants, a hydrolase, building agents, bleaching agents, bluing agents and fluorescent dyes, caking inhibitors, solubilizers, cationic surfactants and the like. All of these components are known in the detergent art. The cellulase composition as described above can be added to the detergent composition either in a liquid diluent, in granules, in emulsions, in gels, in pastes, and the like. Such forms are well known to the skilled artisan. When a solid detergent composition is employed, the cellulase composition is preferably formulated as granules. Preferably, the granules can be formulated so as to contain a cellulase protecting agent. For a more thorough discussion, see U.S. Pat. No. 6,162,782 entitled "Detergent compositions containing cellulase compositions deficient in CBH1 type components," which is incorporated herein by reference.

Preferably the cellulase compositions are employed from about 0.00005 weight percent to about 5 weight percent relative to the total detergent composition. More preferably, the cellulase compositions are employed from about 0.0002 weight percent to about 2 weight percent relative to the total detergent composition.

In addition the desired cellulase nucleic acid sequence finds utility in the identification and characterization of related nucleic acid sequences. A number of techniques useful for determining (predicting or confirming) the function of related genes or gene products include, but are not limited to, (A) DNA/RNA analysis, such as (1) overexpression, ectopic expression, and expression in other species; (2) gene knock-out (reverse genetics, targeted knock-out, viral induced gene silencing (VIGS, see Baulcombe, 1999); (3) analysis of the methylation status of the gene, especially flanking regulatory regions; and (4) in situ hybridization; (B) gene product analysis such as (1) recombinant protein expression; (2) antisera production, (3) immunolocalization; (4) biochemical assays for catalytic or other activity; (5) phosphorylation status; and (6) interaction with other proteins via yeast two-hybrid analysis; (C) pathway analysis, such as placing a gene or gene product within a particular biochemical or signaling pathway based on its overexpression phenotype or by sequence homology with related genes; and (D) other analyses which may also be performed to determine or confirm the participation of the isolated gene and its product in a particular metabolic or signaling pathway, and help determine gene function.

EXAMPLES

The present invention is described in further detail in the following examples which are not in any way intended to limit the scope of the invention as claimed. The attached Figures are meant to be considered as integral parts of the specification and description of the invention. All references cited are herein specifically incorporated by reference for all that is described therein.

Example 1

Identification of CBH1.1 Variants

This example illustrates the isolation and characterization of the nucleic acid encoding a variant *H. grisea* CBH1.1.

Isolation of Genomic DNA

Genomic DNA may be isolated using any method known in the art. In this set of experiments a sample of *Humicola grisea* var *thermoidea* (CBS 225.63) was obtained. However, the following protocol may be used:

Cells are grown at 45° C. in 20 ml Potato Dextrose Broth (PDB) for 24 hours. The cells are diluted 1:20 in fresh PDB medium and grown overnight. Two milliliters of cells are centrifuged and the pellet washed in 1 ml KC (60 g KCl, 2 g citric acid per liter, pH adjusted to 6.2 with 1M KOH). The cell pellet is resuspended in 900 µl KC. 100 µl (20 mg/ml) Novozyme® is added, mixed gently and the protoplastation followed microscopically at 37° C. until greater than 95% protoplasts are formed for a maximum of 2 hours. The cells are centrifuged at 1500 rpm (460 g) for 10 minutes. 200 µl TES/SDS (10 mM Tris, 50 mM EDTA, 150 mM NaCl, 1% SDS) is added, mixed and incubated at room temperature for 5 minutes. DNA is isolated using a Qiagen mini-prep isolation kit (Qiagen). The column is eluted with 100 µl milli-Q water and the DNA collected.

This is the method used for the isolation of genomic DNA of *H. grisea* var *thermoidea* from PDA plates grown at 45° C. An alternative method using the FastPrep® method may be desirable. The system consists of the FastPrep® Instrument as well as FastPrep® kits for nucleic acid isolation. FastPrep® is available from Qbiogene, Inc, Qbiogene, Inc., 2251 Rutherford Road, Carlsbad, Calif. 92008.

Construction of Primers

PCR was performed on a standard PCR machine such as the PTC-200 Peltier Thermal Cycler from MJ Research Inc. under the following conditions:

1) 1 minute at 96° C. for 1 cycle
2) 30 seconds at 94° C.
   60 seconds at 55° C.
   2 minutes at 72° C.
3) Repeat step 2 for 30 cycles
4) 7 minutes at 72° C. for 1 cycle, and
5) lower temperature to 15° C. for storage and further analysis.

The following DNA primers were constructed for use in amplification of homologous CBH1 genes from genomic DNA's isolated from various microorganisms. All symbols used herein for protein and DNA sequences correspond to IUPAC IUB Biochemical Nomenclature Commission codes.

Homologous 5' (PVS203) and 3' (PVS204) primers were developed based on the sequence of CBH1 from *Humicola grisea* var *thermoidea* (IFO9854) This strain expresses the sequence given in the alignment figure as D63515 (FIG. 5). Both primers contained Gateway cloning sequences from Invitrogen® at the 5' of the primer. Primer PVS203 contained attB1 sequence and primer PVS204 contained attB2 sequence.

```
Sequence of PVS203 without the attB1:
5' ATGCGTACCGCCAAGTTCGC 3'
(signal sequence of CBH1)

Sequence of PVS204 without the attB2:
5' TTACAGGCACTGAGAGTACCAG 3'
(cellulose binding module of CBH1)
```

PCR conditions were as follows: 20 µL of 5× reaction buffer (5× reaction buffer comprising 50 mM Tris HCl, pH 8.5; 87.5 mM $(NH_4)_2SO_4$; 6.25 mM $MgCL_2$; 2.5% Teen20 (v/v) 7.5% DMSO (v/v)); 0.2 mM each of dATP, dTTP, dGTP, dCTP (final concentration), 1 µL of 100 ng/µL genomic DNA, 1 µL of Tgo polymerase (Roche diagnostics GmbH, Cat#3186199) at 1 unit per µL, 0.2 µM of each primer, PVS203 and PVS204, (final concentration), and water to 100 µL.

Isolation of Variant *H. Grisea* CBH1.1 Gene Sequence

The full length sequence was obtained directly by using the N terminal (PVS203) and C terminal (PVS204) primers. The full length DNA sequence was translated into three open reading frames using Vector NTI software. Comparison of DNA and protein sequences to two known sequences for *H. grisea* Cel7A (X17258 and D63515) were performed to identify any putative intron sequences. Translation of the genomic DNA sequence without the intron sequences revealed the protein sequence of the variant *H. grisea* CBH1.1. The full length gene has been obtained and is provided in FIG. 1 (genomic DNA). The putative cDNA is presented in FIG. 2.

Example 2

Expression of CBH1.1 Variants

The following example details how the expression of the variant *H. grisea* CBH1.1 gene was performed.

The full-length gene from Example 1 were transferred to the *A. niger* Gateway compatible destination vector, which was developed by Genencor. This vector was built by using the pRAX1 as a backbone, shown in FIG. 6, according to the manual given in Gateway™ Cloning Technology: version 1 page 34-38.

The newly developed expression vector is shown in FIG. 7; this is a product of transferring the new gene into the destination vector pRAXdes2. This resulted in the final expression vectors called pRAXdesCBH1.1 (see FIG. 8).

The construct has been transformed into *A. niger* var. *awamori* according to the method described by Cao et al (Cao Q-N, Stubbs M, Ngo K Q P, Ward M, Cunningham A, Pai E F, Tu G-C and Hofmann T (2000) Penicillopepsin-JT2 a recombinant enzyme from *Penicillium janthinellum* and contribution of a hydrogen bond in subsite S3 to kcat Protein Science 9:991-1001).

Transformants were streaked on minimal medium plates (Ballance D J, Buxton F P, and Turner G (1983) Transformation of *Aspergillus nidulans* by the orotidine-5'-phosphate decarboxylase gene of *Neurospora crassa* Biochem Biophys Res Commun 112:284-289) and grown for 4 days at 30° C. Spores were collected using methods well known in the art (See <www.fgsc.net/fgn48/Kaminskyj.htm>). *A. nidulans* conidia are harvested in water (by rubbing the surface of a conidiating culture with a sterile bent glass rod to dislodge the spores) and can be stored for weeks to months at 4° C. without a serious loss of viability. However, freshly harvested spores germinate more reproducibly. For long-term storage, spores can be stored in 50% glycerol at −20° C., or in 15-20% glycerol at −80° C. Glycerol is more easily pipetted as an 80% solution in water. 800 µl of aqueous conidial suspension (as made for 4° C. storage) added to 200 µl 80% glycerol is used for a −80° C. stock; 400 µl suspension added to 600 µl 80% glycerol is used for a −20° C. stock. Vortex before freezing. For mutant collections, small pieces of conidiating cultures can be excised and placed in 20% glycerol, vortexed, and frozen as −80° C. stocks. In our case we store them in 50% glycerol at −80° C.

*A. niger* var *awamori* transformants were grown on minimal medium lacking uridine (Ballance et al. 1983). Transformants were screened for cellulase activity by inoculating 1 cm² of spore suspension from the sporulated grown agar plate into 100 ml shake flasks for 3 days at 37° C. as described by Cao et al. (2000).

The CBHI activity assay is based on the hydrolysis of the nonfluorescent 4-methylumbelliferyl-β-lactoside to the products lactose and 7-hydroxy-4-methylcoumarin, the latter product is responsible for the fluorescent signal. Pipette 170 µl 50 mM NaAc buffer pH 4.5 in a 96-well microtiter plate (MTP) (Greiner, Fluotrac 200, art. nr. 655076) suitable for fluorescence. Add 10 µl of supernatant and then add 10 µl of MUL (1 mM 4-methylumbelliferyl-β-lactoside (MUL) in milliQ water) and put the MTP in the Fluostar Galaxy (BMG Labtechnologies; D-77656 Offenburg). Measure the kinetics for 16 min. (8 cycles of 120 s each) using $\lambda_{320\ nm}$ (excitation) and $\lambda_{460\ nm}$ (emission) at 50° C. Supernatants having CBH1 activity were then subjected to Hydrophobic Interaction Chromatography as described in Example 3 below.

The amino acid sequences were deduced as stated above in Example 1. The amino acid sequence of the variant CBH1.1 is shown in FIG. 3 with a signal sequence, and in FIG. 4 without a signal sequence. The signal sequence is shown in FIG. 3 in bold and underlined font.

Example 3

Thermostability of CBH1 Variants

The following example details how the variant *H. grisea* CBH1.1 differs in thermostability from a *T. reesei* CBH1 cellulase enzyme.

CBH I cellulase variants were cloned and expressed as above (see Example 2). Cel7A wild type and variants were then purified from cell-free supernatants of these cultures by column chromatography. Proteins were purified using hydrophobic interaction chromatography (HIC). Columns were run on a BioCAD® Sprint Perfusion Chromatography System using Poros® 20 HP2 resin both made by Applied Biosystems.

HIC columns were equilibrated with 5 column volumes of 0.020 M sodium phosphate, 0.5 M ammonium sulfate at pH 6.8. Ammonium sulfate was added to the supernatants to a final concentration of approximately 0.5 M and the pH was adjusted to 6.8. After filtration, the supernatant was loaded onto the column. After loading, the column was washed with 10 column volumes of equilibration buffer and then eluted with a 10 column volume gradient from 0.5 M ammonium sulfate to zero ammonium sulfate in 0.02 M sodium phosphate pH 6.8. Cel7A was eluted approximately mid-gradient. Fractions were collected and pooled on the basis of reduced, SDS-PAGE gel analysis.

The melting points were determined according to the methods of Luo, et al., *Biochemistry* 34:10669 and Gloss, et al., *Biochemistry* 36:5612.

Data was collected on the Aviv 215 circular dichroism spectrophotometer. Spectra of the variants between 210 and 260 nanometers were taken at 25° C. Buffer conditions were 50 mM Bis Tris Propane/50 mM ammonium acetate/glacial acetic acid at pH 5.5. The protein concentration was kept between 0.25 and 0.5 mgs/mL. After determining the optimal wavelength to monitor unfolding, the samples were thermally denatured by ramping the temperature from 25° C. to 75° C. under the same buffer conditions. Data was collected for 5 seconds every 2 degrees. Partially reversible unfolding was monitored at 230 nanometers in an 0.1 centimeter path length cell.

The variant *H. grisea* CBH 1.1 cellulase has an enhanced thermostability profile as compared wild type *T. reesei* CBH1. The variant *H. grisea* CBH1.1 has a Tm of 72.5° C.; *T. reesei* has a Tm of 62.3° C.

Example 4

Activity of CBH1 Variants

The following example details how the activity of the *H. grisea* CBH1.1 variant was evaluated.

Cellulose conversion was evaluated by techniques known in the art. See, for example, Baker et al, Appl Biochem Biotechnol 1998 Spring; 70-720:395-403.

A standard cellulosic conversion assay was used in the experiments. In this assay enzyme and buffered substrate were placed in containers and incubated at a temperature over time. The reaction was quenched with enough 100 mM Glycine, pH 11.0 to bring the pH of the reaction mixture to at least pH10. Once the reaction was quenched, an aliquot of the reaction mixture was filtered through a 0.2 micron membrane to remove solids. The filtered solution was then assayed for soluble sugars by HPLC according to the methods described in Baker et al., Appl. Biochem. Biotechnol. 70-72:395-403 (1998).

Pretreated Corn Stover (PCS)—

Corn stover was pretreated with 2% w/w $H_2SO_4$ as described in Schell, D. et al., J. Appl. Biochem. Biotechnol. 105:69-86 (2003) and followed by multiple washes with deionized water to obtain a pH of 4.5. Sodium acetate was added to make a final concentration of 50 mM and this was titrated to pH 5.0. The cellulose concentration in the reaction mixture was approximately 7%.

Phosphoric Acid Swollen Cellulose (PASC)—

PASC was prepared from Avicel according to the method described in Walseth (1971) Tappi 35: 228 (1971) and Wood Biochem J. 121:353 (1971). This material was diluted with buffer and water to achieve a 0.63% w/v mixture such that the final concentration of sodium acetate was 50 mM, pH 5.0. The enzymes were dosed at 1.6 mg of total protein per gram of cellulose.

The first set of experiments examined the percent conversion at 38° C. for 1 day on 12.66% pretreated corn stover (PCS) (see Schell, D. et al., J. Appl. Biochem. Biotechnol. (2003) 105:69-86) using 15.5 mg enzyme/gm cellulose. Samples were agitated at 700 rpm. Comparisons were made between: 1) a cellulase from a CBH1 deleted *Trichoderma* strain (delCBH1); 2) an *A. niger* strain that had a *T. reesei* CBH1 gene inserted (rCBH1); 3) an *A. niger* strain overexpressing its native CBHB (Aniger); 4) an *A. niger* strain that had a *H. schweinitzii* CBH1 gene inserted (Hschweinitzii/An); 5) an *A. niger* strain that had a *T. pseudokoningii* CBH1 gene inserted (Tpseudokoni/An); 6) an *A. niger* strain that had a *H. grisea* variant CBH1.1 gene inserted (Hgrisea/An-1); 7) an *A. niger* strain that had a *H. grisea* variant CBH1.1 gene inserted (Hgrisea/An-2). Hgrisea/An-1 and Hgrisea/An-2 are two clones from the same transformation of *A. niger* with the *H. grisea* variant CBH1.1 gene. The results from the first set of experiments are presented in FIG. 9. As can be seen, the *H. grisea* variant CBH1.1 does not out perform any of the other CBH's tested. FIG. 11 is a comparison of the *H. grisea* variant CBH1.1 against the *T. reesei* nCBH1 results from the same experimental conditions.

The second set of experiments examined the percent conversion under similar conditions as the first set except the incubation temperature was 65° C., not 38° C. Results for this set of experiments are presented in FIG. 10. As can be seen, the *H. grisea* variant CBH1.1 out performed the other CBH's tested. FIG. 12 is a comparison of the *H. grisea* variant CBH1.1 against the *T. reesei* rCBH1 results from the same experimental conditions.

The third set of experiments examined the rate of cellobiose generation from PASC under similar test conditions as the previous experiments; the temperatures used were 38° C., 65° C. and 70° C. Results are presented in FIG. 13. As can be seen, the *H. grisea* variant CBH1.1 out performed the *T. reesei* CBH1 at all temperatures tested.

Example 5

Isolation of *Scytalidium thermophilium* CBH1

This example illustrates the isolation and characterization of the nucleic acid encoding a *S. thermophilium* CBH1.
Isolation of Genomic DNA and Construction of Primers Methods for cloning, expressing and purifying the *Scytalidium thermophilum* CBHI were all as described for *Humicola grisea* var. *thermoidea* CBH1.1 (see Example 1). The CBHI gene from *Scytalidium thermophilum* was amplified from genomic DNA from public strain collection entry CBS 671.88, using the same PCR primers, PVS203 and PVS204, used to amplify the *Humicola grisea* var. *thermoidea* CBH1.1.
Isolation of *S. thermophilium* CBH1 Gene Sequence The full length sequence was obtained directly by using the N terminal (PVS203) and C terminal (PVS204) primers. The full length DNA sequence was translated into three open reading frames using Vector NTI software. Translation of the genomic DNA sequence without the intron sequences revealed the protein sequence of the *S. thermophilium* CBH1. The full length gene has been obtained and is provided in FIG. 14A (genomic DNA). The putative cDNA is presented in FIG. 14B. The amino acid sequence with and without signal sequence is provided in FIGS. 14C and 15, respectively.

The *S. thermophilium* CBH1, *Humicola grisea* var. *thermoidea* CBH1.1 and *H. jecorina* CBH1 protein sequences were aligned. See FIG. 15.

By identifying sites of difference between *Humicola grisea* var. *thermoidea* CBH1.1 and the significantly more stable *Scytalidium thermophilum* CBHI, and then using the alignment in FIG. 15 to identify the corresponding site in *Hypocrea jecorina* CBHI, which is much less stable than either *Humicola grisea* var. *thermoidea* CBH1.1 or *Scytalidium thermophilum* CBHI.) The following sites in *Hypocrea jecorina* CBHI (mature protein residue numbering) are identified as being important for stability:

Thr(T)55, preferably Thr55Glu (T55E) & Thr55Lys (T55K)

Ser(S)58, preferably Ser58Thr (S58T)

Gln(Q)101, preferably Gln101Tyr (Q101Y) & Gln101His (Q101H)

Asn(N)250, preferably Asn250Asp (N250D) & Asn250Glu (N250E)

Pro(P)265, preferably Pro265Ala (P265A) & Pro265Ser (P265S)

Leu(L)288, preferably Leu288Ile (L288I).

Example 6

Thermostability of *Scytalidium thermophilium* CBH1

This example describes the thermostability measurement of *S. thermophilum* CBH1 and *H. grisea* var. *thermoidea* CBH1.1.

*S. thermophilum* CBH1 and *H. grisea* var. *thermoidea* CBH1.1 were expressed using the methods as in Example 2, purified as in Example 3 and analyzed by differential scanning calorimetry using a Microcal VP-DSC. Samples were scanned from 30 to 95 degrees C. at 90 degrees C./hour. The purified proteins were desalted into 50 mM ammonium acetate and 50 m M bistris propane at pH 5.5. The final protein concentration was between 0.05 and 0.25 mg/mL for all samples.

The thermal transition observed for *S. thermophilum* CBHI had a midpoint of 78.3 degrees C. *H. grisea* CBH1.1 has a transition with a midpoint of 76.0 degrees C. See FIG. 16.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A polynucleotide encoding a cellobiohydrolase comprising (i) an amino acid sequence that is at least 85% identical to SEQ ID NO:10 and (ii) at least one substitution at a position corresponding to T55, Q101, N250, P265, or L288 of SEQ ID NO:10, wherein the substitution at the position corresponding to T55 is T55K and the substitution at the position corresponding to Q101 is Q101Y or Q101H.

2. The polynucleotide of claim 1, wherein the cellobiohydrolase comprises one or more substitutions selected from the group consisting of N250D, N250E, P265A, P265S, and L288I.

3. A nucleic acid construct comprising the polynucleotide according to claim 1, operably linked to one or more control sequences.

4. A recombinant expression vector comprising the nucleic acid construct of claim 3.

5. A recombinant host cell comprising the nucleic acid construct of claim 3.

6. A method for producing a CBH1 polypeptide, said method comprising:

a) transforming a host cell with the nucleic acid construct of claim 3;

b) culturing the host cell under conditions to produce the polypeptide; and c) recovering the polypeptide.

7. The polynucleotide of claim 1, wherein the cellobiohydrolase comprises an amino acid sequence that is at least 90% identical to SEQ ID NO:10.

8. The polynucleotide of claim 7, wherein the cellobiohydrolase comprises an amino acid sequence that is at least 95% identical to SEQ ID NO:10.

9. A method of converting biomass to sugars comprising contacting the biomass with a cellobiohydrolase encoded by the polynucleotide of claim 1.

* * * * *

SEQUENCE LISTING

```
<160> NUMBER OF SEQ ID NOS: 15

<210> SEQ ID NO 1
<211> LENGTH: 1638
<212> TYPE: DNA
<213> ORGANISM: Humicola grisea

<400> SEQUENCE: 1
atgcgtaccg ccaagttcgc cacccctcgcc gcccttgtgg cctcggccgc cgcccagcag      60
gcgtgcagtc tcaccaccga gaggcaccct tccctctctt ggaagaagtg caccgccggc     120
ggccagtgcc agaccgtcca ggcttccatc actctcgact ccaactggcg ctggactcac     180
caggtgtctg gctccaccaa ctgctacacg ggcaacaagt gggatactag catctgcact     240
gatgccaagt cgtgcgctca gaactgctgc gtcgatggtg ccgactacac cagcacctat     300
ggcatcacca ccaacggtga ttccctgagc ctcaagttcg tcaccaaggg ccagcactcg     360
accaacgtcg gctcgcgtac ctacctgatg gacggcgagg acaagtatca gagtacgttc     420
```

```
tatcttcagc cttctcgcgc cttgaatcct ggctaacgtt tacacttcac agccttcgag    480
ctcctcggca acgagttcac cttcgatgtc gatgtctcca acatcggctg cggtctcaac    540
ggcgccctgt acttcgtctc catggacgcc gatggtggtc tcagccgcta tcctggcaac    600
aaggctggtg ccaagtacgg taccggctac tgcgatgctc agtgccccg tgacatcaag    660
ttcatcaacg gcgaggccaa cattgagggc tggaccggct ccaccaacga ccccaacgcc    720
ggcgcgggcc gctatggtac ctgctgctct gagatggata tctgggaagc caacaacatg    780
gctactgcct tcactcctca cccttgcacc atcattggcc agagccgctg cgagggcgac    840
tcgtgcggtg gcacctacag caacgagcgc tacgccggcg tctgcgaccc cgatggctgc    900
gacttcaact cgtaccgcca gggcaacaag accttctacg gcaagggcat gaccgtcgac    960
accaccaaga gatcactgt cgtcacccag ttcctcaagg atgccaacgg cgatctcggc   1020
gagatcaagc gcttctacgt ccaggatggc aagatcatcc ccaactccga gtccaccatc   1080
cccggcgtcg agggcaattc catcacccag gactggtgcg accgcagaa ggttgccttt   1140
ggcgacattg acgacttcaa ccgcaagggc ggcatgaagc agatgggcaa ggccctcgcc   1200
ggccccatgt cctggtcat gtccatctgg gatgaccacg cctccaacat gctctggctc   1260
gactcgacct ccctgtcga tgccgctggc aagcccggcg ccgagcgcgg tgcctgcccg   1320
accacctcgg gtgtccctgc tgaggttgag gccgaggccc caacagcaa cgtcgtcttc   1380
tccaacatcc gcttcggccc catcggctcg accgttgctg gtctccccgg cgcgggcaac   1440
ggcggcaaca acggcggcaa ccccccgccc cccaccacca ccacctcctc ggctccggcc   1500
accaccacca ccgccagcgc tggccccaag gctggccgct ggcagcagtg cggcggcatc   1560
ggcttcactg gcccgaccca gtgcgaggag ccctacactt gcaccaagct caacgactgg   1620
tactctcagt gcctgtaa                                                  1638
```

<210> SEQ ID NO 2
<211> LENGTH: 1323
<212> TYPE: DNA
<213> ORGANISM: Humicola grisea

<400> SEQUENCE: 2

```
gctcagaact gctgcgtcga tggtgccgac tacaccagca cctatggcat caccaccaac     60
ggtgattccc tgagcctcaa gttcgtcacc aagggccagc actcgaccaa cgtcggctcg    120
cgtacctacc tgatggacgg cgaggacaag tatcagacct tcgagctcct cggcaacgag    180
ttcacctttcg atgtcgatgt ctccaacatc ggctgcggtc tcaacggcgc cctgtacttc    240
gtctccatgg acgccgatgg tggtctcagc cgctatcctg caacaaggc tggtgccaag    300
tacggtaccg gctactgcga tgctcagtgc cccgtgaca tcaagttcat caacggcgag    360
gccaacattg agggctggac cggctccacc aacgacccca cgccggcgc gggccgctat    420
ggtacctgct gctctgagat ggatatctgg gaagccaaca catggctac tgccttcact    480
cctcacccctt gcaccatcat tggccagagc cgctgcgagg gcgactcgtg cggtggcacc    540
tacagcaacg agcgctacgc cggcgtctgc gaccccgatg gctgcgactt caactcgtac    600
cgccagggca acaagacctt ctacggcaag ggcatgaccg tcgacaccac caagaagatc    660
actgtcgtca cccagttcct caaggatgcc aacggcgatc tcggcgagat caagcgcttc    720
tacgtccagg atggcaagat catccccaac tccgagtcca catcccccgg cgtcgagggc    780
aattccatca cccaggactg gtgcgaccgc cagaaggttg cctttggcga cattgacgac    840
```

```
ttcaaccgca agggcggcat gaagcagatg ggcaaggccc tcgccggccc catggtcctg    900
gtcatgtcca tctgggatga ccacgcctcc aacatgctct ggctcgactc gaccttccct    960
gtcgatgccg ctggcaagcc cggcgccgag cgcggtgcct gcccgaccac ctcgggtgtc   1020
cctgctgagg ttgaggccga ggcccccaac agcaacgtcg tcttctccaa catccgcttc   1080
ggccccatcg gctcgaccgt tgctggtctc cccggcgcgg gcaacggcgg caacaacggc   1140
ggcaaccccc cgcccccccac caccaccacc tcctcggctc cggccaccac caccaccgcc   1200
agcgctggcc ccaaggctgg ccgctggcag cagtgcggcg gcatcggctt cactggcccg   1260
acccagtgcg aggagcccta cacttgcacc aagctcaacg actggtactc tcagtgcctg   1320
taa                                                                 1323
```

<210> SEQ ID NO 3
<211> LENGTH: 525
<212> TYPE: PRT
<213> ORGANISM: Humicola grisea

<400> SEQUENCE: 3

```
Met Arg Thr Ala Lys Phe Ala Thr Leu Ala Ala Leu Val Ala Ser
 1               5                  10                  15

Ala Ala Gln Gln Ala Cys Ser Leu Thr Thr Glu Arg His Pro Ser Leu
                20                  25                  30

Ser Trp Lys Lys Cys Thr Ala Gly Gly Gln Cys Gln Thr Val Gln Ala
            35                  40                  45

Ser Ile Thr Leu Asp Ser Asn Trp Arg Trp Thr His Gln Val Ser Gly
        50                  55                  60

Ser Thr Asn Cys Tyr Thr Gly Asn Lys Trp Asp Thr Ser Ile Cys Thr
65                  70                  75                  80

Asp Ala Lys Ser Cys Ala Gln Asn Cys Cys Val Asp Gly Ala Asp Tyr
                85                  90                  95

Thr Ser Thr Tyr Gly Ile Thr Thr Asn Gly Asp Ser Leu Ser Leu Lys
            100                 105                 110

Phe Val Thr Lys Gly Gln His Ser Thr Asn Val Gly Ser Arg Thr Tyr
        115                 120                 125

Leu Met Asp Gly Glu Asp Lys Tyr Gln Thr Phe Glu Leu Leu Gly Asn
    130                 135                 140

Glu Phe Thr Phe Asp Val Asp Val Ser Asn Ile Gly Cys Gly Leu Asn
145                 150                 155                 160

Gly Ala Leu Tyr Phe Val Ser Met Asp Ala Asp Gly Gly Leu Ser Arg
                165                 170                 175

Tyr Pro Gly Asn Lys Ala Gly Ala Lys Tyr Gly Thr Gly Tyr Cys Asp
            180                 185                 190

Ala Gln Cys Pro Arg Asp Ile Lys Phe Ile Asn Gly Glu Ala Asn Ile
        195                 200                 205

Glu Gly Trp Thr Gly Ser Thr Asn Asp Pro Asn Ala Gly Ala Gly Arg
    210                 215                 220

Tyr Gly Thr Cys Cys Ser Glu Met Asp Ile Trp Glu Ala Asn Asn Met
225                 230                 235                 240

Ala Thr Ala Phe Thr Pro His Pro Cys Thr Ile Ile Gly Gln Ser Arg
                245                 250                 255

Cys Glu Gly Asp Ser Cys Gly Gly Thr Tyr Ser Asn Glu Arg Tyr Ala
            260                 265                 270

Gly Val Cys Asp Pro Asp Gly Cys Asp Phe Asn Ser Tyr Arg Gln Gly
        275                 280                 285
```

```
Asn Lys Thr Phe Tyr Gly Lys Gly Met Thr Val Asp Thr Lys Lys
    290                 295                 300

Ile Thr Val Val Thr Gln Phe Leu Lys Asp Ala Asn Gly Asp Leu Gly
305                 310                 315                 320

Glu Ile Lys Arg Phe Tyr Val Gln Asp Gly Lys Ile Ile Pro Asn Ser
                325                 330                 335

Glu Ser Thr Ile Pro Gly Val Glu Gly Asn Ser Ile Thr Gln Asp Trp
                340                 345                 350

Cys Asp Arg Gln Lys Val Ala Phe Gly Asp Ile Asp Asp Phe Asn Arg
                355                 360                 365

Lys Gly Gly Met Lys Gln Met Gly Lys Ala Leu Ala Gly Pro Met Val
            370                 375                 380

Leu Val Met Ser Ile Trp Asp Asp His Ala Ser Asn Met Leu Trp Leu
385                 390                 395                 400

Asp Ser Thr Phe Pro Val Asp Ala Ala Gly Lys Pro Gly Ala Glu Arg
                405                 410                 415

Gly Ala Cys Pro Thr Thr Ser Gly Val Pro Ala Glu Val Glu Ala Glu
                420                 425                 430

Ala Pro Asn Ser Asn Val Val Phe Ser Asn Ile Arg Phe Gly Pro Ile
            435                 440                 445

Gly Ser Thr Val Ala Gly Leu Pro Gly Ala Gly Asn Gly Gly Asn Asn
450                 455                 460

Gly Gly Asn Pro Pro Pro Thr Thr Thr Ser Ser Ala Pro Ala
465                 470                 475                 480

Thr Thr Thr Thr Ala Ser Ala Gly Pro Lys Ala Gly Arg Trp Gln Gln
                485                 490                 495

Cys Gly Gly Ile Gly Phe Thr Gly Pro Thr Gln Cys Glu Glu Pro Tyr
                500                 505                 510

Thr Cys Thr Lys Leu Asn Asp Trp Tyr Ser Gln Cys Leu
            515                 520                 525

<210> SEQ ID NO 4
<211> LENGTH: 507
<212> TYPE: PRT
<213> ORGANISM: Humicola grisea

<400> SEQUENCE: 4

Gln Gln Ala Cys Ser Leu Thr Thr Glu Arg His Pro Ser Leu Ser Trp
  1               5                  10                  15

Lys Lys Cys Thr Ala Gly Gly Cys Gln Thr Val Gln Ala Ser Ile
                20                  25                  30

Thr Leu Asp Ser Asn Trp Arg Trp Thr His Gln Val Ser Gly Ser Thr
                35                  40                  45

Asn Cys Tyr Thr Gly Asn Lys Trp Asp Thr Ser Ile Cys Thr Asp Ala
            50                  55                  60

Lys Ser Cys Ala Gln Asn Cys Cys Val Asp Gly Ala Asp Tyr Thr Ser
65                  70                  75                  80

Thr Tyr Gly Ile Thr Thr Asn Gly Asp Ser Leu Ser Leu Lys Phe Val
                85                  90                  95

Thr Lys Gly Gln His Ser Thr Asn Val Gly Ser Arg Thr Tyr Leu Met
                100                 105                 110

Asp Gly Glu Asp Lys Tyr Gln Thr Phe Glu Leu Leu Gly Asn Glu Phe
            115                 120                 125

Thr Phe Asp Val Asp Val Ser Asn Ile Gly Cys Gly Leu Asn Gly Ala
```

```
                130                 135                 140
Leu Tyr Phe Val Ser Met Asp Ala Asp Gly Gly Leu Ser Arg Tyr Pro
145                 150                 155                 160

Gly Asn Lys Ala Gly Ala Lys Tyr Gly Thr Gly Tyr Cys Asp Ala Gln
                165                 170                 175

Cys Pro Arg Asp Ile Lys Phe Ile Asn Gly Glu Ala Asn Ile Glu Gly
                180                 185                 190

Trp Thr Gly Ser Thr Asn Asp Pro Asn Ala Gly Ala Gly Arg Tyr Gly
                195                 200                 205

Thr Cys Cys Ser Glu Met Asp Ile Trp Glu Ala Asn Asn Met Ala Thr
                210                 215                 220

Ala Phe Thr Pro His Pro Cys Thr Ile Ile Gly Gln Ser Arg Cys Glu
225                 230                 235                 240

Gly Asp Ser Cys Gly Gly Thr Tyr Ser Asn Glu Arg Tyr Ala Gly Val
                245                 250                 255

Cys Asp Pro Asp Gly Cys Asp Phe Asn Ser Tyr Arg Gln Gly Asn Lys
                260                 265                 270

Thr Phe Tyr Gly Lys Gly Met Thr Val Asp Thr Thr Lys Lys Ile Thr
                275                 280                 285

Val Val Thr Gln Phe Leu Lys Asp Ala Asn Gly Asp Leu Gly Glu Ile
                290                 295                 300

Lys Arg Phe Tyr Val Gln Asp Gly Lys Ile Ile Pro Asn Ser Glu Ser
305                 310                 315                 320

Thr Ile Pro Gly Val Glu Gly Asn Ser Ile Thr Gln Asp Trp Cys Asp
                325                 330                 335

Arg Gln Lys Val Ala Phe Gly Asp Ile Asp Asp Phe Asn Arg Lys Gly
                340                 345                 350

Gly Met Lys Gln Met Gly Lys Ala Leu Ala Gly Pro Met Val Leu Val
                355                 360                 365

Met Ser Ile Trp Asp Asp His Ala Ser Asn Met Leu Trp Leu Asp Ser
370                 375                 380

Thr Phe Pro Val Asp Ala Ala Gly Lys Pro Gly Ala Glu Arg Gly Ala
385                 390                 395                 400

Cys Pro Thr Thr Ser Gly Val Pro Ala Glu Val Glu Ala Glu Ala Pro
                405                 410                 415

Asn Ser Asn Val Val Phe Ser Asn Ile Arg Phe Gly Pro Ile Gly Ser
                420                 425                 430

Thr Val Ala Gly Leu Pro Gly Ala Gly Asn Gly Gly Asn Asn Gly Gly
                435                 440                 445

Asn Pro Pro Pro Thr Thr Thr Thr Ser Ser Ala Pro Ala Thr Thr
450                 455                 460

Thr Thr Ala Ser Ala Gly Pro Lys Ala Gly Arg Trp Gln Gln Cys Gly
465                 470                 475                 480

Gly Ile Gly Phe Thr Gly Pro Thr Gln Cys Glu Glu Pro Tyr Thr Cys
                485                 490                 495

Thr Lys Leu Asn Asp Trp Tyr Ser Gln Cys Leu
                500                 505

<210> SEQ ID NO 5
<211> LENGTH: 507
<212> TYPE: PRT
<213> ORGANISM: Humicola grisea

<400> SEQUENCE: 5
```

```
Gln Gln Ala Cys Ser Leu Thr Thr Glu Arg His Pro Ser Leu Ser Trp
 1               5                  10                  15
Asn Lys Cys Thr Ala Gly Gly Gln Cys Gln Thr Val Gln Ala Ser Ile
            20                  25                  30
Thr Leu Asp Ser Asn Trp Arg Trp Thr His Gln Val Ser Gly Ser Thr
        35                  40                  45
Asn Cys Tyr Thr Gly Asn Lys Trp Asp Thr Ser Ile Cys Thr Asp Ala
 50                  55                  60
Lys Ser Cys Ala Gln Asn Cys Cys Val Asp Gly Ala Asp Tyr Thr Ser
 65                  70                  75                  80
Thr Tyr Gly Ile Thr Thr Asn Gly Asp Ser Leu Ser Leu Lys Phe Val
                    85                  90                  95
Thr Lys Gly Gln His Ser Thr Asn Val Gly Ser Arg Thr Tyr Leu Met
                100                 105                 110
Asp Gly Glu Asp Lys Tyr Gln Thr Phe Glu Leu Leu Gly Asn Glu Phe
            115                 120                 125
Thr Phe Asp Val Asp Val Ser Asn Ile Gly Cys Gly Leu Asn Gly Ala
        130                 135                 140
Leu Tyr Phe Val Ser Met Asp Ala Asp Gly Gly Leu Ser Arg Tyr Pro
145                 150                 155                 160
Gly Asn Lys Ala Gly Ala Lys Tyr Gly Thr Gly Tyr Cys Asp Ala Gln
                165                 170                 175
Cys Pro Arg Asp Ile Lys Phe Ile Asn Gly Glu Ala Asn Ile Glu Gly
                180                 185                 190
Trp Thr Gly Ser Thr Asn Asp Pro Asn Ala Gly Ala Gly Arg Tyr Gly
                195                 200                 205
Thr Cys Cys Ser Glu Met Asp Ile Trp Glu Ala Asn Asn Met Ala Thr
        210                 215                 220
Ala Phe Thr Pro His Pro Cys Thr Ile Ile Gly Gln Ser Arg Cys Glu
225                 230                 235                 240
Gly Asp Ser Cys Gly Gly Thr Tyr Ser Asn Glu Arg Tyr Ala Gly Val
                245                 250                 255
Cys Asp Pro Asp Gly Cys Asp Phe Asn Ser Tyr Arg Gln Gly Asn Lys
                260                 265                 270
Thr Phe Tyr Gly Lys Gly Met Thr Val Asp Thr Thr Lys Lys Ile Thr
                275                 280                 285
Val Val Thr Gln Phe Leu Lys Asp Ala Asn Gly Asp Leu Gly Glu Ile
        290                 295                 300
Lys Arg Phe Tyr Val Gln Asp Gly Lys Ile Ile Pro Asn Ser Glu Ser
305                 310                 315                 320
Thr Ile Pro Gly Val Glu Gly Asn Ser Ile Thr Gln Asp Trp Cys Asp
                325                 330                 335
Arg Gln Lys Val Ala Phe Gly Asp Ile Asp Asp Phe Asn Arg Lys Gly
                340                 345                 350
Gly Met Lys Gln Met Gly Lys Ala Leu Ala Gly Pro Met Val Leu Val
                355                 360                 365
Met Ser Ile Trp Asp Asp His Ala Ser Asn Met Leu Trp Leu Asp Ser
        370                 375                 380
Thr Phe Pro Val Asp Ala Ala Gly Lys Pro Gly Ala Glu Arg Gly Ala
385                 390                 395                 400
Cys Pro Thr Thr Ser Gly Val Pro Ala Glu Val Glu Ala Glu Ala Pro
                405                 410                 415
Asn Ser Asn Val Val Phe Ser Asn Ile Arg Phe Gly Pro Ile Gly Ser
```

```
            420                 425                 430
Thr Val Ala Gly Leu Pro Gly Ala Gly Asn Gly Gly Asn Asn Gly Gly
            435                 440                 445

Asn Pro Pro Pro Thr Thr Thr Ser Ser Ala Pro Ala Thr Thr
450                 455                 460

Thr Thr Ala Ser Ala Gly Pro Lys Ala Gly Arg Trp Gln Gln Cys Gly
465                 470                 475                 480

Gly Ile Gly Phe Thr Gly Pro Thr Gln Cys Glu Glu Pro Tyr Ile Cys
                485                 490                 495

Thr Lys Leu Asn Asp Trp Tyr Ser Gln Cys Leu
            500                 505

<210> SEQ ID NO 6
<211> LENGTH: 507
<212> TYPE: PRT
<213> ORGANISM: Humicola grisea

<400> SEQUENCE: 6

Gln Gln Ala Cys Ser Leu Thr Thr Glu Arg His Pro Ser Leu Ser Trp
1               5                   10                  15

Lys Lys Cys Thr Ala Gly Gly Gln Cys Gln Thr Val Gln Ala Ser Ile
            20                  25                  30

Thr Leu Asp Ser Asn Trp Arg Trp Thr His Gln Val Ser Gly Ser Thr
        35                  40                  45

Asn Cys Tyr Thr Gly Asn Lys Trp Asp Thr Ser Ile Cys Thr Asp Ala
50                  55                  60

Lys Ser Cys Ala Gln Asn Cys Cys Val Asp Gly Ala Asp Tyr Thr Ser
65                  70                  75                  80

Thr Tyr Gly Ile Thr Thr Asn Gly Asp Ser Leu Ser Leu Lys Phe Val
                85                  90                  95

Thr Lys Gly Gln Tyr Ser Thr Asn Val Gly Ser Arg Thr Tyr Leu Met
            100                 105                 110

Asp Gly Glu Asp Lys Tyr Gln Thr Phe Glu Leu Leu Gly Asn Glu Phe
        115                 120                 125

Thr Phe Asp Val Asp Val Ser Asn Ile Gly Cys Gly Leu Asn Gly Ala
    130                 135                 140

Leu Tyr Phe Val Ser Met Asp Ala Asp Gly Gly Leu Ser Arg Tyr Pro
145                 150                 155                 160

Gly Asn Lys Ala Gly Ala Lys Tyr Gly Thr Gly Tyr Cys Asp Ala Gln
                165                 170                 175

Cys Pro Arg Asp Ile Lys Phe Ile Asn Gly Glu Ala Asn Ile Glu Gly
            180                 185                 190

Trp Thr Gly Ser Thr Asn Asp Pro Asn Ala Gly Ala Gly Arg Tyr Gly
        195                 200                 205

Thr Cys Cys Ser Glu Met Asp Ile Trp Glu Ala Asn Asn Met Ala Thr
    210                 215                 220

Ala Phe Thr Pro His Pro Cys Thr Ile Ile Gly Gln Ser Arg Cys Glu
225                 230                 235                 240

Gly Asp Ser Cys Gly Gly Thr Tyr Ser Asn Glu Arg Tyr Ala Gly Val
                245                 250                 255

Cys Asp Pro Asp Gly Cys Asp Phe Asn Ser Tyr Arg Gln Gly Asn Lys
            260                 265                 270

Thr Phe Tyr Gly Lys Gly Met Thr Val Asp Thr Thr Lys Lys Ile Thr
        275                 280                 285
```

```
Val Val Thr Gln Phe Leu Lys Asp Ala Asn Gly Asp Leu Gly Glu Ile
    290                 295                 300

Lys Arg Phe Tyr Val Gln Asp Gly Lys Ile Ile Pro Asn Ser Glu Ser
305                 310                 315                 320

Thr Ile Pro Gly Val Glu Gly Asn Ser Ile Thr Gln Asp Trp Cys Asp
                325                 330                 335

Arg Gln Lys Val Ala Phe Gly Asp Ile Asp Asp Phe Asn Arg Lys Gly
            340                 345                 350

Gly Met Lys Gln Met Gly Lys Ala Leu Ala Gly Pro Met Val Leu Val
        355                 360                 365

Met Ser Ile Trp Asp Asp His Ala Ser Asn Met Leu Trp Leu Asp Ser
    370                 375                 380

Thr Phe Pro Val Asp Ala Ala Gly Lys Pro Gly Ala Glu Arg Gly Ala
385                 390                 395                 400

Cys Pro Thr Thr Ser Gly Val Pro Ala Glu Val Glu Ala Glu Ala Pro
                405                 410                 415

Asn Ser Asn Val Val Phe Ser Asn Ile Arg Phe Gly Pro Ile Gly Ser
            420                 425                 430

Thr Val Ala Gly Leu Pro Gly Ala Gly Asn Gly Gly Asn Asn Gly Gly
        435                 440                 445

Asn Pro Pro Pro Pro Thr Thr Thr Thr Ser Ser Ala Pro Ala Thr Thr
    450                 455                 460

Thr Thr Ala Ser Ala Gly Pro Lys Ala Gly Arg Trp Gln Gln Cys Gly
465                 470                 475                 480

Gly Ile Gly Phe Thr Gly Pro Thr Gln Cys Glu Glu Pro Tyr Thr Cys
                485                 490                 495

Thr Lys Leu Asn Asp Trp Tyr Ser Gln Cys Leu
            500                 505

<210> SEQ ID NO 7
<211> LENGTH: 1662
<212> TYPE: DNA
<213> ORGANISM: Scytalidium thermophilium

<400> SEQUENCE: 7
atgcgtaccg ccaagttcgc caccctcgcc gcccttgtgg cctcggccgc cgcccagcag      60
gcgtgcagcc tcaccaccga gaggcaccct tccctctcct ggaagaagtg caccgccggc     120
ggccagtgcc agaccgtcca ggcttccatc actctcgact ccaactggcg ctggactcac     180
caggtgtctg ctccaccaa ctgctacacg ggcaacgagt gggattctag catctgcact     240
gatgccaagt cgtgcgctca gaactgctgc gtcgatggtg ctgactacac cagcacctat     300
ggcatcacca ccaacggtga ttccctgagc ctcaagttcg tcaccaaggg ccagtactcg     360
accaacgtcg gctcgcgtac ctacctgatg gacggcgagg acaagtatca gagtaggttc     420
tatcttcagc cttctcgcgc cttgaatcct ggctaacttt tacacttcac agccttcgag     480
ctcctcggca acgagttcac cttcgatgtc gatgtctcca acatcggctg cggtctcaac     540
ggcgccctgt acttcgtctc catggacgcc gatggtggtc tcagccgcta tcctggcaac     600
aaggctggtg ccaagtacgg taccggctac tgcgatgctc agtgcccccg tgacatcaag     660
ttcatcaacg gcgaggccaa cattgagggc tggaccggct ccaccaacga ccccaacgcc     720
ggcgcgggcc gctatggtac ctgctgctct gagatggata tctgggaggc caacaacatg     780
gctactgcct tcactcctca cccttgcact atcattggcc agagccgctg cgagggcgac     840
tcgtgcggtg gcacctacag caacgaccgc tacgccggcg tctgcgaccc cgatggctgc     900
```

```
gacttcaacg cgtatcgcca gggcaacaag accttctacg gcaagggcat gaccgtcgac      960
accaccaaga agctcaccgt cgtcacccag ttcctcaagg acgccaacgg cgatctcggc     1020
gagatcaagc gcttctacgt ccaggatggg aagatcatcc ccaactccga gtccaccatc     1080
cccggcgtcg agggcaactc catcacccag gattggtgcg accgcagaa ggttgccttt      1140
ggcgacattg acgacttcaa ccgcaagggc ggcatgaagc agatgggcaa ggccctcgcc     1200
ggccccatgt cctggtcat gtccatctgg gatgaccacg cctccaacat gctctggctc      1260
gactcgacct ccctgtcga tgccgctggc aagcccggcg ccgagcgcgg tgcctgcccg      1320
accacctcgg gtgtccctgc tgaggttgag gccgaggccc caacagcaa cgtcgtcttc      1380
tccaacatcc gcttcggccc catcggctcg accgttgccg gccttccag cgatggcggc      1440
aacaacggcg gcaacaccac cgtccagccc ccgcccagca ccaccaccac ctctgccagc     1500
agcagcacca cctcggctcc tgccaccacc accaccgcca gcgctggccc caaggctggc     1560
cgctggcagc agtgcggcgg catcggcttc actggcccga cccagtgcga ggagccctac     1620
acttgcacca agctcaacga ctggtactct cagtgcctgt aa                        1662

<210> SEQ ID NO 8
<211> LENGTH: 1602
<212> TYPE: DNA
<213> ORGANISM: Scytalidium thermophilium

<400> SEQUENCE: 8
atgcgtaccg ccaagttcgc caccctcgcc gcccttgtgg cctcggccgc cgcccagcag       60
gcgtgcagcc tcaccaccga gaggcaccct tccctctcct ggaagaagtg caccgccggc      120
ggccagtgcc agaccgtcca ggcttccatc actctcgact ccaactggcg ctggactcac      180
caggtgtctg gctccaccaa ctgctacacg ggcaacgagt gggattctag catctgcact      240
gatgccaagt cgtgcgctca gaactgctgc gtcgatggtg ctgactacac cagcacctat      300
ggcatcacca ccaacggtga ttccctgagc ctcaagttcg tcaccaaggg ccagtactcg      360
accaacgtcg gctcgcgtac ctacctgatg gacggcgagg acaagtatca gaccttcgag      420
ctcctcggca acgagttcac cttcgatgtc gatgtctcca acatcggctg cggtctcaac      480
ggcgccctgt acttcgtctc catggacgcc gatggtggtc tcagccgcta tcctggcaac      540
aaggctggtg ccaagtacgg taccggctac tgcgatgctc agtgccccg tgacatcaag      600
ttcatcaacg gcgaggccaa cattgagggc tggaccggct ccaccaacga cccaacgcc      660
ggcgcgggcc gctatggtac ctgctgctct gagatggata tctgggaggc caacaacatg      720
gctactgcct tcactcctca cccttgcact atcattggcc agagccgctg cgagggcgac      780
tcgtgcggtg gcacctacag caacgaccgc tacgccggcg tctgcgaccc cgatggctgc      840
gacttcaacg cgtatcgcca gggcaacaag accttctacg gcaagggcat gaccgtcgac      900
accaccaaga agctcaccgt cgtcacccag ttcctcaagg acgccaacgg cgatctcggc      960
gagatcaagc gcttctacgt ccaggatggg aagatcatcc ccaactccga gtccaccatc     1020
cccggcgtcg agggcaactc catcacccag gattggtgcg accgcagaa ggttgccttt      1080
ggcgacattg acgacttcaa ccgcaagggc ggcatgaagc agatgggcaa ggccctcgcc     1140
ggccccatgg tcctggtcat gtccatctgg gatgaccacg cctccaacat gctctggctc     1200
gactcgacct ccctgtcga tgccgctggc aagcccggcg ccgagcgcgg tgcctgcccg      1260
accacctcgg gtgtccctgc tgaggttgag gccgaggccc caacagcaa cgtcgtcttc      1320
```

```
                                                    -continued tccaacatcc gcttcggccc catcggctcg accgttgccg gccttcccag cgatggcggc    1380
aacaacggcg gcaacaccac cgtccagccc ccgcccagca ccaccaccac ctctgccagc    1440
agcagcacca cctcggctcc tgccaccacc accaccgcca gcgctggccc caaggctggc    1500
cgctggcagc agtgcggcgg catcggcttc actggcccga cccagtgcga ggagccctac    1560
acttgcacca agctcaacga ctggtactct cagtgcctgt aa                       1602

<210> SEQ ID NO 9
<211> LENGTH: 533
<212> TYPE: PRT
<213> ORGANISM: Scytalidium thermophilium

<400> SEQUENCE: 9

Met Arg Thr Ala Lys Phe Ala Thr Leu Ala Ala Leu Val Ala Ser Ala
1               5                   10                  15

Ala Ala Gln Gln Ala Cys Ser Leu Thr Thr Glu Arg His Pro Ser Leu
            20                  25                  30

Ser Trp Lys Lys Cys Thr Ala Gly Gly Gln Cys Gln Thr Val Gln Ala
        35                  40                  45

Ser Ile Thr Leu Asp Ser Asn Trp Arg Trp Thr His Gln Val Ser Gly
    50                  55                  60

Ser Thr Asn Cys Tyr Thr Gly Asn Glu Trp Asp Ser Ser Ile Cys Thr
65                  70                  75                  80

Asp Ala Lys Ser Cys Ala Gln Asn Cys Cys Val Asp Gly Ala Asp Tyr
                85                  90                  95

Thr Ser Thr Tyr Gly Ile Thr Thr Asn Gly Asp Ser Leu Ser Leu Lys
            100                 105                 110

Phe Val Thr Lys Gly Gln Tyr Ser Thr Asn Val Gly Ser Arg Thr Tyr
        115                 120                 125

Leu Met Asp Gly Glu Asp Lys Tyr Gln Thr Phe Glu Leu Leu Gly Asn
    130                 135                 140

Glu Phe Thr Phe Asp Val Asp Val Ser Asn Ile Gly Cys Gly Leu Asn
145                 150                 155                 160

Gly Ala Leu Tyr Phe Val Ser Met Asp Ala Asp Gly Gly Leu Ser Arg
                165                 170                 175

Tyr Pro Gly Asn Lys Ala Gly Ala Lys Tyr Gly Thr Gly Tyr Cys Asp
            180                 185                 190

Ala Gln Cys Pro Arg Asp Ile Lys Phe Ile Asn Gly Glu Ala Asn Ile
        195                 200                 205

Glu Gly Trp Thr Gly Ser Thr Asn Asp Pro Asn Ala Gly Ala Gly Arg
    210                 215                 220

Tyr Gly Thr Cys Cys Ser Glu Met Asp Ile Trp Glu Ala Asn Asn Met
225                 230                 235                 240

Ala Thr Ala Phe Thr Pro His Pro Cys Thr Ile Ile Gly Gln Ser Arg
                245                 250                 255

Cys Glu Gly Asp Ser Cys Gly Gly Thr Tyr Ser Asn Asp Arg Tyr Ala
            260                 265                 270

Gly Val Cys Asp Pro Asp Gly Cys Asp Phe Asn Ala Tyr Arg Gln Gly
        275                 280                 285

Asn Lys Thr Phe Tyr Gly Lys Gly Met Thr Val Asp Thr Lys Lys
    290                 295                 300

Leu Thr Val Val Thr Gln Phe Leu Lys Asp Ala Asn Gly Asp Leu Gly
305                 310                 315                 320

Glu Ile Lys Arg Phe Tyr Val Gln Asp Gly Lys Ile Ile Pro Asn Ser
```

```
                    325                 330                 335
Glu Ser Thr Ile Pro Gly Val Glu Gly Asn Ser Ile Thr Gln Asp Trp
                340                 345                 350

Cys Asp Arg Gln Lys Val Ala Phe Gly Asp Ile Asp Asp Phe Asn Arg
                355                 360                 365

Lys Gly Gly Met Lys Gln Met Gly Lys Ala Leu Ala Gly Pro Met Val
            370                 375                 380

Leu Val Met Ser Ile Trp Asp Asp His Ala Ser Asn Met Leu Trp Leu
385                 390                 395                 400

Asp Ser Thr Phe Pro Val Asp Ala Ala Gly Lys Pro Gly Ala Glu Arg
                405                 410                 415

Gly Ala Cys Pro Thr Thr Ser Gly Val Pro Ala Glu Val Glu Ala Glu
                420                 425                 430

Ala Pro Asn Ser Asn Val Val Phe Ser Asn Ile Arg Phe Gly Pro Ile
                435                 440                 445

Gly Ser Thr Val Ala Gly Leu Pro Ser Asp Gly Gly Asn Asn Gly Gly
            450                 455                 460

Asn Thr Thr Val Gln Pro Pro Pro Ser Thr Thr Thr Ser Ala Ser
465                 470                 475                 480

Ser Ser Thr Thr Ser Ala Pro Ala Thr Thr Thr Ala Ser Ala Gly
                485                 490                 495

Pro Lys Ala Gly Arg Trp Gln Gln Cys Gly Gly Ile Gly Phe Thr Gly
                500                 505                 510

Pro Thr Gln Cys Glu Glu Pro Tyr Thr Cys Thr Lys Leu Asn Asp Trp
                515                 520                 525

Tyr Ser Gln Cys Leu
            530

<210> SEQ ID NO 10
<211> LENGTH: 497
<212> TYPE: PRT
<213> ORGANISM: Hypocrea jecorina

<400> SEQUENCE: 10

Gln Ser Ala Cys Thr Leu Gln Ser Glu Thr His Pro Pro Leu Thr Trp
1               5                   10                  15

Gln Lys Cys Ser Ser Gly Gly Thr Cys Thr Gln Gln Thr Gly Ser Val
                20                  25                  30

Val Ile Asp Ala Asn Trp Arg Trp Thr His Ala Thr Asn Ser Ser Thr
            35                  40                  45

Asn Cys Tyr Asp Gly Asn Thr Trp Ser Ser Thr Leu Cys Pro Asp Asn
50                  55                  60

Glu Thr Cys Ala Lys Asn Cys Cys Leu Asp Gly Ala Ala Tyr Ala Ser
65                  70                  75                  80

Thr Tyr Gly Val Thr Thr Ser Gly Asn Ser Leu Ser Ile Gly Phe Val
                85                  90                  95

Thr Gln Ser Ala Gln Lys Asn Val Gly Ala Arg Leu Tyr Leu Met Ala
                100                 105                 110

Ser Asp Thr Thr Tyr Gln Glu Phe Thr Leu Leu Gly Asn Glu Phe Ser
            115                 120                 125

Phe Asp Val Asp Val Ser Gln Leu Pro Cys Gly Leu Asn Gly Ala Leu
130                 135                 140

Tyr Phe Val Ser Met Asp Ala Asp Gly Gly Val Ser Lys Tyr Pro Thr
145                 150                 155                 160
```

```
Asn Thr Ala Gly Ala Lys Tyr Gly Thr Gly Tyr Cys Asp Ser Gln Cys
            165                 170                 175

Pro Arg Asp Leu Lys Phe Ile Asn Gly Gln Ala Asn Val Glu Gly Trp
        180                 185                 190

Glu Pro Ser Ser Asn Asn Ala Asn Thr Gly Ile Gly Gly His Gly Ser
    195                 200                 205

Cys Cys Ser Glu Met Asp Ile Trp Glu Ala Asn Ser Ile Ser Glu Ala
210                 215                 220

Leu Thr Pro His Pro Cys Thr Thr Val Gly Gln Glu Ile Cys Glu Gly
225                 230                 235                 240

Asp Gly Cys Gly Gly Thr Tyr Ser Asp Asn Arg Tyr Gly Gly Thr Cys
                245                 250                 255

Asp Pro Asp Gly Cys Asp Trp Asn Pro Tyr Arg Leu Gly Asn Thr Ser
            260                 265                 270

Phe Tyr Gly Pro Gly Ser Ser Phe Thr Leu Asp Thr Lys Lys Leu
        275                 280                 285

Thr Val Val Thr Gln Phe Glu Thr Ser Gly Ala Ile Asn Arg Tyr Tyr
    290                 295                 300

Val Gln Asn Gly Val Thr Phe Gln Gln Pro Asn Ala Glu Leu Gly Ser
305                 310                 315                 320

Tyr Ser Gly Asn Glu Leu Asn Asp Asp Tyr Cys Thr Ala Glu Glu Ala
                325                 330                 335

Glu Phe Gly Gly Ser Ser Phe Ser Asp Lys Gly Gly Leu Thr Gln Phe
            340                 345                 350

Lys Lys Ala Thr Ser Gly Gly Met Val Leu Val Met Ser Leu Trp Asp
        355                 360                 365

Asp Tyr Tyr Ala Asn Met Leu Trp Leu Asp Ser Thr Tyr Pro Thr Asn
370                 375                 380

Glu Thr Ser Ser Thr Pro Gly Ala Val Arg Gly Ser Cys Ser Thr Ser
385                 390                 395                 400

Ser Gly Val Pro Ala Gln Val Glu Ser Gln Ser Pro Asn Ala Lys Val
                405                 410                 415

Thr Phe Ser Asn Ile Lys Phe Gly Pro Ile Gly Ser Thr Gly Asn Pro
            420                 425                 430

Ser Gly Gly Asn Pro Pro Gly Gly Asn Pro Pro Gly Thr Thr Thr Thr
        435                 440                 445

Arg Arg Pro Ala Thr Thr Thr Gly Ser Ser Pro Gly Pro Thr Gln Ser
450                 455                 460

His Tyr Gly Gln Cys Gly Gly Ile Gly Tyr Ser Gly Pro Thr Val Cys
465                 470                 475                 480

Ala Ser Gly Thr Thr Cys Gln Val Leu Asn Pro Tyr Tyr Ser Gln Cys
                485                 490                 495

Leu

<210> SEQ ID NO 11
<211> LENGTH: 515
<212> TYPE: PRT
<213> ORGANISM: Scytalidium thermophilium

<400> SEQUENCE: 11

Gln Gln Ala Cys Ser Leu Thr Thr Glu Arg His Pro Ser Leu Ser Trp
  1               5                  10                  15

Lys Lys Cys Thr Ala Gly Gly Gln Cys Gln Thr Val Gln Ala Ser Ile
            20                  25                  30
```

```
Thr Leu Asp Ser Asn Trp Arg Trp Thr His Gln Val Ser Gly Ser Thr
        35                  40                  45

Asn Cys Tyr Thr Gly Asn Glu Trp Asp Ser Ser Ile Cys Thr Asp Ala
 50                  55                  60

Lys Ser Cys Ala Gln Asn Cys Cys Val Asp Gly Ala Asp Tyr Thr Ser
 65                  70                  75                  80

Thr Tyr Gly Ile Thr Thr Asn Gly Asp Ser Leu Ser Leu Lys Phe Val
                 85                  90                  95

Thr Lys Gly Gln Tyr Ser Thr Asn Val Gly Ser Arg Thr Tyr Leu Met
                100                 105                 110

Asp Gly Glu Asp Lys Tyr Gln Thr Phe Glu Leu Leu Gly Asn Glu Phe
            115                 120                 125

Thr Phe Asp Val Asp Val Ser Asn Ile Gly Cys Gly Leu Asn Gly Ala
        130                 135                 140

Leu Tyr Phe Val Ser Met Asp Ala Asp Gly Gly Leu Ser Arg Tyr Pro
145                 150                 155                 160

Gly Asn Lys Ala Gly Ala Lys Tyr Gly Thr Gly Tyr Cys Asp Ala Gln
                165                 170                 175

Cys Pro Arg Asp Ile Lys Phe Ile Asn Gly Glu Ala Asn Ile Glu Gly
            180                 185                 190

Trp Thr Gly Ser Thr Asn Asp Pro Asn Ala Gly Ala Gly Arg Tyr Gly
        195                 200                 205

Thr Cys Cys Ser Glu Met Asp Ile Trp Glu Ala Asn Asn Met Ala Thr
210                 215                 220

Ala Phe Thr Pro His Pro Cys Thr Ile Ile Gly Gln Ser Arg Cys Glu
225                 230                 235                 240

Gly Asp Ser Cys Gly Gly Thr Tyr Ser Asn Asp Arg Tyr Ala Gly Val
                245                 250                 255

Cys Asp Pro Asp Gly Cys Asp Phe Asn Ala Tyr Arg Gln Gly Asn Lys
            260                 265                 270

Thr Phe Tyr Gly Lys Gly Met Thr Val Asp Thr Thr Lys Lys Leu Thr
        275                 280                 285

Val Val Thr Gln Phe Leu Lys Asp Ala Asn Gly Asp Leu Gly Glu Ile
290                 295                 300

Lys Arg Phe Tyr Val Gln Asp Gly Lys Ile Ile Pro Asn Ser Glu Ser
305                 310                 315                 320

Thr Ile Pro Gly Val Glu Gly Asn Ser Ile Thr Gln Asp Trp Cys Asp
                325                 330                 335

Arg Gln Lys Val Ala Phe Gly Asp Ile Asp Asp Phe Asn Arg Lys Gly
            340                 345                 350

Gly Met Lys Gln Met Gly Lys Ala Leu Ala Gly Pro Met Val Leu Val
        355                 360                 365

Met Ser Ile Trp Asp Asp His Ala Ser Asn Met Leu Trp Leu Asp Ser
        370                 375                 380

Thr Phe Pro Val Asp Ala Ala Gly Lys Pro Gly Ala Glu Arg Gly Ala
385                 390                 395                 400

Cys Pro Thr Thr Ser Gly Val Pro Ala Glu Val Glu Ala Glu Ala Pro
                405                 410                 415

Asn Ser Asn Val Val Phe Ser Asn Ile Arg Phe Gly Pro Ile Gly Ser
            420                 425                 430

Thr Val Ala Gly Leu Pro Ser Asp Gly Gly Asn Asn Gly Gly Asn Thr
        435                 440                 445

Thr Val Gln Pro Pro Pro Ser Thr Thr Thr Thr Ser Ala Ser Ser Ser
```

```
                 450                 455                 460

Thr Thr Ser Ala Pro Ala Thr Thr Thr Ala Ser Ala Gly Pro Lys
465                 470                 475                 480

Ala Gly Arg Trp Gln Gln Cys Gly Gly Ile Gly Phe Thr Pro Thr
                485                 490                 495

Gln Cys Glu Glu Pro Tyr Thr Cys Thr Lys Leu Asn Asp Trp Tyr Ser
            500                 505                 510

Gln Cys Leu
        515

<210> SEQ ID NO 12
<211> LENGTH: 507
<212> TYPE: PRT
<213> ORGANISM: Artificial Sequence
<220> FEATURE:
<223> OTHER INFORMATION: consensus sequence

<400> SEQUENCE: 12

Gln Gln Ala Cys Ser Leu Thr Thr Glu Arg His Pro Ser Leu Ser Trp
  1               5                  10                  15

Lys Lys Cys Thr Ala Gly Gly Gln Cys Gln Thr Val Gln Ala Ser Ile
             20                  25                  30

Thr Leu Asp Ser Asn Trp Arg Trp Thr His Gln Val Ser Gly Ser Thr
         35                  40                  45

Asn Cys Tyr Thr Gly Asn Lys Trp Asp Ser Ser Ile Cys Thr Asp Ala
     50                  55                  60

Lys Ser Cys Ala Gln Asn Cys Cys Val Asp Gly Ala Asp Tyr Thr Ser
 65                  70                  75                  80

Thr Tyr Gly Ile Thr Thr Asn Gly Asp Ser Leu Ser Leu Lys Phe Val
                 85                  90                  95

Thr Lys Gly Gln His Ser Thr Asn Val Gly Ser Arg Thr Tyr Leu Met
            100                 105                 110

Asp Gly Glu Asp Lys Tyr Gln Thr Phe Glu Leu Leu Gly Asn Glu Phe
        115                 120                 125

Thr Phe Asp Val Asp Val Ser Asn Ile Gly Cys Gly Leu Asn Gly Ala
    130                 135                 140

Leu Tyr Phe Val Ser Met Asp Ala Asp Gly Gly Leu Ser Arg Tyr Pro
145                 150                 155                 160

Gly Asn Lys Ala Gly Ala Lys Tyr Gly Thr Gly Tyr Cys Asp Ala Gln
                165                 170                 175

Cys Pro Arg Asp Ile Lys Phe Ile Asn Gly Glu Ala Asn Ile Glu Gly
            180                 185                 190

Trp Thr Gly Ser Thr Asn Asp Pro Asn Ala Gly Ala Gly Arg Tyr Gly
        195                 200                 205

Thr Cys Cys Ser Glu Met Asp Ile Trp Glu Ala Asn Asn Met Ala Thr
    210                 215                 220

Ala Phe Thr Pro His Pro Cys Thr Ile Ile Gly Gln Ser Arg Cys Glu
225                 230                 235                 240

Gly Asp Ser Cys Gly Gly Thr Tyr Ser Asn Glu Arg Tyr Ala Gly Val
                245                 250                 255

Cys Asp Pro Asp Gly Cys Asp Phe Asn Ser Tyr Arg Gln Gly Asn Lys
            260                 265                 270

Thr Phe Tyr Gly Lys Gly Met Thr Val Asp Thr Thr Lys Lys Ile Thr
        275                 280                 285

Val Val Thr Gln Phe Leu Lys Asp Ala Asn Gly Asp Leu Gly Glu Ile
```

```
            290                 295                 300
Lys Arg Phe Tyr Val Gln Asp Gly Lys Ile Ile Pro Asn Ser Glu Ser
305                 310                 315                 320

Thr Ile Pro Gly Val Glu Gly Asn Ser Ile Thr Gln Asp Trp Cys Asp
                325                 330                 335

Arg Gln Lys Val Ala Phe Gly Asp Ile Asp Asp Phe Asn Arg Lys Gly
                340                 345                 350

Gly Met Lys Gln Met Gly Lys Ala Leu Ala Gly Pro Met Val Leu Val
            355                 360                 365

Met Ser Ile Trp Asp Asp His Ala Ser Asn Met Leu Trp Leu Asp Ser
    370                 375                 380

Thr Phe Pro Val Asp Ala Ala Gly Lys Pro Gly Ala Glu Arg Gly Ala
385                 390                 395                 400

Cys Pro Thr Thr Ser Gly Val Pro Ala Glu Val Glu Ala Glu Ala Pro
                405                 410                 415

Asn Ser Asn Val Val Phe Ser Asn Ile Arg Phe Gly Pro Ile Gly Ser
                420                 425                 430

Thr Val Ala Gly Leu Pro Gly Ala Gly Asn Gly Gly Asn Asn Gly Gly
            435                 440                 445

Asn Pro Pro Pro Pro Thr Thr Thr Ser Ser Ala Pro Ala Thr Thr
    450                 455                 460

Thr Thr Ala Ser Ala Gly Pro Lys Ala Gly Arg Trp Gln Gln Cys Gly
465                 470                 475                 480

Gly Ile Gly Phe Thr Gly Pro Thr Gln Cys Glu Glu Pro Tyr Thr Cys
                485                 490                 495

Thr Lys Leu Asn Asp Trp Tyr Ser Gln Cys Leu
                500                 505

<210> SEQ ID NO 13
<211> LENGTH: 507
<212> TYPE: PRT
<213> ORGANISM: Artificial Sequence
<220> FEATURE:
<223> OTHER INFORMATION: consensus sequence

<400> SEQUENCE: 13

Gln Gln Ala Cys Ser Leu Thr Thr Glu Arg His Pro Ser Leu Ser Trp
1               5                   10                  15

Lys Lys Cys Thr Ala Gly Gly Gln Cys Gln Thr Val Gln Ala Ser Ile
                20                  25                  30

Thr Leu Asp Ser Asn Trp Arg Trp Thr His Gln Val Ser Gly Ser Thr
            35                  40                  45

Asn Cys Tyr Thr Gly Asn Lys Trp Asp Thr Ser Ile Cys Thr Asp Ala
    50                  55                  60

Lys Ser Cys Ala Gln Asn Cys Cys Val Asp Gly Ala Asp Tyr Thr Ser
65                  70                  75                  80

Thr Tyr Gly Ile Thr Thr Asn Gly Asp Ser Leu Ser Leu Lys Phe Val
                85                  90                  95

Thr Lys Gly Gln His Ser Thr Asn Val Gly Ser Arg Thr Tyr Leu Met
            100                 105                 110

Asp Gly Glu Asp Lys Tyr Gln Thr Phe Glu Leu Leu Gly Asn Glu Phe
        115                 120                 125

Thr Phe Asp Val Asp Val Ser Asn Ile Gly Cys Gly Leu Asn Gly Ala
    130                 135                 140

Leu Tyr Phe Val Ser Met Asp Ala Asp Gly Gly Leu Ser Arg Tyr Pro
```

```
                145                 150                 155                 160
        Gly Asn Lys Ala Gly Ala Lys Tyr Gly Thr Gly Tyr Cys Asp Ala Gln
                        165                 170                 175

Cys Pro Arg Asp Ile Lys Phe Ile Asn Gly Glu Ala Asn Ile Glu Gly
                        180                 185                 190

Trp Thr Gly Ser Thr Asn Asp Pro Asn Ala Gly Ala Gly Arg Tyr Gly
                        195                 200                 205

Thr Cys Cys Ser Glu Met Asp Ile Trp Glu Ala Asn Asn Met Ala Thr
                        210                 215                 220

Ala Phe Thr Pro His Pro Cys Thr Ile Ile Gly Gln Ser Arg Cys Glu
        225                 230                 235                 240

Gly Asp Ser Cys Gly Gly Thr Tyr Ser Asn Glu Arg Tyr Ala Gly Val
                        245                 250                 255

Cys Asp Pro Asp Gly Cys Asp Phe Asn Ser Tyr Arg Gln Gly Asn Lys
                        260                 265                 270

Thr Phe Tyr Gly Lys Gly Met Thr Val Asp Thr Thr Lys Lys Ile Thr
                        275                 280                 285

Val Val Thr Gln Phe Leu Lys Asp Ala Asn Gly Asp Leu Gly Glu Ile
                        290                 295                 300

Lys Arg Phe Tyr Val Gln Asp Gly Lys Ile Ile Pro Asn Ser Glu Ser
        305                 310                 315                 320

Thr Ile Pro Gly Val Glu Gly Asn Ser Ile Thr Gln Asp Trp Cys Asp
                        325                 330                 335

Arg Gln Lys Val Ala Phe Gly Asp Ile Asp Asp Phe Asn Arg Lys Gly
                        340                 345                 350

Gly Met Lys Gln Met Gly Lys Ala Leu Ala Gly Pro Met Val Leu Val
                        355                 360                 365

Met Ser Ile Trp Asp Asp His Ala Ser Asn Met Leu Trp Leu Asp Ser
                        370                 375                 380

Thr Phe Pro Val Asp Ala Ala Gly Lys Pro Gly Ala Glu Arg Gly Ala
        385                 390                 395                 400

Cys Pro Thr Thr Ser Gly Val Pro Ala Glu Val Glu Ala Glu Ala Pro
                        405                 410                 415

Asn Ser Asn Val Val Phe Ser Asn Ile Arg Phe Gly Pro Ile Gly Ser
                        420                 425                 430

Thr Val Ala Gly Leu Pro Gly Ala Gly Asn Gly Asn Asn Gly Gly
                        435                 440                 445

Asn Pro Pro Pro Pro Thr Thr Thr Thr Ser Ser Ala Pro Ala Thr Thr
        450                 455                 460

Thr Thr Ala Ser Ala Gly Pro Lys Ala Gly Arg Trp Gln Gln Cys Gly
        465                 470                 475                 480

Gly Ile Gly Phe Thr Gly Pro Thr Gln Cys Glu Glu Pro Tyr Thr Cys
                        485                 490                 495

Thr Lys Leu Asn Asp Trp Tyr Ser Gln Cys Leu
                        500                 505
```

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
atgcgtaccg ccaagttcgc                                            20

```
<210> SEQ ID NO 15
<211> LENGTH: 22
<212> TYPE: DNA
<213> ORGANISM: Artificial Sequence
<220> FEATURE:
<223> OTHER INFORMATION: primer

<400> SEQUENCE: 15
ttacaggcac tgagagtacc ag                                              22
```